(12) United States Patent
Song et al.

(10) Patent No.: US 12,410,467 B2
(45) Date of Patent: Sep. 9, 2025

(54) BISULFITE-FREE, WHOLE GENOME METHYLATION ANALYSIS

(71) Applicant: LUDWIG INSTITUTE FOR CANCER RESEARCH LTD, Zurich (CH)

(72) Inventors: Chunxiao Song, Oxford (GB); Jingfei Cheng, Oxford (GB); Paulina Siejka-Zielinska, Oxford (GB); Yibin Liu, Oxford (GB)

(73) Assignee: LUDWIG INSTITUTE FOR CANCER RESEARCH LTD, Zurich (CH)

( * ) Notice: Subject to any disclaimer, the term of this patent is extended or adjusted under 35 U.S.C. 154(b) by 849 days.

(21) Appl. No.: 17/625,500

(22) PCT Filed: Jul. 8, 2020

(86) PCT No.: PCT/IB2020/056435
§ 371 (c)(1),
(2) Date: Jan. 7, 2022

(87) PCT Pub. No.: WO2021/005537
PCT Pub. Date: Jan. 14, 2021

(65) Prior Publication Data
US 2022/0275424 A1  Sep. 1, 2022

Related U.S. Application Data

(60) Provisional application No. 62/871,444, filed on Jul. 8, 2019.

(51) Int. Cl.
*C12Q 1/683* (2018.01)
*C12Q 1/6806* (2018.01)
*C12Q 1/6869* (2018.01)

(52) U.S. Cl.
CPC .......... *C12Q 1/683* (2013.01); *C12Q 1/6806* (2013.01); *C12Q 1/6869* (2013.01); *C12Q 2600/154* (2013.01)

(58) Field of Classification Search
CPC .......... C12Q 1/6869; C12Q 2521/531; C12Q 2523/115; C12Q 2521/301; C12Q 2525/117; C12Q 2525/191; C12Q 1/6827
See application file for complete search history.

(56) References Cited

U.S. PATENT DOCUMENTS

| 7,582,420 B2 | 9/2009 | Oliphant et al. |
| 8,741,567 B2 | 6/2014 | He et al. |

(Continued)

FOREIGN PATENT DOCUMENTS

| CN | 111971386 A | 11/2020 |
| CN | 115181783 A | 10/2022 |

(Continued)

OTHER PUBLICATIONS

Cheng et al. Nucleic Acids Research. 2021. 49(13):e76 and Supplemental. (Year: 2021).*

(Continued)

*Primary Examiner* — Joseph G. Dauner
(74) *Attorney, Agent, or Firm* — Casimir Jones, S.C.; J. Mitchell Jones

(57) ABSTRACT

This disclosure provides methods for cost-effective bisulfite-free identification in DNA, including whole genomic DNA, of the locations of one or more of 5-methylcytosine, 5-hydroxymethylcytosine, 5-carboxylcytosine and 5-formylcytosine. The methods described herein are based on the conversion of modified cytosine (5mC, 5hmC, 5fC, 5caC) to dihydrouracil (DHU), for example by TET-assisted pyridine borane treatment, followed by endonuclease cleavage of the DHU, and identification of the cleav- (Continued)

age site, which corresponds to the location of the modified cytosine.

8 Claims, 45 Drawing Sheets

Specification includes a Sequence Listing.

(56) References Cited

U.S. PATENT DOCUMENTS

| | | | |
|---|---|---|---|
| 9,267,117 | B2 | 2/2016 | Guan et al. |
| 2013/0157261 | A1* | 6/2013 | Sharpe ............... G01N 21/6458 435/7.1 |
| 2014/0127678 | A1 | 5/2014 | Guan et al. |
| 2014/0322707 | A1 | 10/2014 | He et al. |
| 2017/0176421 | A1 | 6/2017 | Rao et al. |
| 2017/0253924 | A1 | 9/2017 | Lu et al. |
| 2018/0251815 | A1 | 9/2018 | Okamoto et al. |
| 2020/0024643 | A1 | 1/2020 | Arensdorf et al. |
| 2020/0370114 | A1 | 11/2020 | Song et al. |

FOREIGN PATENT DOCUMENTS

| | | | |
|---|---|---|---|
| EP | 2694686 | 11/2017 | |
| WO | WO-2008091541 A1 | 7/2008 | |
| WO | WO 2013/017853 | 2/2013 | |
| WO | WO 2014/074450 | 5/2014 | |
| WO | WO 2014/083118 | 6/2014 | |
| WO | WO 2014/165770 | 10/2014 | |
| WO | WO 2015/021282 | 2/2015 | |
| WO | WO 2016/164363 | 10/2016 | |
| WO | WO 2017/039002 | 3/2017 | |
| WO | WO 2017/176630 | 10/2017 | |
| WO | WO-2017192633 A1 * | 11/2017 | ............. C12N 15/10 |
| WO | WO 2019/136413 | 7/2019 | |
| WO | WO-2024076981 A2 | 4/2024 | |

OTHER PUBLICATIONS

Liu et al. Nature Chem. Biol. 2017. 13:181-187. (Year: 2017).*
Ambrogelly et al., Screening of reducing agents for the PEGylation of recombinant human IL-10. Protein J. Jun. 2013;32(5):337-42.
Amemiya et al., The ENCODE Blacklist: Identification of Problematic Regions of the Genome. Sci Rep. Jun. 27, 2019;9(1):9354. 5 pages.
Aparici-Espert et al., A Combined Experimental and Theoretical Approach to the Photogeneration of 5,6-Dihydropyrimidin-5-yl Radicals in Nonaqueous Media. J Org Chem. May 20, 2016;81(10):4031-8.
Bachman et al., 5-Formylcytosine can be a stable DNA modification in mammals. Nat Chem Biol. Aug. 2015;11(8):555-7.
Bogu et al., Chromatin and RNA Maps Reveal Regulatory Long Noncoding RNAs in Mouse. Mol Cell Biol. Dec. 28, 2015;36(5):809-19.
Booth et al., Chemical methods for decoding cytosine modifications in DNA. Chem Rev. Mar. 25, 2015;115(6):2240-54.
Booth et al., Quantitative sequencing of 5-methylcytosine and 5-hydroxymethylcytosine at single-base resolution. Science. May 18, 2012;336(6083):934-7.
Chaurasia et al., Application of crude laccase of Xylaria polymorpha MTCC-1100 in selective oxidation of aromatic methyl group to aldehyde group. BCAIJ, 2012. 6(7), 237-242.
Darst et al., Bisulfite sequencing of DNA. Curr Protoc Mol Biol. Jul. 2010;Chapter 7:Unit 7.9.1-17.
Dietzsch et al., Chemoselective labeling and site-specific mapping of 5-formylcytosine as a cellular nucleic acid modification. FEBS Lett. Jun. 2018;592(12):2032-2047.
Dizdaroglu et al., Substrate specificity of the *Escherichia coli* endonuclease III: excision of thymine- and cytosine-derived lesions in DNA produced by radiation-generated free radicals. Biochemistry. Nov. 16, 1993;32(45):12105-11.

ENCODE Project Consortium. An integrated encyclopedia of DNA elements in the human genome. Nature. Sep. 6, 2012;489(7414):57-74.
Ernst et al., ChromHMM: autmating chromatin-state discovery and characterization. Nat Methods. Feb. 28, 2012;9(3):215-6.
Extended European Search Report for PCT/US2019012627. Mailed Sep. 21, 2020. 9 pages.
GenBank—EMBL Accession No. J02459. Jan. 2020. 33 pages.
He et al., DeepH&M: Estimating single-CpG hydroxymethylation and methylation levels from enrichment and restriction enzyme sequencing methods. Sci Adv. Jul. 1, 2020;6(27):eaba0521. 11 pages.
He et al., Tet-mediated formation of 5-carboxylcytosine and its excision by TDG in mammalian DNA. Science. Sep. 2, 2011;333(6047):1303-7.
Holmes et al., Performance evaluation of kits for bisulfite-conversion of DNA from tissues, cell lines, FFPE tissues, aspirates, lavages, effusions, plasma, serum, and urine. PLOS One. Apr. 3, 2014;9(4):e93933. 15 pages.
House et al., Hydrolysis of dihydrouridine and related compounds. Biochemistry. Jan. 9, 1996;35(1):315-20.
Incarnato et al., High-throughput single nucleotide variant discovery in E14 mouse embryonic stem cells provides a new reference genome assembly. Genomics. Aug. 2014;104(2):121-7.
International Search Report for PCT/US2019/012627, Mailed May 7, 2019. 5 pages.
International Search Report and Written Opinion for PCT/IB2020/056435. Mailed Oct. 19, 2020. 10 pages.
International Search Report and Written Opinion for PCT/IB2021/000630. Mailed Jan. 31, 2022. 21 pages.
International Search Report and Written Opinion, PCT/US2019/017902. Dated Apr. 11, 2019, 6 pages.
Ito et al., Tet proteins can convert 5-methylcytosine to 5-formylcytosine and 5-carboxylcytosine. Science. Sep. 2, 2011;333(6047):1300-3.
Iyer et al., Comparative genomics of transcription factors and chromatin proteins in parasitic protists and other eukaryotes. Int J Parasitol. Jan. 2008;38(1):1-31.
Jiang et al., Characterization of *Escherichia coli* endonuclease VIII. J Biol Chem. Dec. 19, 1997;272(51):32230-9.
Kellinger et al., 5-formylcytosine and 5-carboxylcytosine reduce the rate and substrate specificity of RNA polymerase II transcription. Nat Struct Mol Biol. Aug. 2012;19(8):831-3.
Kent et al., BigWig and BigBed: enabling browsing of large distributed datasets. Bioinformatics. Sep. 1, 2010;26(17):2204-7.
Kim et al., CTCF as a multifunctional protein in genome regulation and gene expression. Exp Mol Med. Jun. 5, 2015;47(6):e166. 5 pages.
Kriaucionis et al. The nuclear DNA base 5-hydroxymethylcytosine is present in Purkinje neurons and the brain. Science. May 15, 2009;324(5929):929-30.
Krueger et al., Bismark: a flexible aligner and methylation caller for Bisulfite-Seq applications. Bioinformatics. Jun. 1, 2011;27(11):1571-2.
Kundaje et al., mod/mouse/humanENCODE: Blacklisted genomic regions for functional genomics analysis. Stanford School of Medicine. 2014. 3 pages.
Langmead et al., Fast gapped-read alignment with Bowtie 2. Nat Methods. Mar. 4, 2012;9(4):357-9.
Li et al., DNA methylation in mammals. Cold Spring Harb Perspect Biol. May 1, 2014;6(5):a019133. 21 pages.
Li et al., Fast and accurate short read alignment with Burrows-Wheeler transform. Bioinformatics. Jul. 15, 2009;25(14):1754-60.
Li et al., The Sequence Alignment/Map format and SAMtools. Bioinformatics. Aug. 15, 2009;25(16):2078-9.
Liu et al., Accurate targeted long-read DNA methylation and hydroxymethylation sequencing with TAPS. Genome Biol. Mar. 3, 2020;21(1):54. 9 pages.
Liu et al., Bisulfite-free direct detection of 5-methylcytosine and 5-hydroxymethylcytosine at base resolution. Nat Biotechnol. Apr. 2019;37(4):424-429.
Liu et al., Bisulfite-free, Base-resolution, and Quantitative Sequencing of CytosineModifications. bioRxiv, 2018. pp. 1-18.

(56) References Cited

OTHER PUBLICATIONS

Liu et al., DNA 5-Methylcytosine-Specific Amplification and Sequencing. J Am Chem Soc. Mar. 11, 2020;142(10):4539-4543.
Lu et al., Chemical modification-assisted bisulfite sequencing (CAB-Seq) for 5-carboxylcytosine detection in Dna. J Am Chem Soc. Jun. 26, 2013;135(25):9315-7.
Matsushita et al., DNA-friendly Cu(ii)/TEMPO-catalyzed 5-hydroxymethylcytosine-specific oxidation. Chem Commun (Camb). May 23, 2017;53(42):5756-5759.
Meissner et al., Reduced representation bisulfite sequencing for comparative high-resolution DNA methylation analysis. Nucleic Acids Res. Oct. 13, 2005;33(18):5868-77.
Mellen et al., MeCP2 binds to 5hmC enriched within active genes and accessible chromatin in the nervous system. Cell. Dec. 21, 2012;151(7):1417-30.
Moriya et al., A novel modified nucleoside found at the first position of the anticodon of methionine tRNA from bovine liver mitochondria. Biochemistry. Mar. 1, 1994;33(8):2234-9.
Neri et al., Intragenic DNA methylation prevents spurious transcription initiation. Nature. Mar. 2, 2017;543(7643):72-77.
Nestor et al., Tissue type is a major modifier of the 5-hydroxymethylcytosine content of human genes. Genome Res. Mar. 2012;22(3):467-77.
Pais et al., Biochemical characterization of a Naegleria TET-like oxygenase and its application in single molecule sequencing of 5-methylcytosine. Proc Natl Acad Sci U S A. Apr. 7, 2015;112(14):4316-21.
Plongthongkum et al., Advances in the profiling of DNA modifications: cytosine methylation and beyond. Nat Rev Genet. Oct. 2014;15(10):647-61.
Ponnaluri et al., A mechanistic overview of TET-mediated 5-methylcytosine oxidation. Biochem Biophys Res Commun. Jun. 28, 2013;436(2):115-20.
Qu et al., MLML: consistent simultaneous estimates of DNA methylation and hydroxymethylation. Bioinformatics. Oct. 15, 2013;29(20):2645-6.
Quinlan et al., BEDTools: a flexible suite of utilities for comparing genomic features. Bioinformatics. Mar. 15, 2010;26(6):841-2.
Roberston et al., A novel method for the efficient and selective identification of 5-hydroxymethylcytosine in genomic DNA. Nucleic Acids Res. Apr. 2011;39(8):e55. pp. 1-10.
Robinson et al., Integrative genomics viewer. Nat Biotechnol. Jan. 2011;29(1):24-6.
Rosenbloom et al., ENCODE data in the UCSC Genome Browser: year 5 update. Nucleic Acids Res. Jan. 2013;41(Database issue):D56-63.
Ruhaak et al., 2-picoline-borane: a non-toxic reducing agent for oligosaccharide labeling by reductive amination. Proteomics. Jun. 2010;10(12):2330-6.
Schuler et al., Sequencing the sixth base (5-hydroxymethylcytosine): selective DNA oxidation enables base-pair resolution. Angew Chem Int Ed Engl. Oct. 22, 2012;51(43):10704-7.
Schutsky et al., Nondestructive, base-resolution sequencing of 5-hydroxymethylcytosine using a DNA deaminase. Nat Biotechnol. Oct. 8, 2018;10.1038/nbt.4204. 23 pages.
Shen et al., A map of the cis-regulatory sequences in the mouse genome. Nature. Aug. 2, 2012;488(7409):116-20.

Song et al., 5-Hydroxymethylcytosine signatures in cell-free DNA provide information about tumor types and stages. Cell Res. Oct. 2017;27(10):1-12.
Song et al., Genome-wide profiling of 5-formylcytosine reveals its roles in epigenetic priming. Cell. Apr. 25, 2013;153(3):678-91.
Song et al., Selective chemical labeling reveals the genome-wide distribution of 5-hydroxymethylcytosine. Nat Biotechnol. Jan. 2011;29(1):68-72.
Song. Bisulfite-free, base resolution and quantitative identification of cytosine modifications. Keystone Symposia Conference, DNA & RNA Methylation, Ludwig Institute for Cancer Research, University of Oxford, Jan. 24, 2018, pp. 1-18.
Tahiliani et al., Conversion of 5-methylcytosine to 5-hydroxymethylcytosine in mammalian DNA by MLL partner TET1. Science. May 15, 2009;324(5929):930-5.
Tanaka et al., Degradation of DNA by bisulfite treatment. Bioorg Med Chem Lett. Apr. 1, 2007;17(7):1912-5.
Therasse et. al., New guidelines to evaluate the response to treatment in solid tumors. European Organization for Research and Treatment of Cancer, National Cancer Institute of the United States, National Cancer Institute of Canada. J Natl Cancer Inst. Feb. 2, 2000;92(3):205-16.
Vaisvila et al., Enzymatic methyl sequencing detects DNA methylation at single-base resolution from picograms of DNA. Genome Res. Jun. 17, 2021;31(7):1280-1289.
Wang et al., Bisulfite-free, single base-resolution analysis of 5-hydroxymethylcytosine in genomic DNA by chemical-mediated mismatch. Chem Sci. Oct. 11, 2018;10(2):447-452.
Wen et al., Whole-genome analysis of 5-hydroxymethylcytosine and 5-methylcytosine at base resolution in the human brain. Genome Biol. Mar. 4, 2014;15(3):R49. 17 pages.
Written Opinion, PCT/US2019/012627. mailed May 7, 2019. 12 pages.
Wu et al., Base-resolution profiling of active DNA demethylation using MAB-seq and caMAB-seq. Nat Protoc. Jun. 2016;11(6):1081-100.
Xia et al., Bisulfite-free, base-resolution analysis of 5-formylcytosine at the genome scale. Nat Methods. Nov. 2015;12(11):1047-50.
Yu et al., Base-resolution analysis of 5-hydroxymethylcytosine in the mammalian genome. Cell. Jun. 8, 2012;149(6):1368-80.
Yu et al., Tet-assisted bisulfite sequencing of 5-hydroxymethylcytosine. Nat Protoc. Dec. 2012;7(12):2159-70.
Zeng et al., Bisulfite-Free, Nanoscale Analysis of 5-Hydroxymethylcytosine at Single Base Resolution. J Am Chem Soc. Oct. 17, 2018;140(41):13190-13194.
Zhao et al., Mapping the epigenetic modifications of DNA and RNA. Protein Cell. Nov. 2020;11(11):792-808.
Zhu et al., Single-Cell 5-Formylcytosine Landscapes of Mammalian Early Embryos and ESCs at Single-Base Resolution. Cell Stem Cell. May 4, 2017;20(5):720-731.e5.
Extended European Search Report for European Application No. 23203846.3, mailed Feb. 26, 2024, 10 Pages.
Guo Y., et al., "The Oxidative Dna Glycosylases of *Mycobacterium tuberculosis* Exhibit Different Substrate Preferences From Their *Escherichia coli* Counterparts," DNA Repair, Elsevier, Amsterdam, NL, Feb. 4, 2010, vol. 9, No. 2, pp. 177-190, XP026879108, (Jan. 29, 2010).
International Preliminary Report on Patentability for International Application No. PCT/IB2020/056435, mailed Jan. 20, 2022, 8 Pages.

* cited by examiner

Fig. 1

| pyridine borane 100% | 2-picoline borane 100% | tert-butylamine borane 100% | ammonia borane 100% |
| NaBH$_4$ | ethylenediamine borane ~30% | dimethylamine borane ~30% | sodium triacetoxyborohydride ~20% |
| sodium borohydride ~60% | 4-methylmorpholine borane n.d. | trimethylamine borane n.d. | dicyclohexylamine borane n.d. |
| morpholine boarne n.d. | | | |

A.

B.

A.

B.

A.

B.

C.

A

Library preparation kits for dsDNA

B

Library preparation kit for ssDNA

C

BISULFITE-FREE, WHOLE GENOME METHYLATION ANALYSIS

FIELD OF THE INVENTION

This disclosure provides methods for whole genome identification of the locations of 5-methylcytosine, 5-hydroxymethylcytosine, 5-carboxyl cytosine and/or 5-formylcytosine.

BACKGROUND

5-Methylcytosine (5mC) and 5-hydroxymethylcytosine (5hmC) are the two major epigenetic marks found in the mammalian genome. 5hmC is generated from 5mC by the ten-eleven translocation (TET) family dioxygenases. Tet can further oxidize 5hmC to 5-formylcytosine (5fC) and 5-carboxylcytosine (5caC), which exists in much lower abundance in the mammalian genome compared to 5mC and 5hmC (10-fold to 100-fold lower than that of 5hmC). Together, 5mC and 5hmC play crucial roles in a broad range of biological processes from gene regulation to normal development. Aberrant DNA methylation and hydroxymethylation have been associated with various diseases and are well-accepted hallmarks of cancer. Therefore, the determination of 5mC and 5hmC in DNA sequence is not only important for basic research, but also is valuable for clinical applications, including diagnosis and therapy.

5fC and 5caC are the two final oxidized derivatives of 5mC and can be converted to unmodified cytosine by Thymine DNA glycosylase (TDG) in the base excision repair pathway. Therefore, 5fC and 5caC are two important key intermediates in the active demethylation process, which plays important role in embryonic development. 5fC and 5caC are found in these contexts and may serve as indicator of nearly complete 5mC demethylation. 5fC and 5caC may also play additional functions such as binding specific proteins and affecting the rate and specificity of RNA polymerase II.

The current gold standard and most widely used method for DNA methylation and hydroxymethylation analysis is bisulfite sequencing (BS), and its derived methods such as Tet-assisted bisulfite sequencing (TAB-Seq) and oxidative bisulfite sequencing (oxBS). Likewise, bisulfite sequencing is the most well-established method for assaying whole genome DNA methylation. All of these methods employ bisulfite treatment to convert unmethylated cytosine to uracil while leaving 5mC and/or 5hmC intact. Through PCR amplification of the bisulfite-treated DNA, which reads uracil as thymine, the modification information of each cytosine can be inferred at a single base resolution (where the transition of C to T provides the location of the unmethylated cytosine). There are, however, at least two main drawbacks to bisulfite sequencing. First, bisulfite treatment is a harsh chemical reaction, which degrades more than 90% of the DNA due to depurination under the required acidic and thermal conditions. This degradation severely limits its application to low-input samples, such as clinical samples including circulating cell-free DNA and single-cell sequencing. Second, bisulfite sequencing relies on the complete conversion of unmodified cytosine to thymine. Unmodified cytosine accounts for approximately 95% of the total cytosine in the human genome. Converting all these positions to thymine severely reduces sequence complexity, leading to poor sequencing quality, low mapping rates, uneven genome coverage and increased sequencing cost. Bisulfite sequencing methods are also susceptible to false detection of 5mC and 5hmC due to incomplete conversion of unmodified cytosine to thymine.

Whole genome base-resolution methylome sequencing allows for the most comprehensive analysis of DNA methylation, however, the considerable sequencing cost often limits its applications. To reduce sequencing cost, Reduced Representation Bisulfite Sequencing (RRBS) may be used. However, it covers only a small proportion of CpG sites in specific sequence contexts and therefore does not yield a comprehensive methylation picture. Therefore, there is a need for approaches which achieve better coverage of mCpGs for lower cost.

SUMMARY OF THE INVENTION

The present disclosure provides methods for whole genome base-resolution methylome analysis. In embodiments, the methods identify the location of one or more of 5-methylcytosine, 5-hydroxymethylcytosine, 5-carboxylcytosine and/or 5-formylcytosine in a DNA sample. In embodiments, the DNA sample comprises a whole genome. The methods described herein provide for DNA methylation and hydroxymethylation analysis involving mild reactions that detect the modified cytosine with base-resolution without affecting the unmodified cytosine. Provided herein is an improved method for identifying 5mC and/or 5hmC by combining TET oxidation and reduction by borane derivatives (e.g., pyridine borane and 2-picoline borane (pic-BH$_3$)), referred to herein as TAPS (TET Assisted Pyridine borane Sequencing) (Table 1). TAPS detects modifications directly with high sensitivity and specificity, without affecting unmodified cytosines, and can be adopted to detect other cytosine modifications, as described herein. It is non-destructive, preserving DNA up to 10 kbs long. Compared with bisulfite sequencing, TAPS results in higher mapping rates, more even coverage and lower sequencing costs, enabling higher quality, more comprehensive and cheaper methylome analyses. Variations of this method that do not employ the oxidation step are used to identify 5fC and/or 5caC as described herein.

Compared to whole-genome bisulfite sequencing (WGBS), whole-genome TAPS (wgTAPS) reduces the sequencing cost by half. However, the cost of whole-genome sequencing is still prohibitive for many projects, especially considering 5mC and 5hmC accounts for only ~4% of all cytosine residues the mammalian genome, and thus around 65%-80% of reads generated by short read whole-genome sequencing do not contain any methylated CpG sites (mCpGs). To reduce sequencing cost, Reduced Representation Bisulfite Sequencing (RRBS) is a widely used method where CpG-rich regions are enriched by restriction endonucleases prior to bisulfite treatment. However, it covers only a small proportion of CpG sites in specific sequence contexts and therefore does not yield a comprehensive methylation picture. Therefore, there is a need for approaches which achieve better coverage of mCpGs for lower cost. In one embodiment, the present disclosure provides a modification of the TAPS method—referred to herein as endonuclease enrichment TAPS (eeTAPS)—that provides a new strategy for cost-effective genome-wide methylation analysis at single-CpG resolution. In other embodiments, the disclosure provides modifications of variants of the TAPS method (e.g., TAPSβ and CAPS) that can be used to detect 5mC, 5hmC, 5fC, and/or 5caC.

Thus, the present disclosure provides low cost methods for whole genome identification of one or more of 5-methylcytosine, 5-hydroxymethylcytosine, 5-carboxylcytosine and/or 5-formylcytosine. The methods described herein are based on the conversion of modified cytosine (5mC, 5hmC, 5fC, 5caC) to dihydrouracil (DHU), for example by TET-assisted pyridine borane treatment, followed by endonuclease cleavage of the DHU site to generate DNA fragments, which are then made into a sequencing library. Unfragmented genomic DNA cannot be sequenced directly—only when there is a modified cytosine, which is converted to DHU—will the DNA be cleaved into DNA fragments, which can then be sequenced with each end of the fragments indicating the position of the modified cytosine. By sequencing the cleaved fragments, methylated cytosine in the original DNA sample can be identified at base-resolution. Furthermore, since highly methylated cytosine tends to be cleaved more often than lowly methylated sites, this method can be used to semi-quantify DNA methylation.

In one aspect, the present disclosure provides a method for identifying 5mC or 5hmC in a DNA sample comprising the steps of:
a. providing a DNA sample comprising target DNA having 5mC and/or 5hmC;
b. modifying the DNA comprising the steps of:
   i. converting the 5mC and 5hmC in the DNA sample to 5-carboxylcytosine (5caC) and/or 5fC; and
   ii. converting the 5caC and/or 5fC to DHU to provide a modified DNA sample comprising modified target DNA; and
c. cleaving the modified target DNA;
d. adding adapter DNA molecules to the cleaved modified target DNA; and
e. detecting the sequence of the modified target DNA;
wherein the presence of a cleavage site provides the location of either a 5mC or 5hmC in the target DNA.

In another aspect, the present disclosure provides a method for identifying 5-methylcytosine (5mC) in a DNA sample comprising the steps of:
a. providing a DNA sample comprising target DNA;
b. modifying the DNA sample comprising the steps of:
   i. adding a blocking group to the 5-hydroxymethylcytosine (5hmC) in the DNA sample;
   ii. converting the 5mC in the DNA sample to 5-carboxylcytosine (5caC) and/or 5-formylcytosine (5fC); and
   iii. converting the 5caC and/or 5fC to dihydrouracil (DHU) to provide a modified DNA sample comprising modified target DNA;
c. cleaving the modified target DNA;
d. adding adapter DNA molecules to the cleaved modified target DNA; and
e. detecting the sequence of the modified target DNA;
wherein the presence of a cleavage site provides the location of a 5mC in the target DNA.

In another aspect, the present disclosure provides a method for identifying 5mC or 5hmC in a DNA sample comprising the steps of:
a. providing a DNA sample comprising target DNA having 5mC and/or 5hmC;
b. modifying the DNA comprising the steps of:
   i. converting the 5mC and 5hmC in the DNA sample to 5-carboxylcytosine (5caC) and/or 5fC; and
   ii. converting the 5caC and/or 5fC to DHU to provide a modified DNA sample comprising modified target DNA; and
c. cleaving the modified target DNA;
d. adding adapter DNA molecules to the cleaved modified target DNA; and
e. detecting the sequence of the modified target DNA;
wherein the presence of a cleavage site provides the location of either a 5mC or 5hmC in the target DNA.

In another aspect, the disclosure provides a method for identifying 5mC and identifying 5hmC in a DNA sample comprising:
a. identifying 5mC in the DNA sample comprising the steps of:
   i. providing a first DNA sample comprising target DNA having 5mC and/or 5hmC;
   ii. modifying the DNA in the first sample comprising the steps of:
      1. adding a blocking group to the 5-hydroxymethylcytosine (5hmC) in the first DNA sample;
      2. converting the 5mC in the first DNA sample to 5caC and/or 5fC; and
      3. converting the 5caC and/or 5fC to DHU to provide a modified first DNA sample comprising modified target DNA;
   iii. cleaving the modified target DNA;
   iv. adding adapter DNA molecules to the cleaved modified target DNA; and
   v. detecting the sequence of the modified target DNA; wherein the presence of a cleavage site provides the location of a 5mC in the target DNA.
b. identifying 5mC or 5hmC in the DNA sample comprising the steps of:
   i. providing a second DNA sample comprising target DNA having 5mC and/or 5hmC;
   ii. modifying the DNA in the second sample comprising the steps of:
      1. converting the 5mC and 5hmC in the second DNA sample to 5caC and/or 5fC; and
      2. converting the 5caC and/or 5fC to DHU to provide a modified second DNA sample comprising modified target DNA;
   iii. cleaving the modified target DNA;
   iv. adding adapter DNA molecules to the cleaved modified target DNA; and
   v. detecting the sequence of the modified target DNA from the second sample; wherein the presence of a cleavage site provides the location of either a 5mC or 5hmC in the target DNA; and
c. comparing the results of steps (a) and (b), wherein a cleavage site present in step (b) but not in step (a) provides the location of 5hmC in the target DNA.

In embodiments, the blocking group added to 5hmC in the DNA sample is a sugar. In embodiments, the sugar is a naturally-occurring sugar or a modified sugar, for example glucose or a modified glucose. In embodiments, the blocking group is added to 5hmC by contacting the DNA sample with UDP linked to a sugar, for example UDP-glucose or UDP linked to a modified glucose in the presence of a glucosyltransferase enzyme, for example, T4 bacteriophage β-glucosyltransferase (βGT) and T4 bacteriophage α-glucosyltransferase (αGT) and derivatives and analogs thereof.

In embodiments, the step of converting the 5mC in the DNA sample to 5caC and/or 5fC and the step of converting the 5mC and 5hmC in the DNA sample to 5caC and/or 5fC each comprises contacting the DNA sample with a ten eleven translocation (TET) enzyme. In further embodiments, the TET enzyme is one or more of human TET1, TET2, and TET3; murine Tet1, Tet2, and Tet3; Naegleria TET (NgTET); *Coprinopsis cinerea* (CcTET) and derivatives or analogues thereof. In embodiments, the TET enzyme is NgTET, or derivatives thereof. In embodiments, the TET enzyme is mouse mTet1 (mTet1CD) or derivatives thereof.

In other embodiments the TET enzyme is human TET2 (hTET2) or derivatives thereof.

In another aspect, the disclosure provides a method for identifying 5caC or 5fC in a DNA sample comprising the steps of:
a. providing a DNA sample comprising target DNA having 5caC and/or 5fC;
b. converting the 5caC and 5fC to DHU to provide a modified DNA sample comprising modified target DNA;
c. cleaving the modified target DNA;
d. adding adapter DNA molecules to the cleaved modified target DNA; and
e. detecting the sequence of the modified target DNA; wherein the presence of a cleavage site provides the location of either a 5caC or 5fC in the target DNA.

In another aspect, the disclosure provides a method for identifying 5caC in a DNA sample comprising the steps of:
a. providing a DNA sample comprising the target DNA having 5caC;
b. adding a blocking group to the 5fC in the DNA sample;
c. converting the 5caC to DHU to provide a modified DNA sample comprising modified target DNA;
d. cleaving the modified target DNA;
e. adding adapter DNA molecules to the cleaved modified target DNA; and
f. detecting the sequence of the modified target DNA; wherein the presence of a cleavage site provides the location of a 5caC in the target DNA.

In embodiments, adding a blocking group to the 5fC in the DNA sample comprises contacting the DNA with an aldehyde reactive compound including, for example, hydroxylamine derivatives (such as O-ethylhydroxylamine), hydrazine derivatives, and hydrazide derivatives.

In another aspect, the disclosure provides a method for identifying 5fC in a DNA sample comprising the steps of:
a. providing a DNA sample comprising target DNA having 5fC;
b. adding a blocking group to the 5caC in the DNA sample
c. converting the 5fC to DHU to provide a modified DNA sample comprising modified target DNA;
d. cleaving the modified target DNA;
e. adding adapter DNA molecules to the cleaved modified target DNA; and
f. detecting the sequence of the modified target DNA; wherein the presence of a cleavage site provides the location of a 5fC in the target DNA.

In embodiments, the step of adding a blocking group to the 5caC in the DNA sample comprises contacting the DNA sample with a carboxylic acid derivatization reagent, including, for example, 1-ethyl-3-(3-dimethylaminopropyl)carbodiimide (EDC) and (ii) an amine (such as ethylamine), hydrazine, or hydroxylamine compound.

In another aspect, the disclosure provides a method for identifying 5hmC in a DNA sample comprising:
a. providing a DNA sample comprising target DNA having 5hmC;
b. modifying the DNA in the sample comprising the steps of:
  i. converting the 5hmC in the DNA sample to 5caC and/or 5fC; and
  ii. converting the 5caC and/or 5fC to dihydrouracil (DHU) to provide a modified DNA sample comprising modified target DNA;
c. cleaving the modified target DNA;
d. adding adapter DNA molecules to the cleaved modified target DNA; and
e. detecting the sequence of the modified target DNA; wherein the presence of a cleavage site provides the location of 5hmC in the target DNA.

In embodiments, the step of converting the 5hmC to 5caC and/or 5fC comprises contacting the DNA sample with an oxidizing agent. In further embodiments, the oxidizing agent is potassium perruthenate, Cu(II)/TEMPO, potassium ruthenate, or manganese oxide.

In embodiments, the DNA sample comprises genomic DNA. In embodiments, the DNA sample comprises picogram quantities of DNA. In embodiments, the DNA sample comprises about 1 pg to about 900 pg DNA, about 1 pg to about 500 pg DNA, about 1 pg to about 100 pg DNA, about 1 pg to about 50 pg DNA, about 1 to about 10 pg, DNA, less than about 200 pg, less than about 100 pg DNA, less than about 50 pg DNA, less than about 20 pg DNA, and less than about 5 pg DNA. In other embodiments, the DNA sample comprises nanogram quantities of DNA. In embodiments, the DNA sample contains about 1 to about 500 ng of DNA, about 1 to about 200 ng of DNA, about 1 to about 100 ng of DNA, about 1 to about 50 ng of DNA, about 1 ng to about 10 ng of DNA, about 1 ng to about 5 ng of DNA, less than about 100 ng of DNA, less than about 50 ng of DNA less than about 5 ng of DNA, or less that about 2 ng of DNA. In embodiments, the DNA sample comprises circulating cell-free DNA (cfDNA). In embodiments, the DNA sample comprises microgram quantities of DNA.

In embodiments, the step of converting the 5caC and/or 5fC to DHU comprises contacting the DNA sample with a reducing agent including, for example, pyridine borane, 2-picoline borane (pic-$BH_3$), tert-butylamine borane, borane, sodium borohydride, sodium cyanoborohydride, and sodium triacetoxyborohydride. In a preferred embodiment, the reducing agent is pic-$BH_3$ and/or pyridine borane.

In embodiments, the step of cleaving the modified target DNA comprises specifically cleaving the modified target DNA containing DHU by contacting the modified DNA sample comprising the modified target DNA with one or more endonucleases that specifically cleave the modified target DNA due to the presence of DHU. In embodiments the endonuclease is a bifunctional DNA endonuclease with DNA N-glycosylase and AP lyase activity, including for example, Tma Endonuclease III, Endonuclease VIII, Formamidopyrimidine DNA Glycosylase (Fpg) and/or hNEIL1. In embodiments, the modified target DNA is cleaved using Uracil-Specific Excision Reagent (USER). The USER enzyme comprises a combination of Uracil DNA glycosylase (UDG) and Endonuclease VIII. Other enzymes that can be used, alone or in combination, to cleave the modified target DNA are Apurinic/apyrimidinic Endonuclease 1 (APE 1), UDG, Endonuclease III, Tma Endonuclease III, Tth Endonuclease IV, Endonuclease V, Endonuclease VIII, Fpg, and/or hNEIL1.

In embodiments, the methods above further comprise the step of size selecting the cleaved modified target DNA. In embodiments, the methods above further comprise the step of amplifying the copy number of the modified target DNA. In embodiments, this amplification step is performed prior to the step of detecting the sequence of the modified target DNA. The step of amplifying the copy number of the modified target DNA may be accomplished by performing the polymerase chain reaction (PCR), primer extension, and/or cloning.

In embodiments, the step of determining the sequence of the modified target DNA comprises chain termination sequencing, microarray, high-throughput sequencing, and restriction enzyme analysis. In embodiments, the step of detecting the sequence of the modified target DNA comprises a next generation sequencing method.

In one aspect the disclosure provides a method for cleaving a modified target DNA, the method comprising: contacting the modified target DNA comprising one or more DHU (i.e., DHU residues) with one or more endonucleases that cleave the modified target DNA at, or adjacent to, the one or more DHU. The one or more endonucleases may be, for example, any of the types of endonucleases, or combinations thereof, described herein. In embodiments, the one or more DHU in the modified target DNA are derived from 5mC and/or 5hmC, for example by the methods described herein. In embodiments, the one or more DHU in the modified target DNA are derived from 5caC and/or 5fC, for example, by the methods described herein.

In embodiments, the method further comprises, prior to the contacting step, modifying a target DNA comprising 5mC and/or 5hmC comprising the steps of: (i) converting the 5mC and 5hmC in the target DNA to 5-carboxylcytosine (5caC) and/or 5-formylcytosine (5fC), for example by the methods described herein; and (ii) converting the 5caC and/or 5fC to dihydrouracil (DHU), for example by the methods described herein, to provide the modified target DNA.

In embodiments, the method further comprises, prior to the contacting step, modifying a target DNA comprising 5mC and 5hmC comprising the steps of: (i) adding a blocking group to the 5hmC in the target DNA for example by the methods described herein; (ii) converting the 5mC in the target DNA to 5-carboxylcytosine (5caC) and/or 5-formylcytosine (5fC), for example by the methods described herein; and (iii) converting the 5caC and/or 5fC to dihydrouracil (DHU), for example by the methods described herein, to provide the modified target DNA.

In embodiments, the method further comprises, prior to the contacting step, modifying a target DNA comprising 5caC and/or 5fC comprising the step of converting the 5caC and/or 5fC to dihydrouracil (DHU), for example by the methods described herein, to provide the modified target DNA.

In embodiments, the method further comprises, prior to the contacting step, modifying a target DNA comprising 5caC and/or 5fC comprising the steps of: (i) adding a blocking group to the 5fC in the target DNA, for example by the methods described herein; and (ii) converting the 5caC to dihydrouracil (DHU), for example by the methods described herein, to provide the modified target DNA.

In embodiments, the method further comprises, prior to the contacting step, modifying a target DNA comprising 5caC and/or 5fC comprising the steps of: (i) adding a blocking group to the 5caC in the target DNA, for example by the methods described herein; and (ii) converting the 5fC to dihydrouracil (DHU), for example by the methods described herein, to provide the modified target DNA.

In embodiments, the method further comprises, prior to the contacting step, modifying a target DNA comprising 5mC and/or 5hmC comprising the steps of: (i) converting the 5mC in the target DNA to 5-carboxylcytosine (5caC) and/or 5-formylcytosine (5fC), for example by the methods described herein; and (ii) converting the 5caC and/or 5fC to dihydrouracil (DHU), for example by the methods described herein, to provide the modified target DNA.

BRIEF DESCRIPTION OF THE FIGURES

FIG. 1. Borane-containing compounds screening. Borane-containing compounds were screened for conversion of 5caC to DHU in an 11mer oligonucleotide ("oligo"), with conversion rate estimated by MALDI. 2-picoline borane (pic-borane), borane pyridine, and tert-butylamine borane could completely convert 5caC to DHU while ethylenediamine borane and dimethylamine borane gave around 30% conversion rate. No detectable products measured (n.d.) with dicyclohexylamine borane, morpholine borane, 4-methylmorpholine borane, and trimethylamine borane. Other reducing agents such as sodium borohydride and sodium tri(acetoxy)borohydride decomposed rapidly in acidic media and lead to incomplete conversion. Sodium cyanoborohydride was not used due to potential for hydrogen cyanide formation under acidic condition. Pic-borane and pyridine borane were chosen because of complete conversion, low toxicity and high stability.

(A) Methylation level measured by both eeTAPS (top line) and wgTAPS (bottom line) in chromosome 1 of the mESC. 100 kb windows were used, and a moving average value was calculated with the movAvg2 function in R with bw=10. (B) Density plot showing methylation level correlation between eeTAPS and wgTAPS in chromosomes bins. A 100 kb window was used to calculate the average methylation level in each bin. Pearson correlation coefficient is shown on the top of the plot. (C) Average methylation level across CpG Islands (CGI) and the 4 kb flanking regions for eeTAPS and wgTAPS. (D) Density plot showing methylation level correlation between eeTAPS and wgTAPS in CpG Islands. Pearson correlation coefficient is shown on the top of the plot. (E) Density plot showing methylation level correlation between eeTAPS and wgTAPS in different chromatin features. The chromatin features were previously defined with histone markers (Bogu, G. K., Vizan, P., Stanton, L. W., Beato, M., Di Croce, L. and Marti-Renom, M. A. (2015) Chromatin and RNA Maps Reveal Regulatory Long Noncoding RNAs in Mouse. *Mol Cell Biol*, 36, 809-819), and also shown in (F). Pearson correlation coefficient was shown on the top of the plot. (F) Boxplot showing the distribution of methylation level across all chromatin features as measured by eeTAPS (bottom bars) and wgTAPS (top bars).

Figure 33:
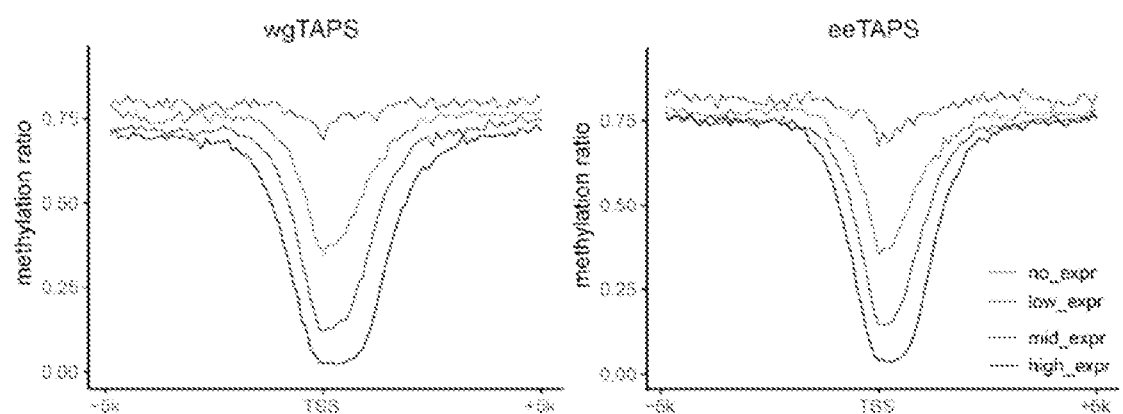

FIG. 33. Average methylation distribution around transcription start sites (TSS) in wgTAPS and eeTAPS. Genes were categorized by their expression level according to GSE72855 dataset.

FIG. 34A-F. eeTAPS analysis on low-input samples. (A) Number of mCpGs (identified by wgTAPS) detected using eeTAPS with 1 ng, 10 ng, 50 ng, 200 ng mESC gDNA input. For 200 ng mESC, reads were down-sampled to 2× to match the sequence depth for low-input sample. mCpG was designated using the following criteria: Methylation level >0.28 and cleaved count >1 was designated as mCpG in eeTAPS; methylation level >0.5 was designated as mCpG in wgTAPS. The percentages shown above the bars are the percentages of mCpG detected (mCpG detected in wgTAPS is defined as truth). (B) Heatmap showing eeTAPS-measured methylation distribution across the mouse genome using different input levels. Each chromosome was divided into 100 kb windows, represented by the heatmap rows. Methylation level was defined as the number of methylated CpG sites divided by the total number of covered CpG sites in each 100 kb window. (C) Density plots showing the correlation of methylation between low-input samples to the 200 ng input sample. Methylation level was calculated in 100 kb windows across the whole mouse genome as shown in (B). Pearson correlation coefficients are shown for each plot.

Figure 35:
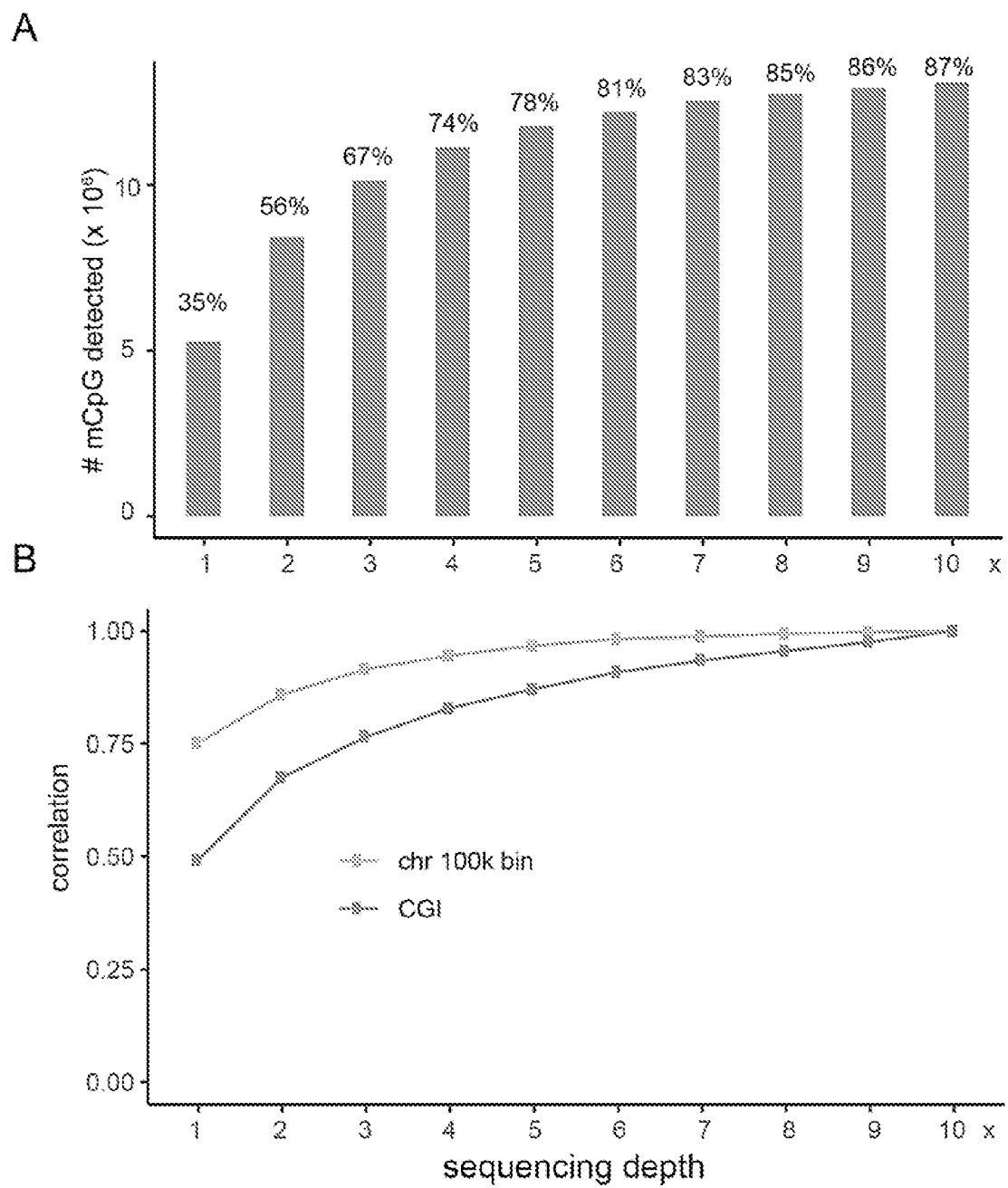

FIG. 35A-B. eeTAPS sequencing depth analysis. (A) Number of methylated CpGs that are detected when sampling reads from 1 to 10× sequencing depth. The percentage shown above is the percentage of mCpGs detected by eeTAPS (mCpG detected in wgTAPS is defined as truth). (B) The correlation of methylation in 100 kb windows across the whole mouse genome (top line) and at CpG islands (CGI) (bottom line) when sampling reads from 1 to 10× sequencing depth.

DETAILED DESCRIPTION OF THE INVENTION

The present disclosure provides a bisulfite-free, base-resolution method for identifying cytosine modifications in target DNA in a DNA sample, including whole genomic DNA. The methods described herein include improvements on the methods described in PCT/US2019/012627, incorporated herein by reference in its entirety, which describes methods including a bisulfite-free, base-resolution method for detecting 5mC and 5hmC in a sequence, named TAPS. TAPS consists of mild enzymatic and chemical reactions to detect 5mC and 5hmC directly and quantitatively at base-resolution without affecting unmodified cytosine. The present disclosure also provides improved methods to detect 5fC and 5caC at base resolution without affecting unmodified cytosine. Thus, the methods provided herein provide mapping of 5mC, 5hmC, 5fC and 5caC and overcome the disadvantages of previous methods such as bisulfite sequencing.

TABLE 1

Comparison of BS and related methods versus TAPS, TAPSβ and CAPS for 5 mC and 5 hmC sequencing.

| Base | BS | TAB-Seq | oxBS | TAPS | TAPSβ | CAPS |
|------|----|---------|------|------|-------|------|
| C | T | T | T | C | C | C |
| 5 mC | C | T | C | T | T | C |
| 5 hmC | C | C | T | T | C | T |

The methods described herein are based on the conversion of modified cytosine (5mC, 5hmC, 5fC, 5caC) to dihydrouracil (DHU), for example by TET-assisted pyridine borane treatment, followed by cleavage of the DHU site to generate DNA fragments (e.g., by USER (Uracil-Specific Excision Reagent)), which are then made into a sequencing library. Unfragmented genomic DNA cannot be sequenced directly. Only when there is a modified cytosine, which is converted to DHU, will the DNA be cleaved into DNA fragments, which can then be sequenced with each end of the fragments indicating the position of the modified cytosine. Thus, for example, eeTAPS reduces the cost of whole genome TAPS (WGTAPS) by only sequencing the cleaved fragments due to 5mC/5hmC conversion to DHU. By sequencing the cleaved fragments, methylated cytosine in the original DNA sample can be identified at base-resolution.

Methods for Identifying 5mC or 5hmC (Together)

In another aspect, the present disclosure provides a method for identifying 5mC or 5hmC in a DNA sample comprising the steps of:
  a. providing a DNA sample comprising target DNA;
  b. modifying the DNA comprising the steps of:
    i. converting the 5mC and 5hmC in the DNA sample to 5-carboxylcytosine (5caC) and/or 5fC; and ii. converting the 5caC and/or 5fC to DHU to provide a modified DNA sample comprising modified target DNA;
c. cleaving the modified target DNA;
d. adding adapter DNA molecules to the cleaved modified target DNA; and
e. detecting the sequence of the modified target DNA; wherein the presence of a cleavage site provides the location of either a 5mC or 5hmC in the target DNA.

In embodiments of the method for identifying 5mC or 5hmC in the target DNA, the method provides a semi-quantitative measure for the frequency the of 5mC or 5hmC modifications at each location where the modifications were identified in the target DNA. This method for identifying 5mC or 5hmC provides the location of 5mC and 5hmC, but does not distinguish between the two cytosine modifications. Rather, both 5mC and 5hmC are converted to DHU.

Methods for Identifying 5mC

In one aspect, the present disclosure provides a method for identifying 5-methylcytosine (5mC) in a DNA sample comprising the steps of:
a. providing a DNA sample comprising the target DNA;
b. modifying the DNA comprising the steps of:
    i. adding a blocking group to the 5-hydroxymethylcytosine (5hmC) in the DNA sample;
    ii. converting the 5mC in the DNA sample to 5-carboxylcytosine (5caC) and/or 5-formylcytosine (5fC); and
    iii. converting the 5caC and/or 5fC to DHU to provide a modified DNA sample comprising modified target DNA;
c. cleaving the modified target DNA;
d. adding adapter DNA molecules to the cleaved modified target DNA; and
e. detecting the sequence of the modified target DNA; wherein the presence of a cleavage site provides the location of a 5mC in the target DNA.

In embodiments of the method for identifying 5mC in the target DNA, the method provides a semi-quantitative measure for the frequency the of 5mC modification at each location where the modification was identified in the target DNA.

In order to identify 5mC in a target DNA without including 5hmC, the 5hmC in the sample is blocked so that it is not subject to conversion to 5caC and/or 5fC. In the methods of the present disclosure, 5hmC in the sample DNA are rendered non-reactive to the subsequent steps by adding a blocking group to the 5hmC. In one embodiment, the blocking group is a sugar, including a modified sugar, for example glucose or 6-azide-glucose (6-azido-6-deoxy-D-glucose). The sugar blocking group is added to the hydroxymethyl group of 5hmC by contacting the DNA sample with uridine diphosphate (UDP)-sugar in the presence of one or more glucosyltransferase enzymes.

In embodiments, the glucosyltransferase is T4 bacteriophage β-glucosyltransferase (βGT), T4 bacteriophage α-glucosyltransferase (αGT), and derivatives and analogs thereof. βGT is an enzyme that catalyzes a chemical reaction in which a beta-D-glucosyl (glucose) residue is transferred from UDP-glucose to a 5-hydroxymethylcytosine residue in a DNA.

By stating that the blocking group is, for example, glucose, this refers to a glucose moiety (e.g., a beta-D-glucosyl residue) being added to 5hmC to yield glucosyl 5-hydroxymethyl cytosine. The sugar blocking group can be any sugar or modified sugar that is a substrate of the glucosyltransferase enzyme and blocks the subsequent conversion of the 5hmC to 5caC and/or 5fC. The step of converting the 5mC in the DNA sample to 5caC and/or 5fC is then accomplished by the methods provided herein, such as by oxidation using a TET enzyme. And converting the 5caC and/or 5fC to DHU is accomplished by the methods provided herein, such by borane oxidation.

Methods for Identifying 5mC and Identifying 5hmC

The present disclosure provides a method for identifying 5mC and identifying 5hmC in a target DNA by (i) performing the method for identifying 5mC on a first DNA sample described herein, and (ii) performing the method for identifying 5mC or 5hmC on a second DNA sample described herein. The location of 5mC is provided by (i). By comparing the results of (i) and (ii), a cleavage site present in (i) but not in (ii) provides the location of 5hmC in the target DNA. In embodiments, the first and second DNA samples are derived from the same DNA sample. For example, the first and second samples may be separate aliquots taken from a sample comprising DNA to be analyzed.

Because the 5mC and 5hmC (that is not blocked) are converted to 5fC and 5caC before conversion to DHU, any existing 5fC and 5caC in the DNA sample will be detected as 5mC and/or 5hmC. However, given the extremely low levels of 5fC and 5caC in genomic DNA under normal conditions, this will often be acceptable when analyzing methylation and hydroxymethylation in a DNA sample. The 5fC and 5caC signals can be eliminated by protecting the 5fC and 5caC from conversion to DHU by, for example, hydroxylamine conjugation and EDC coupling, respectively.

The above method identifies the locations of 5hmC in the target DNA through the comparison of 5mC locations with the locations of 5mC or 5hmC (together). Alternatively, the location of 5hmC modifications in a target DNA can be measured directly. Thus, in one aspect the disclosure provides a method for identifying 5hmC in a DNA sample comprising the steps of:
a. providing a DNA sample comprising the target DNA;
b. modifying the DNA comprising the steps of:
    i. converting the 5hmC in the DNA sample to 5caC and/or 5fC; and
    ii. converting the 5caC and/or 5fC to DHU to provide a modified DNA sample comprising modified target DNA;
c. cleaving the modified target DNA;
d. adding adapter DNA molecules to the cleaved modified target DNA; and
e. detecting the sequence of the modified target DNA; wherein the presence of a cleavage site provides the location of 5hmC in the target DNA.

In embodiments, the step of converting the 5hmC to 5fC comprises oxidizing the 5hmC to 5fC by contacting the DNA with, for example, potassium perruthenate ($KRuO_4$) (as described in Science. 2012, 33, 934-937 and WO2013017853, incorporated herein by reference); or Cu(II)/TEMPO (copper(II) perchlorate and 2,2,6,6-tetramethylpiperidine-1-oxyl (TEMPO)) (as described in Chem. Commun., 2017, 53, 5756-5759 and WO2017039002, incorporated herein by reference). Other oxidizing agents that can be used are potassium ruthenate and/or manganese oxide. The 5fC in the DNA sample is then converted to DHU by the methods disclosed herein, e.g., by the borane reaction.

Methods for Identifying 5caC or 5fC

In one aspect, the disclosure provides a method for identifying 5caC or 5fC in a DNA sample comprising the steps of:

a. providing a DNA sample comprising the target DNA;
b. converting the 5caC and/or 5fC to DHU to provide a modified DNA sample comprising modified target DNA;
f. cleaving the modified target DNA;
g. adding adapter DNA molecules to the cleaved modified target DNA; and
h. detecting the sequence of the modified target DNA;
wherein the presence of a cleavage site provides the location of either a 5caC or 5fC in the target DNA.

This method for identifying 5fC or 5caC provides the location of 5fC or 5caC, but does not distinguish between these two cytosine modifications. Rather, both 5fC and 5caC are converted to DHU, which is detected by the methods described herein.

Methods for Identifying 5caC

In another aspect, the disclosure provides a method for identifying 5caC in a DNA sample comprising the steps of:
a. providing a DNA sample comprising target DNA;
b. adding a blocking group to the 5fC in the DNA sample;
c. converting the 5caC to DHU to provide a modified DNA sample comprising modified target DNA;
g. cleaving the modified target DNA;
h. adding adapter DNA molecules to the cleaved modified target DNA; and
i. detecting the sequence of the modified target DNA;
wherein the presence of a cleavage site provides the location of a 5caC in the target DNA.

In embodiments of the method for identifying 5caC in the target DNA, the method provides a semi-quantitative measure for the frequency of the 5caC modification at each location where the modification was identified in the target DNA.

In this method, 5fC is blocked (and 5mC and 5hmC are not converted to DHU) allowing identification of 5caC in the target DNA. In embodiments, adding a blocking group to the 5fC in the DNA sample comprises contacting the DNA with an aldehyde reactive compound including, for example, hydroxylamine derivatives, hydrazine derivatives, and hydrazide derivatives. Hydroxylamine derivatives include ashydroxylamine; hydroxylamine hydrochloride; hydroxylammonium acid sulfate; hydroxylamine phosphate; O-methylhydroxylamine; O-hexylhydroxylamine; O-pentylhydroxylamine; O-benzylhydroxylamine; and particularly, O-ethylhydroxylamine ($EtONH_2$), O-alkylated or O-arylated hydroxylamine, acid or salts thereof. Hydrazine derivatives include N-alkylhydrazine, N-arylhydrazine, N-benzylhydrazine, N,N-dialkylhydrazine, N,N-diarylhydrazine, N,N-dib enzylhydrazine, N,N-alkylbenzylhydrazine, N,N-arylbenzylhydrazine, and N,N-alkylarylhydrazine. Hydrazide derivatives include -toluenesulfonylhydrazide, N-acylhydrazide, N,N-alkylacylhydrazide, N,N-benzylacylhydrazide, N,N-arylacylhydrazide, N-sulfonylhydrazide, N,N-alkyl sulfonylhydrazide, N,N-benzyl sulfonylhydrazide, and N,N-aryl sulfonylhydrazide.

Methods for Identifying 5fC

In another aspect, the disclosure provides a method for identifying 5fC in a DNA sample comprising the steps of:
a. providing a DNA sample comprising the target DNA;
b. adding a blocking group to the 5caC in the DNA sample;
c. converting the 5fC to DHU to provide a modified DNA sample comprising modified target DNA;
d. cleaving the modified target DNA;
e. adding adapter DNA molecules to the cleaved modified target DNA; and
f. detecting the sequence of the modified target DNA;
wherein the presence of a cleavage site provides the location of a 5fC in the target DNA.

In embodiments of the method for identifying 5fC in the target DNA, the method provides a semi-quantitative measure for the frequency the of 5fC modification at each location where the modification was identified in the target DNA.

Adding a blocking group to the 5caC in the DNA sample can be accomplished by (i) contacting the DNA sample with a coupling agent, for example a carboxylic acid derivatization reagent like carbodiimide derivatives such as 1-ethyl-3-(3-dimethylaminopropyl)carbodiimide (EDC) or N,N'-dicyclohexylcarbodiimide (DCC) and (ii) contacting the DNA sample with an amine, hydrazine or hydroxylamine compound. Thus, for example, 5caC can be blocked by treating the DNA sample with EDC and then benzylamine, ethylamine or other amine to form an amide that blocks 5caC from conversion to DHU by, e.g., pic-$BH_3$. Methods for EDC-catalyzed 5caC coupling are described in WO2014165770, and are incorporated herein by reference.

DNA Sample/Target DNA

The methods of the present disclosure utilize mild enzymatic and chemical reactions that avoid the substantial degradation associated with methods like bisulfite sequencing. Thus, the methods are useful in analysis of low-input samples, such as circulating cell-free DNA and in single-cell analysis.

In embodiments, the DNA sample comprises picogram quantities of DNA. In embodiments, the DNA sample comprises about 1 pg to about 900 pg DNA, about 1 pg to about 500 pg DNA, about 1 pg to about 100 pg DNA, about 1 pg to about 50 pg DNA, about 1 to about 10 pg, DNA, less than about 200 pg, less than about 100 pg DNA, less than about 50 pg DNA, less than about 20 pg DNA, and less than about 5 pg DNA. In other embodiments, the DNA sample comprises nanogram quantities of DNA. The sample DNA for use in the methods disclosed herein can be any quantity including, DNA from a single cell or bulk DNA samples. In embodiments, the methods can be performed on a DNA sample comprising about 1 to about 500 ng of DNA, about 1 to about 200 ng of DNA, about 1 to about 100 ng of DNA, about 1 to about 50 ng of DNA, about 1 to about 10 ng of DNA, about 2 to about 5 ng of DNA, less than about 100 ng of DNA, less than about 50 ng of DNA less than 5 ng, and less than 2 ng of DNA. In embodiments, the DNA sample comprises microgram quantities of DNA.

Providing a DNA sample as used herein refers to obtaining a DNA sample from any source either directly or indirectly. A DNA sample used in the methods described herein may be from any source including, for example a body fluid, tissue sample, organ, organelle, or single cells. In embodiments, the DNA sample is circulating cell-free DNA (cell-free DNA or cfDNA), which is DNA found in the blood and is not present within a cell. cfDNA can be isolated from blood or plasma using methods known in the art. Commercial kits are available for isolation of cfDNA including, for example, the Circulating DNA Kit (Qiagen). The DNA sample may result from an enrichment step, including, but is not limited to antibody immunoprecipitation, chromatin immunoprecipitation, restriction enzyme digestion-based enrichment, hybridization-based enrichment, or chemical labeling-based enrichment.

The target DNA may be any DNA having cytosine modifications (i.e., 5mC, 5hmC, 5fC, and/or 5caC) including, but not limited to, DNA fragments or genomic DNA purified from tissues, organs, cells and organelles. The target DNA can be a single DNA molecule in the sample, or may be the entire population of DNA molecules in a sample (or a subset thereof) having a cytosine modification. The target DNA can be the native DNA from the source or pre-converted into a high-throughput sequencing-ready form, for example by fragmentation, repair and ligation with adaptors for sequencing. Thus, target DNA can comprise a plurality of DNA sequences such that the methods described herein may be used to generate a library of target DNA sequences that can be analyzed individually (e.g., by determining the sequence of individual targets) or in a group (e.g., by high-throughput or next generation sequencing methods).

A DNA sample comprising the target DNA can be obtained from an organism from the Monera (bacteria), Protista, Fungi, Plantae, and Animalia Kingdoms. DNA samples may be obtained from a patient or subject, from an environmental sample, or from an organism of interest. In embodiments, the DNA sample is extracted, purified, or derived from a cell or collection of cells, a body fluid, a tissue sample, an organ, and/or an organelle. In preferred embodiments, the sample DNA is whole genomic DNA.

Converting 5mC and 5hmC to 5caC and/or 5fC

Embodiments of the methods provided herein, such as the eeTAPS method described herein, include the step of converting the 5mC and 5hmC (or just the 5mC if the 5hmC is blocked) to 5caC and/or 5fC. In embodiments, this step comprises contacting the DNA sample with a ten eleven translocation (TET) enzyme. The TET enzymes are a family of enzymes that catalyze the transfer of an oxygen molecule to the N5 methyl group on 5mC resulting in the formation of 5-hydroxymethylcytosine (5hmC). TET further catalyzes the oxidation of 5hmC to 5fC and the oxidation of 5fC to form 5caC (see FIG. 5A). TET enzymes useful in the methods described herein include one or more of human TET1, TET2, and TET3; murine Tet1, Tet2, and Tet3; Naegleria TET (NgTET); *Coprinopsis cinerea* (CcTET) and derivatives or analogues thereof. In embodiments, the TET enzyme is NgTET, or derivateves thereof. In other embodiments the TET enzyme is human TET1 (hTET1), or derivateves thereof. In embodiments, the TET enzyme is mouse Tet1, or derivateves thereof (mTet1CD). In other embodiments the TET enzyme is human TET2 (hTET2), or derivateves thereof.

Converting 5caC and/or 5fC to DHU

Methods described herein include the step of converting the 5caC and/or 5fC in a DNA sample to DHU. In embodiments, this step comprises contacting the DNA sample with a reducing agent including, for example, a borane reducing agent such as pyridine borane, 2-picoline borane (pic-$BH_3$), borane, sodium borohydride, sodium cyanoborohydride, and sodium triacetoxyborohydride. In a preferred embodiment, the reducing agent is pyridine borane and/or pic-$BH_3$.

Cleaving the Modified Target DNA

The methods described herein include the step of cleaving the modified target DNA that contains DHU at positions where a modified cytosine (5mC, 5hmC, 5fC, and/or 5caC) were located in the DNA sample prior to the conversion step(s) (i.e., prior to the step or steps that converted the modified cytosine to DHU). The cleaving step described herein, specifically cleaves the modified target DNA containing DHU, while leaving the DNA not containing DHU uncleaved, or substantially uncleaved.

The step of cleaving the modified target DNA that contains DHU can be performed by contacting the modified target DNA containing DHU with one or more DNA endonucleases that specifically cleaves the modified target DNA. In embodiments, one or more of the DNA endonucleases is a bifunctional DNA endonuclease with DNA N-glycosylase and AP lyase activity, including for example, Tma Endonuclease III, Endonuclease VIII, Formamidopyrimidine DNA Glycosylase (Fpg) and/or hNEIL1. In embodiments, the modified target DNA that contains DHU is cleaved with Uracil-Specific Excision Reagent (USER). USER enzyme comprises a combination of Uracil DNA glycosylase (UDG) and the DNA glycosylase-lyase Endonuclease VIII. Other enzymes that can be used to cleave the modified target DNA are one or more of Apurinic/apyrimidinic Endonuclease 1 (APE 1), Endonuclease III (Endo III), Tma Endonuclease III, Tth Endonuclease IV, Endonuclease V, Endonuclease VIII, Fpg, and hNEIL1.

In embodiments, the step of cleaving the modified target DNA that contains DHU comprises exposing the modified target DNA to acidic pH and/or heat condition, as described in House C H, Miller S L. Hydrolysis of dihydrouridine and related compounds. Biochemistry. 1996; 35(1):315-320. In embodiments, the cleavage step comprises exposing the modified target DNA to temperatures of at least 70° C., 75° C., 80° C., 85° C., 90° C., 95° C., 100° C., 105° C. or 110° C. and/or pH at or above 7, 7.5, 8, 8.5, 9, 9.5, 10, 10.5, 11, 11.5, 12, 12.5, or 13.

Adding Adapter DNA Molecules to the Cleaved Modified Target DNA

In embodiments, the methods described herein comprise the step of adding adapter DNA molecules to the modified target DNA that has been cleaved, e.g., by a USER enzyme. An adapter DNA or DNA linker is a short, chemically-synthesized, single- or double-stranded oligonucleotide that can be ligated to one or both ends of other DNA molecules. Double-stranded adapters can be synthesized so that each end of the adapter has a blunt end or a 5' or 3' overhang (i.e., sticky ends). DNA adapters are ligated to the cleaved modified target DNA to provide sequences for PCR amplification with complimentary primers and/or for cloning and/or library creation (e.g., a next generation sequencing library).

Prior to ligation of the adapters to the cleaved target DNA, the ends of the cleaved DNA may be prepared for ligation by, for example, end repair, creating blunt ends with 5' phosphate groups. The blunt ends can be used for ligation to adapters or overhangs can be created prior to ligation by, e.g., a tailing reaction. Tailing is an enzymatic method for adding a non-templated nucleotide to the 3' end of a blunt, double-stranded DNA molecule. A-tailing of the 3' ends (i.e., adding a dA to the 3' ends) can be used to facilitate ligation to adapters with complementary dT-overhangs.

In embodiment, the cleaved target DNA is sized selected either before or after the step of adding the DNA adapter molecules to the cleaved modified target DNA. In embodiments, the size selection is performed after the DNA adapters have been added to the cleaved target DNA. Size selection can be performed by methods known in the art including, but not limited to solid-phase reversible immobilization (SPRI) paramagnetic beads (e.g., using AMPure XP beads).

Amplifying the Copy Number of Modified Target DNA

The methods described herein may optionally include the step of amplifying (increasing) the copy number of the modified target DNA by methods known in the art. When the modified target DNA is DNA, the copy number can be increased by, for example, PCR, cloning, and primer extension. The copy number of individual target DNAs can be amplified by PCR using primers specific for a particular target DNA sequence. Alternatively, a plurality of different modified target DNA sequences can be amplified by cloning into a DNA vector by standard techniques. In embodiments, the copy number of a plurality of different modified target DNA sequences is increased by PCR to generate a library for next generation sequencing where, e.g., double-stranded adapter DNA has been previously ligated to the sample DNA (or to the modified sample DNA) and PCR is performed using primers complimentary to the adapter DNA.

Creation of a Next Generation Sequencing Library

Once adapter DNA molecules are added to the cleaved modified target DNA, the copy number of the modified target DNA can be amplified (e.g., by PCR) to generate a library DNA sequences for next generation sequencing. The primers for PCR have sequences corresponding (complimentary) to the adapter DNA that has been previously ligated to the cleaved target DNA. The methods provided herein, including the reagents, the steps and their order, enable the generation of libraries of DNA sequences that can be sequenced using high-throughput next generation sequencing methods.

Detecting the Cleavage Site of the Modified Target DNA

In embodiments of the methods disclosed herein, the method comprises the step of detecting the sequence of the cleaved modified target DNA. The modified target DNA contains DHU at positions where one or more of 5mC, 5hmC, 5fC, and 5caC were present in the unmodified target DNA. The modified target DNA containing DHU is cleaved by the methods described herein, including DHU-sensitive endonuclease digestion. Cleaved fragments can then be converted into a sequencing library in which the beginning and the end of each fragment corresponds to the site of a modified cytosine (5mC, 5hmC, 5fC, or 5caC). This allows the methylated CpG sites to be enriched genome-wide while the vast majority of the genome with no methylation is depleted. Thus, the cytosine modifications can be detected by any method that identifies the cleavage site known in the art. Such methods include sequencing methods such as Sanger sequencing, microarray, and next generation sequencing methods.

Kits

The present disclosure additionally provides kits for identification of 5mC and 5hmC in a target DNA. Such kits comprise reagents for identification of 5mC and 5hmC by the methods described herein. The kits may also contain the reagents for identification of 5caC and for the identification of 5fC by the methods described herein. In embodiments, the kit comprises a TET enzyme, a borane reducing agent and instructions for performing the method. In further embodiments, the TET enzyme is TET1 or TET2 (or derivatives thereof) and the borane reducing agent is selected from one or more of the group consisting of pyridine borane, 2-picoline borane (pic-BH3), borane, sodium borohydride, sodium cyanoborohydride, and sodium triacetoxyborohydride. In a further embodiment, the TET1 enzyme is NgTet1, human TET1 or murine Tet1 and the borane reducing agent is pyridine borane and/or pic-BH$_3$. In other embodiments, the TET enzyme is mTET2, or a derivative thereof.

In embodiments, the kit further comprises a 5hmC blocking group and a glucosyltransferase enzyme. In further embodiments, the 5hmC blocking group is uridine diphosphate (UDP)-sugar where the sugar is glucose or a glucose derivative, and the glucosyltransferase enzyme is T4 bacteriophage β-glucosyltransferase (βGT), T4 bacteriophage α-glucosyltransferase (αGT), and derivatives and analogs thereof.

In embodiments the kit further comprises an oxidizing agent selected from one or more of potassium perruthenate (KRuO4), Cu(II)/TEMPO (copper(II) perchlorate and 2,2,6,6-tetramethylpiperidine-1-oxyl (TEMPO)), potassium ruthenate and manganese oxide.

In embodiments, the kit comprises reagents for blocking 5fC in the DNA sample. In embodiments, the kit comprises an aldehyde reactive compound including, for example, hydroxylamine derivatives, hydrazine derivatives, and hyrazide derivatives as described herein. In embodiments, the kit comprises reagents for blocking 5caC as described herein.

In embodiments, the kit comprises reagents for isolating DNA. In embodiments the kit comprises reagents for isolating low-input DNA from a sample, for example cfDNA from blood, plasma, or serum. In embodiments, the kit comprises reagents for isolating genomic DNA.

In embodiments, the kit comprises one or more enzymes for cleaving modified target DNA that contains DHU, as described herein. In embodiments, the kit comprises adapter DNA molecules as described herein. In addition, the kit may comprise an enzyme for ligating the adapter DNA molecules to the cleaved modified target DNA.

EXAMPLES

Example 1: TAPS and WGTAPS

Methods

Preparation of Model DNA.

DNA oligos for MALDI and HPLC-MS/MS test. DNA oligonucleotides ("oligos") with C, 5mC and 5hmC were purchased from Integrated DNA Technologies (IDT). All the sequences and modifications could be found in FIGS. 6 and 7. DNA oligo with 5fC was synthesized by the C-tailing method: DNA oligos 5'-GTCGACCGGATC-3' and 5'-TTG-GATCCGGTCGACTT-3' were annealed and then incubated with 5-formyl-2'-dCTP (Trilink Biotech) and Klenow Fragment 3'→5' exo- (New England Biolabs) in NEBuffer 2 for 2 hr at 37° C. The product was purified with Bio-Spin P-6 Gel Columns (Bio-Rad).

DNA oligo with 5caC was synthesized using Expedite 8900 DNA Synthesis System with standard phosphoramidites (Sigma) 5-Carboxy-dC-CE Phosphoramidite (Glen Research). Subsequent deprotection and purification were carried out with Glen-Pak Cartridges (Glen Research) according to the manufacturer's instructions. Purified oligonucleotides were characterized by Voyager-DE MALDI-TOF (matrix-assisted laser desorption ionization time-of-flight) Biospectrometry Workstation.

222 bp Model DNA for conversion test. To generate 222 bp model DNA containing five CpG sites, bacteriophage lambda DNA (Thermo Fisher) was PCR amplified using Taq DNA Polymerase (New England Biolabs) and purified by AMPure XP beads (Beckman Coulter). Primers sequences are as follows: FW-5'-CCTGATGAAACAAGCATGTC-3', RV-5'-CAUTACTCACUTCCCCACUT-3'. The uracil base in the reverse strand of PCR product was removed by USER enzyme (New England Biolabs). 100 ng of purified PCR product was then methylated in 20 µl solution containing 1× NEBuffer 2, 0.64 mM S-adenosylmethionine and 20 U M.SssI CpG Methyltransferase (New England Biolabs) for 2 hr at 37° C., followed by 20 min heat inactivation at 65° C. The methylated 222 bp model DNA was purified by AMPure XP beads.

Model DNA for TAPS, TAPSβ and CAPS validation with Sanger sequencing. 34 bp DNA oligo containing single 5mC and single 5hmC site was annealed with other DNA oligos in annealing buffer containing 5 mM Tris-Cl (pH 7.5), 5 mM MgCl$_2$, and 50 mM NaCl, and then ligated in a reaction containing 400 U T4 ligase (NEB) at 25° C. for 1 hr and purified by 1.8× AMPure XP beads.

| DNA | Sequence (5' to 3') |
|---|---|
| 34 bp mC and hmC | CCCGA$^m$CGCATGATCTGTA CTTGATCGAC$^{hm}$CGTGCAAC |
| TruSeq Universal Adapter | AATGATACGGCGACCACCGA GATCTACACTCTTTCCCTAC ACGACGCTCTTCCGATCT |
| TruSeq Adapter (Index 6) | /5Phos/GATCGGAAGAGCA CACGTCTGAACTCCAGTCAC GCCAATATCTCGTATGCCGT CTTCTGCTTG |
| Uracil linker | TCTTCCGAUCGTTGCACGGU CGATCAAGUACAGATCAT GCGUCGGGAGAUCGGAAG |

The Uracil linker was removed by USER enzyme after ligation reaction resulting in a final product sequence (5' to 3'):

AATGATACGGCGACCACCGAGATCTACACTCTTTCC

CTACACGACGCTCTTCCGATCTCCCGA$^m$CGCATGAT

CTGTACTTGATCGAC$^{hm}$CGTGCAACGATCGGAAGAG

CACACGTCTGAACTCCAGTCACGCCAATATCTCGTA

TGCCGTCTTCTGCTTG. PCR primers for amplification of the model DNA were: P5: 5'-AATGATACGGCGACCACCGAG-3' and P7: 5'-CAAGCAGAAGACGGCATACGAG-3'.

Model DNA for polymerase test and Sanger sequencing. Model DNA for polymerase test and Sanger sequencing was prepared with the same ligation method above except different DNA oligos were used:

| DNA | Sequence (5' to 3') |
|---|---|
| 34 bp mC TruSeq Universal Adapter | AGCAGTCT$^m$CGATCAGCTG$^m$CTACTGTA$^m$C GTAGCATAATGATACGGCGACCACCGAGA TCTACACTCTTTCCCTACACGACGCTCTT CCGATCT |
| TruSeq Adapter (Index 6) | /5Phos/GATCGGAAGAGCACACGTCTG AACTCCAGTCACGCCAATATCTCGTATG CCGTCTTCTGCTTG |
| Insert_1_ 40_bp | /5Phos/AGGTGCGCTAAGTTCTAGATC GCCAACTGGTTGTGGCCTT |
| Insert_2_ 60_bp | /5Phos/CTATAGCCGGCTTGCTCTCTC TGCCTCTAGCAGCTGCTCCCTATAGTGA GTCGTATTAAC |
| 40_bp-Linker-1 | ATCTAGAACTTAGCGCACCTAGATCGGA AGAGCGTCGTGT |
| 80_bp-Linker: | AGAGAGCAAGCCGGCTATAGATGCTACG TACAGTAGCAGCTGATCAAGACTGCTAA GGCCACAACCAGTTGGCG |
| 42_bp-Linker-2: | AGACGTGTGCTCTTCCGATCGTTAATAC GACTCACTATAGGG |

The final product sequence (5' to 3') was: AATGA-TACGGCGACCACCGAGATCTACACTCTTTCCCTA-CACGACGCTCTTCCGA TCTAGGTGCGCTAAGTTCTAGATCGC-CAACTGGTTGTGGCCTTAGCAGTCT$^m$CGA TCAGCTG$^m$CTACTGTA$^m$CGTAGCATC-TATAGCCGGCTTGCTCTCTCTGCCTCTAGC AGCTGCTCCCTATAGTGAGTCGTATTAACGATCG-GAAGAGCACACGTCTGAACTC CAGTCACGC-CAATATCTCGTATGCCGTCTTCTGCTTG. PCR primers to amplify the model DNA are the P5 and P7 primers provided above. Biotin-labelled primer sequence for primer extension is biotin linked to the 5' end of the P7 primer. PCR primers for RT-PCR after T7 RNA polymerase transcription were the P5 primer and RT: 5'-TGCTAGAGGCAGAGAGAGCAAG-3'.

Model DNA for PCR bias test. Model DNA for PCR bias test was prepared with the same ligation method above except different DNA oligos were used:

| DNA | Sequence (5' to 3') |
|---|---|
| 17 bp X | AGCAGTCTXGATCAGCT (X = DHU or U or T or C) |
| 17 bp No Modification | GCTACTGTACGTAGCAT |
| TruSeq Universal Adapter | AATGATACGGCGACCAC CGAGATCTACACTCTTT CCCTACACGACGCTCTT CCGATCT |
| TruSeq Adapter (Index 6) | /5Phos/GATCGGAAGA GCACACGTCTGAACTCC AGTCACGCCAATATCTC GTATGCCGTCTTCTGCT TG |
| Insert_1_ 40_bp | /5Phos/AGGTGCGCTA AGTTCTAGATCGCCAAC TGGTTGTGGCCTT |
| Insert_2_ 60_bp | /5Phos/CTATAGCCGG CTTGCTCTCTCTGCCTC TAGCAGCTGCTCCCTAT AGTGAGTCGTATTAAC |
| 40_bp-Linker-1 | ATCTAGAACTTAGCGCA CCTAGATCGGAAGAGCG TCGTGT |
| 80_bp-Linker | AGAGAGCAAGCCGGCTA TAGATGCTACGTACAGT AGCAGCTGATCAAGACT GCTAAGGCCACAACCAG TTGGCG |
| 42_bp-Linker-2 | AGACGTGTGCTCTTCCG ATCGTTAATACGACTCA CTATAGGG |

Final product sequence (5' to 3'): AATGATACGGCGAC-CACCGAGATCTACACTCTTTCCCTA-CACGACGCTCTTCCGA TCTAGGTGCGCTAAGTTCTAGATCGC-CAACTGGTTGTGGCCTTAGCAGTCTXGAT CAGCTGCTACTGTACGTAGCATC-TATAGCCGGCTTGCTCTCTCTGCCTCTAGCAGC TGCTCCCTATAGTGAGTCGTATTAACGATCG-GAAGAGCACACGTCTGAACTCCAG TCACGC-CAATATCTCGTATGCCGTCTTCTGCTTG, where X=DHU or U or T or C. PCR primer to amplify the model DNA are the P5 and P7 primers provided above.

Preparation of Methylated Bacteriophage Lambda Genomic DNA

1 µg of unmethylated bacteriophage lambda DNA (Promega) was methylated in 50 µL reaction containing 0.64 mM SAM and 0.8 U/µl M.SssI enzyme in $Mg^{2+}$-free buffer (10 mM Tris-Cl pH 8.0, 50 mM NaCl, and 10 mM EDTA) for 2 hours at 37° C. Then, 0.5 µL of M.SssI enzyme and 1 µL of SAM were added and the reaction was incubated for additional 2 hours at 37° C. Methylated DNA was subsequently purified on 1× Ampure XP beads. To assure complete methylation, the whole procedure was repeated in NEB buffer 2. DNA methylation was then validated with HpaII digestion assay. 50 ng of methylated and unmethylated DNA were digested in 10 µL reaction with 2 U of HpaII enzyme (NEB) in CutSmart buffer (NEB) for 1 h at 37° C. Digestion products were run on 1% agarose gel together with undigested lambda DNA control. Unmethylated lambda DNA was digested after the assay whereas methylated lambda DNA remained intact confirming complete and successful CpG methylation. Sequence of lambda DNA can be found in GenBank—EMBL Accession Number: J02459.

Preparation of 2 kb Unmodified Spike-In Controls 2 kb spike-in controls (2 kb-1, 2, 3) were PCR amplified from pNIC28-Bsa4 plasmid (Addgene, cat. no. 26103) in the reaction containing 1 ng DNA template, 0.5 µM primers, 1 U Phusion High-Fidelity DNA Polymerase (Thermo Fisher). PCR primer sequences are listed in Table 2.

TABLE 2

Sequences of PCR primers for spike-ins.

| Primer name | Sequence (5' to 3') |
| --- | --- |
| 2kb-3_Forward | CACAGATGTCTGCCTGTTCA |
| 2kb-3_Reverse | AGGGTGGTGAATGTGAAACC |

PCR product was purified on Zymo-Spin column. 2 kb unmodified control sequence (5' to 3'):

```
CACAGATGTCTGCCTGTTCATCCGCGTCCAGCTCGT
TGAGTTTCTCCAGAAGCGTTAATGTCTGGCTTCTG
ATAAAGCGGGCCATGTTAAGGGCGGTTTTTTCCTG
TTTGGTCACTGATGCCTCCGTGTAAGGGGGATTTC
TGTTCATGGGGGTAATGATACCGATGAAACGAGAG
AGGATGCTCACGATACGGGTTACTGATGATGAACA
TGCCCGGTTACTGGAACGTTGTGAGGGTAAACAAC
TGGCGGTATGGATGCGGCGGGACCAGAGAAAAATC
ACTCAGGGTCAATGCCAGCGCTTCGTTAATACAGA
TGTAGGTGTTCCACAGGGTAGCCAGCAGCATCCTG
CGATGCAGATCCGGAACATAATGGTGCAGGGCGCT
GACTTCCGCGTTTCCAGACTTTACGAAACACGGAA
ACCGAAGACCATTCATGTTGTTGCTCAGGTCGCAG
ACGTTTTGCAGCAGCAGTCGCTTCACGTTCGCTCG
CGTATCGGTGATTCATTCTGCTAACCAGTAAGGCA
ACCCCGCCAGCCTAGCCGGGTCCTCAACGACAGGA
GCACGATCATGCGCACCCGTGGGGCCGCCATGCCG
GCGATAATGGCCTGCTTCTCGCCGAAACGTTTGGT
GGCGGGACCAGTGACGAAGGCTTGAGCGAGGGCGT
GCAAGATTCCGAATACCGCAAGCGACAGGCCGATC
ATCGTCGCGCTCCAGCGAAAGCGGTCCTCGCCGAA
AATGACCCAGAGCGCTGCCGGCACCTGTCCTACGA
GTTGCATGATAAAGAAGACAGTCATAAGTGCGGCG
ACGATAGTCATGCCCCGCGCCCACCGGAAGGAGCT
GACTGGGTTGAAGGCTCTCAAGGGCATCGGTCGAG
ATCCCGGTGCCTAATGAGTGAGCTAACTTACATTA
ATTGCGTTGCGCTCACTGCCCGCTTTCCAGTCGGG
AAACCTGTCGTGCCAGCTGCATTAATGAATCGGCC
AACGCGCGGGAGAGGCGGTTTGCGTATTGGGCGC
CAGGGTGGTTTTTCTTTTCACCAGTGAGACGGGCA
ACAGCTGATTGCCCTTCACCGCCTGGCCCTGAGAG
AGTTGCAGCAAGCGGTCCACGCTGGTTTGCCCCAG
CAGGCGAAAATCCTGTTTGATGGTGGTTAACGGCG
GGATATAACATGAGCTGTCTTCGGTATCGTCGTAT
CCCACTACCGAGATATCCGCACCAACGCGCAGCCC
GGACTCGGTAATGGCGCGCATTGCGCCCAGCGCCA
TCTGATCGTTGGCAACCAGCATCGCAGTGGGAACG
ATGCCCTCATTCAGCATTTGCATGGTTTGTTGAAA
ACCGGACATGGCACTCCAGTCGCCTTCCCGTTCCG
CTATCGGCTGAATTTGATTGCGAGTGAGATATTTA
TGCCAGCCAGCCAGACGCAGACGCGCCGAGACAGA
ACTTAATGGGCCCGCTAACAGCGCGATTTGCTGGT
GACCCAATGCGACCAGATGCTCCACGCCCAGTCGC
GTACCGTCTTCATGGGAGAAAATAATACTGTTGAT
GGGTGTCTGGTCAGAGACATCAAGAAATAACGCCG
GAACATTAGTGCAGGCAGCTTCCACAGCAATGGCA
TCCTGGTCATCCAGCGGATAGTTAATGATCAGCCC
ACTGACGCGTTGCGCGAGAAGATTGTGCACCGCCG
CTTTACAGGCTTCGACGCCGCTTCGTTCTACCATC
GACACCACCACGCTGGCACCCAGTTGATCGGCGCG
AGATTTAATCGCCGCGACAATTTGCGACGGCGCGT
GCAGGGCCAGACTGGAGGTGGCAACGCCAATCAGC
AACGACTGTTTGCCCGCCAGTTGTTGTGCCACGCG
GTTGGGAATGTAATTCAGCTCCGCCATCGCCGCTT
CCACTTTTTCCCGCGTTTTCGCAGAAACGTGGCTG
```

```
GCCTGGTTCACCACGCGGGAAACGGTCTGATAAGA

GACACCGGCATACTCTGCGACATCGTATAACGTTA

CTGGTTTCACATTCACCACCCT
```

Preparation of 120Mer Spike-In Controls

120mer spike-in controls were produced by primer extension. Oligo sequences and primers are listed in the Table 3.

TABLE 3

Sequences of DNA oligos and primers used for preparation of 120mer control spike-ins.

| Spike-in control | Template sequence | Primer for extension (5' to 3') |
|---|---|---|
| 120mer-1 | ATACTCATCATTAAAC TTCGCCCTTACCTACC ACTTCGTGTATGTAGA TAGGTAGTATACAATT GATATCGAAATGAGTA CGTAGATAGTAGAAAG TAAGATGGAGGTGAGA GTGAGAGT | ATACTCATCATTAA ACTTCGCCCTTACC TACCACTTCG |
| 120mer-2 | GCGGCGTGATACTGGT CCCGAG5hmCCTGAAG TTAGGCC5hmCGGGAT GACTGA5hmCAGTCTT CCGAGACCGACGACAC AGGTCTCCCTATAGTG AGTCGTATTATGGCGA GAGAATGAATCTCCAT C | GATGGAGATTCATT CTCTCGCCATAATA CGACTCACTATAGG |

Briefly, for 120mer-1 spike-in, 3 µM oligo was annealed with 10 µM primer in the annealing buffer containing 5 mM Tris-Cl (pH 7.5), 5 mM MgCl$_2$, and 50 mM NaCl. For 120mer-2 spike-in, 5 µM oligo was annealed with 7.5 µM primer. Primer extension was performed in the NEB buffer 2 with 0.4 µM dNTPs (120mer-1: dATP/dGTP/dTTP/dhmCTP, 120mer-2: dATP/dGTP/dTTP/dCTP) and 5 U of Klenow Polymerase (New England Biolabs) for 1 hour at 37° C. After reaction spike-in controls were purified on Zymo-Spin columns (Zymo Research). The 120mer spike-in controls were then methylated in 50 µL reaction containing 0.64 mM SAM and 0.8 U/µl M.SssI enzyme in NEB buffer 2 for 2 hours at 37° C. and purified with Zymo-Spin columns. All spike-in sequences used can be downloaded from https://figshare.com/s/80c3ab713c261262494b.

Generation of Synthetic Spike-In with N5mCNN and N5hmCNN

Synthetic oligo with N5mCNN and N5hmCNN sequences was produced by annealing and extension method. Oligo sequences are listed in Table 4, below.

TABLE 4

| Oligo | Template sequence (5' to 3') |
|---|---|
| N5mCNN | GAAGATGCAGAAGACAGGAA GGATGAAACACTCAGGCGCA CGCTGGCATN$^m$CNNGACAAA CCACAAGAACAGGCTAGTGA GAATGAAGGGA |
| N5hmCNN | CCAACTCTGAAACCCACCAA CGCCAACATCCACCACACAA CCCAAGATN$^{hm}$CNNGACCAT |

TABLE 4-continued

| Oligo | Template sequence (5' to 3') |
|---|---|
| | CTTACAAACATATCCCTTCA TTCTCACTAGCC |

Briefly, 10 µM N5mCNN and N5hmCNN oligos (IDT) were annealed together in the annealing buffer containing 5 mM Tris-Cl (pH 7.5), 5 mM MgCl$_2$, and 50 mM NaCl. Extension was performed in the NEB buffer 2 with 0.4 mM dNTPs (dATP/dGTP/dTTP/dCTP) and 5 U of Klenow Polymerase (NEB) for 1 hour at 37° C. After reaction, spike-in control was purified on Zymo-Spin column (Zymo Research). Synthetic spike-in with N5mCNN and N5hmCNN (5' to 3'):

```
GAAGATGCAGAAGACAGGAAGGATGAAACACTCAGG

CGCACGCTGGCATNmCNNGACAAACCACAAGAACAG

GCTAGTGAGAATGAAGGGATATGTTTGTAAGATGGT

CNNGNATCTTGGGTTGTGTGGTGGATGTTGGCGTTG

GTGGGTTTCAGAGTTGG.
```

Complementary Strand (5' to 3'):

```
CCAACTCTGAAACCCACCAACGCCAACATCCACCAC

ACAACCCAAGATNhmCNNGACCATCTTACAAACATA

TCCCTTCATTCTCACTAGCCTGTTCTTGTGGTTTGT

CNNGNATGCCAGCGTGCGCCTGAGTGTTTCATCCTT

CCTGTCTTCTGCATCTTC.
```

DNA Digestion and HPLC-MS/MS Analysis

DNA samples were digested with 2 U of Nuclease P1 (Sigma-Aldrich) and 10 nM deaminase inhibitor erythro-9-Amino-β-hexyl-α-methyl-9H-purine-9-ethanol hydrochloride (Sigma-Aldrich). After overnight incubation at 37° C., the samples were further treated with 6 U of alkaline phosphatase (Sigma-Aldrich) and 0.5 U of phosphodiesterase I (Sigma-Aldrich) for 3 hours at 37° C. The digested DNA solution was filtered with Amicon Ultra-0.5 mL 10 K centrifugal filters (Merck Millipore) to remove the proteins, and subjected to HPLC-MS/MS analysis.

The HPLC-MS/MS analysis was carried out with 1290 Infinity LC Systems (Agilent) coupled with a 6495B Triple Quadrupole Mass Spectrometer (Agilent). A ZORBAX Eclipse Plus C18 column (2.1×150 mm, 1.8-Micron, Agilent) was used. The column temperature was maintained at 40° C., and the solvent system was water containing 10 mM ammonium acetate (pH 6.0, solvent A) and water-acetonitrile (60/40, v/v, solvent B) with 0.4 mL/min flow rate. The gradient was: 0-5 min; 0 solvent B; 5-8 min; 0-5.63% solvent B; 8-9 min; 5.63% solvent B; 9-16 min; 5.63-13.66% solvent B; 16-17 min; 13.66-100% solvent B; 17-21 min; 100% solvent B; 21-24.3 min; 100-0% solvent B; 24.3-25 min; 0% solvent B. The dynamic multiple reaction monitoring mode (dMRM) of the MS was used for quantification. The source-dependent parameters were as follows: gas temperature 230° C., gas flow 14 L/min, nebulizer 40 psi, sheath gas temperature 400° C., sheath gas flow 11 L/min, capillary voltage 1500 V in the positive ion mode, nozzle voltage 0 V, high pressure RF 110 V and low pressure RF 80 V, both in the positive ion mode. The fragmentor voltage was 380 V for all compounds, while other compound-dependent parameters were as summarized in Table 5.

TABLE 5

Compound-dependent HPLC-MS/MS parameters used for nucleosides quantification.

| Compound | Precursor Ion (m/z) | Product Ion (m/z) | RT (min) | Delta RT (min) | CE (V) | CAE (V) |
|---|---|---|---|---|---|---|
| dA + H | 252 | 136 | 13.78 | 2 | 10 | 4 |
| dT + H | 243 | 127 | 11.07 | 2 | 10 | 4 |
| dT + Na | 265 | 149 | 11.07 | 2 | 10 | 4 |
| dG + H | 268 | 152 | 9.64 | 2 | 10 | 4 |
| dC + H | 228 | 112 | 3.71 | 1.5 | 10 | 4 |
| dC + Na | 250 | 134 | 3.71 | 1.5 | 10 | 4 |
| mdC + H | 242 | 126 | 9.05 | 1.5 | 10 | 4 |
| mdC + Na | 264 | 148 | 9.05 | 1.5 | 10 | 4 |
| hmdC + H | 258 | 142 | 4.34 | 2 | 12 | 4 |
| hmdC + Na | 280 | 164 | 4.34 | 2 | 12 | 4 |
| fdC + H | 256 | 140 | 10.69 | 2 | 8 | 4 |
| fdC + Na | 278 | 162 | 10.69 | 2 | 8 | 4 |
| cadC + H | 272 | 156 | 1.75 | 3 | 12 | 4 |
| cadC + Na | 294 | 178 | 1.75 | 3 | 12 | 4 |
| DHU + H | 231 | 115 | 3.45 | 3 | 10 | 4 |
| DHU + Na | 253 | 137 | 3.45 | 3 | 10 | 4 |

RT: retention time,
CE: collision energy;
CAE: cell accelerator voltage.
All the nucleosides were analyzed in the positive mode.

Expression and Purification of NgTET1 pRSET-A plasmid encoding His-tagged NgTET1 protein (GG739552.1) was designed and purchased from Invitrogen. Protein was expressed in E. coli BL21 (DE3) bacteria and purified as previously described with some modifications (J. E. Pais et al., Biochemical characterization of a Naegleria TET-like oxygenase and its application in single molecule sequencing of 5-methylcytosine. Proc. Natl. Acad. Sci. U.S.A. 112, 4316-4321 (2015), incorporated herein by reference). Briefly, for protein expression bacteria from overnight small-scale culture were grown in LB medium at 37° C. and 200 rpm until OD600 was between 0.7-0.8. Then cultures were cooled down to room temperature and target protein expression was induced with 0.2 mM isopropyl-β-d-1-thiogalactopyranoside (IPTG). Cells were maintained for additional 18 hours at 18° C. and 180 rpm. Subsequently, cells were harvested and re-suspended in the buffer containing 20 mM HEPES (pH 7.5), 500 mM NaCl, 1 mM DTT, 20 mM imidazole, 1 μg/mL leupeptin, 1 μg/mL pepstatin A and 1 mM PMSF. Cells were broken with EmulsiFlex-C5 high-pressure homogenizer, and lysate was clarified by centrifugation for 1 hour at 30,000×g and 4° C. Collected supernatant was loaded on Ni-NTA resins and NgTET1 protein was eluted with buffer containing 20 mM HEPES (pH 7.5), 500 mM imidazole, 2 M NaCl, 1 mM DTT. Collected fractions were then purified on HiLoad 16/60 Sdx 75 (20 mM HEPES pH 7.5, 2 M NaCl, 1 mM DTT). Fractions containing NgTET1 were then collected, buffer exchanged to the buffer containing 20 mM HEPES (pH 7.0), 10 mM NaCl, 1 mM DTT, and loaded on HiTrap HP SP column. Pure protein was eluted with the salt gradient, collected and buffer-exchanged to the final buffer containing 20 mM Tris-Cl (pH 8.0), 150 mM NaCl and 1 mM DTT. Protein was then concentrated up to 130 μM, mixed with glycerol (30% v/v) and aliquots were stored at −80° C.

Expression and Purification of mTET1CD mTET1CD catalytic domain (NM 001253857.2, 4371-6392) with N-terminal Flag-tag was cloned into pcDNA3-Flag between KpnI and BamH1 restriction sites. For protein expression, 1 mg plasmid was transfected into 1 L of Expi293F (Gibco) cell culture at density 1×10$^6$ cells/mL and cells were grown for 48 h at 37° C., 170 rpm and 5% $CO_2$. Subsequently, cells were harvested by centrifugation, re-suspended in the lysis buffer containing 50 mM Tris-Cl pH=7.5, 500 mM NaCl, 1× cOmplete Protease Inhibitor Cocktail (Sigma), 1 mM PMSF, 1% Triton X-100 and incubated on ice for 20 min. Cell lysate was then clarified by centrifugation for 30 min at 30000×g and 4° C. Collected supernatant was purified on ANTI-FLAG M2 Affinity Gel (Sigma) and pure protein was eluted with buffer containing 20 mM HEPES pH=8.0, 150 mM NaCl, 0.1 mg/mL 3× Flag peptide (Sigma), 1× cOmplete Protease Inhibitor Cocktail (Sigma), 1 mM PMSF. Collected fractions were concentrated and buffer-exchanged to the final buffer containing 20 mM HEPES pH=8.0, 150 mM NaCl and 1 mM DTT. Concentrated protein was mixed with glycerol (30% v/v), frozen in liquid nitrogen and aliquots were stored at −80° C. Activity and quality of recombinant mTET1CD was checked by MALDI Mass Spectrometry analysis. Based on this assay, recombinant mTET1CD is fully active and able to catalyze oxidation of 5mC to 5caC. Any significant digestion of tested model oligo was detected by MALDI confirming that protein is free from nucleases.

TET Oxidation

NgTET1 Oxidation. For Tet oxidation of the 222 bp model DNA oligos, 100 ng of 222 bp DNA was incubated in 20 μl solution containing 50 mM MOPs buffer (pH 6.9), 100 mM ammonium iron (II) sulfate, 1 mM a-ketoglutarate, 2 mM ascorbic acid, 1 mM dithiothreitol (DTT), 50 mM NaCl, and 5 μM NgTET for 1 hr at 37° C. After that, 0.4 U of Proteinase K (New England Biolabs) was added to the reaction mixture and incubated for 30 min at 37° C. The product was purified by Zymo-Spin column (Zymo Research) following manufacturer's instruction.

For NgTET1 oxidation of genomic DNA, 500 ng of genomic DNA were incubated in 50 μl solution containing 50 mM MOPS buffer (pH 6.9), 100 mM ammonium iron (II) sulfate, 1 mM a-ketoglutarate, 2 mM ascorbic acid, 1 mM dithiothreitol, 50 mM NaCl, and 5 μM NgTET1 for 1 hour at 37° C. After that, 4 U of Proteinase K (New England Biolabs) were added to the reaction mixture and incubated for 30 min at 37° C. The product was cleaned-up on 1.8× Ampure beads following the manufacturer's instruction.

mTET1 Oxidation. 100 ng of genomic DNA was incubated in 50 μl reaction containing 50 mM HEPES buffer (pH 8.0), 100 μM ammonium iron (II) sulfate, 1 mM a-ketoglutarate, 2 mM ascorbic acid, 1 mM dithiothreitol, 100 mM NaCl, 1.2 mM ATP and 4 μM mTET1CD for 80 min at 37° C. After that, 0.8 U of Proteinase K (New England Biolabs) were added to the reaction mixture and incubated for 1 hour at 50° C. The product was cleaned-up on Bio-Spin P-30 Gel Column (Bio-Rad) and 1.8× Ampure XP beads following the manufacturer's instruction.

Borane Reduction

Pic-$BH_3$ reduction 25 μL of 5 M α-picoline-borane (pic-$BH_3$, Sigma-Aldrich) in MeOH and 5 μL of 3 M sodium acetate solution (pH 5.2, Thermo Fisher) was added into 20 μL DNA sample and incubated at 60° C. for 1 h. The product was purified by Zymo-Spin column (Zymo Research) following manufacturer's instructions for the 222 bp or by Micro Bio-Spin 6 Columns (Bio-Rad) following manufacturer's instruction for the oligos.

Alternatively, 100 mg of 2-picoline-borane (pic-borane, Sigma-Aldrich) was dissolved in 187 µL of DMSO to give around 3.26 M solution. For each reaction, 25 µL of pic-borane solution and 5 µL of 3 M sodium acetate solution (pH 5.2, Thermo Fisher) were added into 20 µL of DNA sample and incubated for 3 hours at 70° C. The product was purified by Zymo-Spin column for genomic DNA or by Micro Bio-Spin 6 Columns (Bio-Rad) for DNA oligos following the manufacturer's instructions.

Pyridine borane reduction. 50-100 ng of oxidised DNA in 35 µL of water were reduced in 50 µL reaction containing 600 mM sodium acetate solution (pH=4.3) and 1 M pyridine borane for 16 hours at 37° C. and 850 rpm in Eppendorf ThermoMixer. The product was purified by Zymo-Spin column.

Single nucleoside pic-borane reaction. 500 µL of 3.26 M 2-picoline-borane (pic-borane, Sigma-Aldrich) in MeOH and 500 µL of 3 M sodium acetate solution (pH 5.2, Thermo Fisher) were added into 10 mg of 2'-deoxycytidine-5-carboxylic acid sodium salt (Berry&Associates). The mixture was stirred for 1 hour at 60° C. The product was purified by HPLC to give pure compound as white foam. High resolution MS (Q-TOF) m/z [M+Na]+ calculated for $C_9H_{14}N_2O_5Na$: 253.0800; found: 253.0789.

5hmC Blocking

5hmC blocking was performed in 20 µl solution containing 50 mM HEPES buffer (pH 8), 25 mM $MgCl_2$, 200 µM uridine diphosphoglucose (UDP-Glc, New England Biolabs), and 10 U βGT (Thermo Fisher), and 10 µM 5hmC DNA oligo for 1 hr at 37° C. The product was purified by Micro Bio-Spin 6 Columns (Bio-Rad) following manufacturer's instruction.

5fC Blocking

5fC blocking was performed in 100 mM IVIES buffer (pH 5.0), 10 mM O-ethylhydroxylamine (Sigma-Aldrich), and 10 µM 5fC DNA oligo for 2 hours at 37° C. The product was purified by Micro Bio-Spin 6 Columns (Bio-Rad) following manufacturer's instruction.

5caC Blocking

5caC blocking was performed in 75 mM MES buffer (pH 5.0), 20 mM N-hydroxysuccinimide (NHS, Sigma-Aldrich), 20 mM 1-(3-dimethylaminopropyl)-3-ethylcarbodiimide hydrochloride (EDC, Fluorochem), and 10 µM 5caC DNA oligo at 37° C. for 0.5 h. The buffer was then exchanged to 100 mM sodium phosphate (pH 7.5), 150 mM NaCl using Micro Bio-Spin 6 Columns (Bio-Rad) following manufacturer's instructions. 10 mM ethylamine (Sigma-Aldrich) was added to the oligo and incubated for 1 hour at 37° C. The product was purified by Micro Bio-Spin 6 Columns (Bio-Rad) following manufacturer's instructions.

5hmC Oxidation

46 µL of 5hmC DNA oligo was denatured with 2.5 µL of 1 M NaOH for 30 min at 37° C. in a shaking incubator, then oxidized with 1.5 µL of solution containing 50 mM NaOH and 15 mM potassium perruthenate ($KRuO_4$, Sigma-Aldrich) for 1 hour on ice. The product was purified by Micro Bio-Spin 6 Columns following manufacturer's instructions.

Validation of TAPS Conversion with TaqαI Assay

5mC conversion after TAPS was tested by PCR amplification of a target region which contains TaqαI restriction site (TCGA) and subsequent TaqαI digestion. For example, 5mC conversion in our TAPS libraries can be tested based on 194 bp amplicon containing single TaqαI restriction site that is amplified from CpG methylated lambda DNA spike-in control. PCR product amplified from the 194 bp amplicon is digested with TaqαI restriction enzyme and digestion product is checked on 2% agarose gel. PCR product amplified on unconverted control DNA is digested by TaqαI and shows two bands on the gel. In TAPS-converted sample restriction site is lost due to C-to-T transition, so the 194 bp amplicon would remain intact. Overall conversion level can be assessed based on digested and undigested gel bands quantification and for successful TAPS samples should be higher than 95%.

Briefly, the converted DNA sample was PCR amplified by Taq DNA Polymerase (New England Biolabs) with corresponding primers. The PCR product was incubated with 4 units of TaqαI restriction enzyme (New England Biolabs) in 1× CutSmart buffer (New England Biolabs) for 30 min at 65° C. and checked by 2% agarose gel electrophoresis.

Quantitative Polymerase Chain Reaction (qPCR)

Figure 11:
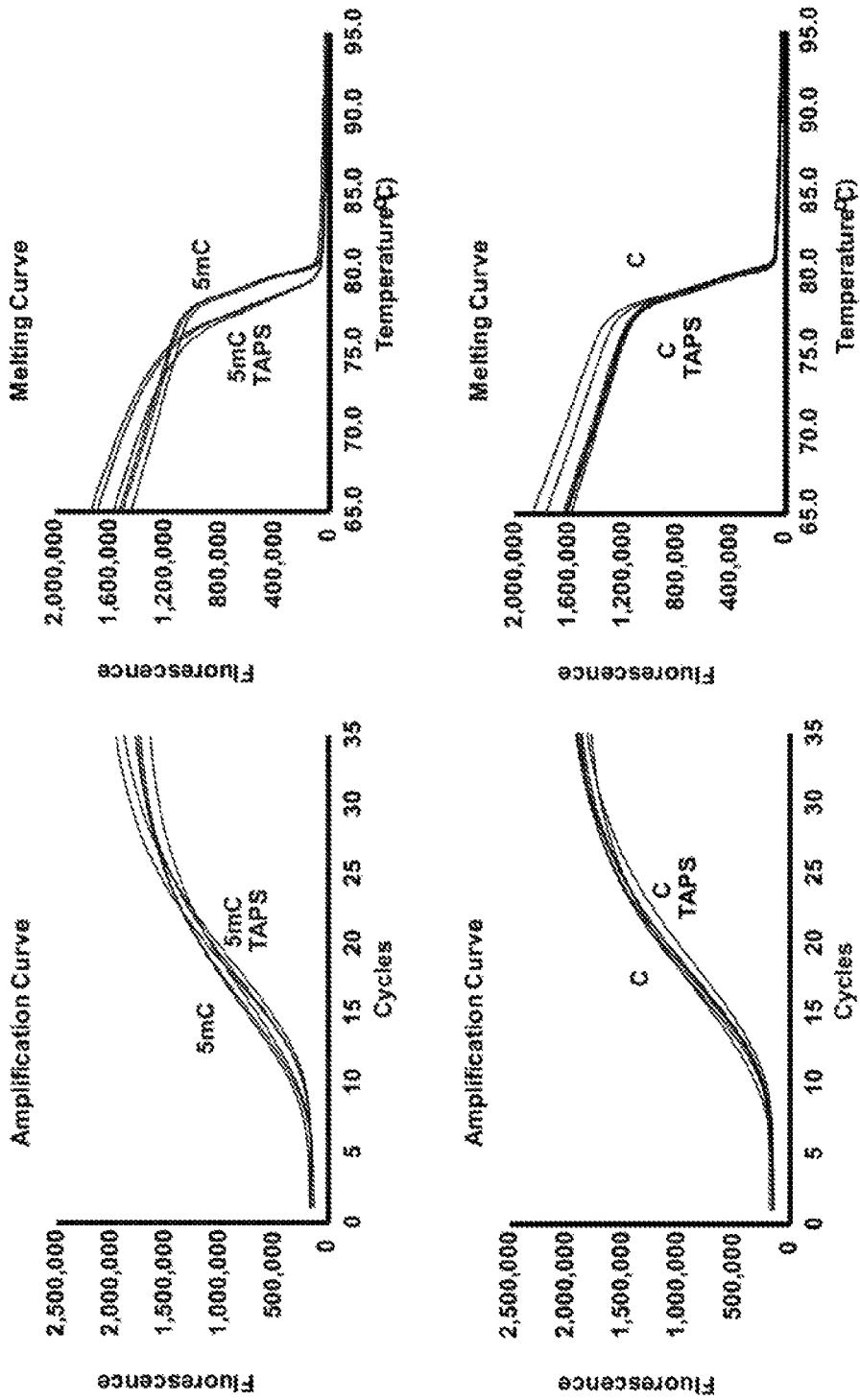
FIG. 11. Comparison of amplification curves and melting curves between model DNAs before and after TAPS. qPCR assay showed minor difference on model DNAs before and after TAPS in amplification curves. Melting curve of methylated DNA (5mC) shifted to lower temperature after TAPS indicated possible Tm-decreasing C-to-T transition while there was no shift for unmethylated DNA (C).

For comparison of amplification curves and melting curves between model DNAs before and after TAPS (FIG. 11), 1 ng of DNA sample was added into 19 µL of PCR master mix containing 1× LightCycler 480 High Resolution Melting Master Mix (Roche Diagnostics Corporation), 250 nM of primers FW-CCTGATGAAACAAGCATGTC and RV-CATTACTCACTTCCCCACTT and 3 mM of $MgSO_4$. For PCR amplification, an initial denaturation step was performed for 10 min at 95° C., followed by 40 cycles of 5 sec denaturation at 95° C., 5 sec annealing at customized annealing temperature and 5 sec elongation at 72° C. The final step included 1 min at 95° C., 1 min at 70° C. and a melting curve (0.02° C. step increments, 5 sec hold before each acquisition) from 65° C. to 95° C.

For other assays, qPCR was performed by adding the required amount of DNA sample into 19 µL of PCR master mix containing 1× Fast SYBR Green Master Mix (Thermo Fisher), 200 nM of forward and reverse primers. For PCR amplification, an initial denaturation step was performed for 20 sec at 95° C., followed by 40 cycles of 3 s denaturation at 95° C., 20 s annealing and elongation at 60° C.

Validation of $C^mCGG$ Methylation Level in mESC gDNA with HpaII-qPCR Assay.

1 µg mESC gDNA was incubated with 50 units of HpaII (NEB, 50 units/µL) and 1× CutSmart buffer in 50 µL reaction for 16 hours at 37° C. No HpaII was added for control reaction. 1 µL Proteinase K was added to the reaction and incubated at 40° C. for 30 minutes followed by inactivation of Proteinase K for 10 minutes at 95° C. Ct value of HpaII digested sample or control sample was measured by qPCR assay as above with corresponding primer sets for specific CCGG positions (listed in Table 9).

Sanger Sequencing

The PCR product was purified by Exonuclease I and Shrimp Alkaline Phosphatase (New England Biolabs) or Zymo-Spin column and processed for Sanger sequencing.

DNA Damage Test on Fragments with Different Length.

mESC genomic DNA was spiked-in with 0.5% of CpG methylated lambda DNA and left unfragmented or sonicated with Covaris M220 instrument and size-selected to 500-1 kb or 1 kb-3 kb on Ampure XP beads. 200 ng of DNA were single-oxidised with mTET1CD and reduced with Pyridine borane complex as described above or converted with Epi-Tect Bisulfite Kit (Qiagen) according to manufacturer's protocol. 10 ng of DNA before and after TAPS and Bisulfite conversion were run on 1% agarose gel. To visualize bisulfite converted gel was cooled down for 10 min samples in ice bath. 5mC conversion in TAPS samples was tested by TaqαI digestion assay as described above.

mESCs Culture and Isolation of Genomic DNA

Mouse ESCs (mESCs) E14 were cultured on gelatin-coated plates in Dulbecco's Modified Eagle Medium (DMEM) (Invitrogen) supplemented with 15% FBS (Gibco), 2 mM L-glutamine (Gibco), 1% non-essential amino acids (Gibco), 1% penicillin/streptavidin (Gibco), 0.1 mM β-mercaptoethanol (Sigma), 1000 units/mL LIF (Millipore), 1 μM PD0325901 (Stemgent), and 3 μM CHIR99021 (Stemgent). Cultures were maintained at 37° C. and 5% $CO_2$ and passaged every 2 days.

For isolation of genomic DNA, cells were harvested by centrifugation for 5 min at 1000×g and room temperature. DNA was extracted with Quick-DNA Plus kit (Zymo Research) according to manufacturer's protocol.

Preparation of mESC gDNA for TAPS and WGBS.

For whole-genome bisulfite sequencing (WGBS), mESC gDNA was spiked-in with 0.5% of unmethylated lambda DNA. For whole-genome TAPS, mESC gDNA was spiked-in with 0.5% of methylated lambda DNA and 0.025% of unmodified 2 kb spike-in control. DNA samples were fragmented by Covaris M220 instrument and size-selected to 200-400 bp on Ampure XP beads. DNA for TAPS was additionally spiked-in with 0.25% of N5mCNN and N5hmCNN control oligo after size-selection with Ampure XP beads.

Whole Genome Bisulfite Sequencing

For Whole Genome Bisulfite Sequencing (WGBS), 200 ng of fragmented mESC gDNA spiked-in with 0.5% of unmethylated bacteriophage lambda DNA was used. End-repaired and A-tailing reaction and ligation of methylated adapter (NextFlex) were prepared with KAPA HyperPrep kit (Kapa Biosystems) according to manufacturer's protocol. Subsequently, DNA underwent bisulfite conversion with EpiTect Bisulfite Kit (Qiagen) according to Illumina's protocol. Final library was amplified with KAPA Hifi Uracil Plus Polymerase (Kapa Biosystems) for 6 cycles and cleaned-up on 1× Ampure beads. WGBS sequencing library was paired-end 80 bp sequenced on a NextSeq 500 sequencer (Illumina) using a NextSeq High Output kit with 15% PhiX control library spike-in.

Whole-Genome TAPS

For whole genome TAPS, 100 ng of fragmented mESC gDNA spiked-in with 0.5% of methylated lambda DNA and 0.025% of unmodified 2 kb spike-in control were used. End-repair and A-tailing reaction and ligation of Illumina Multiplexing adapters were prepared with KAPA HyperPrep kit according to manufacturer's protocol. Ligated DNA was oxidized with mTET1CD twice and then reduced with pyridine borane according to the protocols described above. Final sequencing library was amplified with KAPA Hifi Uracil Plus Polymerase for 5 cycles and cleaned-up on 1× Ampure beads. Whole-genome TAPS sequencing library was paired-end 80 bp sequenced on a NextSeq 500 sequencer (Illumina) using one NextSeq High Output kit with 1% PhiX control library spike-in.

Low-Input Whole-Genome TAPS with dsDNA Library Preparation Kits mESC gDNA prepared as described above for whole-genome TAPS was used for low-input whole-genome TAPS. Briefly, samples containing 100 ng, 10 ng, and 1 ng of mESC gDNA were oxidized with NgTET1 once according to the protocol described above. End-repaired and A-tailing reaction and ligation were performed with NEBNext Ultra II (New England Biolabs) or KAPA HyperPrep kit according to manufacturer's protocol. Subsequently DNA underwent pic-borane reaction as described above. Converted libraries were amplified with KAPA Hifi Uracil Plus Polymerase and cleaned-up on 1× Ampure beads.

Low-Input Whole-Genome TAPS with ssDNA Library Preparation Kit mESC gDNA prepared as described above for whole-genome TAPS was used for low-input whole-genome TAPS. Briefly, samples containing 100 ng, 10 ng, 1 ng, 100 pg, and 10 pg of mESC gDNA were oxidized with NgTET1 once and reduced with pic-borane as described above. Sequencing libraries were prepared with Accel-NGS Methyl-Seq DNA Library Kit (Swift Biosciences) according to manufacturer's protocol. Final libraries were amplified with KAPA Hifi Uracil Plus Polymerase for 6 cycles (100 ng), 9 cycles (10 ng), 13 cycles (1 ng), 16 cycles (100 pg), and 21 cycles (10 pg) and cleaned-up on 0.85× Ampure beads.

In other experiments, mESC gDNA prepared as described above for whole-genome TAPS were used for low-input whole-genome TAPS. Briefly, samples containing 100 ng, 10 ng, and 1 ng of mESC gDNA were used for End-repaired and A-tailing reaction and ligated to Illumina Multiplexing adaptors with KAPA HyperPrep kit according to manufacturer's protocol. Ligated samples were then oxidized with mTET1CD once and then reduced with pyridine borane according to the protocols described above. Converted libraries were amplified with KAPA Hifi Uracil Plus Polymerase for 5 cycles (100 ng), 8 cycles (10 ng), and 13 cycles (1 ng) and cleaned-up on 1× Ampure XP beads.

Cell-Free DNA TAPS

Cell-free DNA TAPS samples were prepared from 10 ng and 1 ng of cell-free DNA sample. Briefly, samples were oxidized with NgTET1 once and reduced with pic-borane as described above. Sequencing libraries were prepared with Accel-NGS Methyl-Seq DNA Library Kit (Swift Biosciences) according to manufacturer's protocol. Final libraries were amplified with KAPA Hifi Uracil Plus Polymerase for 9 cycles (10 ng) and 13 cycles (1 ng) and cleaned-up on 0.85× Ampure beads.

In other experiments, cell-free DNA TAPS samples were prepared from 10 ng and 1 ng of cell-free DNA sample as described above for whole-genome TAPS. Briefly, cell-free DNA samples were used for End-repaired and A-tailing reaction and ligated to Illumina Multiplexing adaptors with KAPA HyperPrep kit according to manufacturer's protocol. Ligated samples were then oxidized with mTET1CD once and then reduced with pyridine borane according to the protocols described above. Converted libraries were amplified with KAPA Hifi Uracil Plus Polymerase for 7 cycles (10 ng), and 13 cycles (1 ng) and cleaned-up on 1× Ampure XP beads.

WGBS Data Processing

Paired-end reads were download as FASTQ from Illumina BaseSpace and subsequently quality-trimmed with Trim Galore! v0.4.4 (https://www.bioinformatics.babraham.ac.uk/projects/trim_galore/). Read pairs where at least one read was shorter than 35 bp after trimming were removed. Trimmed reads were mapped to a genome combining the mm9 version of the mouse genome, lambda phage and PhiX (sequence from Illumina iGENOMES) using Bismark v0.19 using --no_overlap option (F. Krueger, S. R. Andrews, Bismark: a flexible aligner and methylation caller for Bisulfite-Seq applications. *Bioinformatics* 27, 1571-1572 (2011), incorporated herein by reference). The 'three-C' filter was used to remove reads with excessive non-conversion rates. PCR duplicates were called using Picard v1.119 (http://broadinstitute.github.io/picard/) MarkDuplicates. Regions known to be prone to mapping artefacts were downloaded (https://sites.google.com/site/anshulkundaje/projects/blacklists) and excluded from further analysis (E. P.

Consortium, An integrated encyclopedia of DNA elements in the human genome. *Nature* 489, 57-74 (2012), incorporated herein by reference).

TAPS Data Pre-Processing

Paired-end reads were downloaded from Illumina BaseSpace and subsequently quality-trimmed with Trim Galore! v0.4.4. Read pairs where at least one read was shorter than 35 bp after trimming were removed. Trimmed reads were mapped to a genome combining spike-in sequences, lambda phage and the mm9 version of the mouse genome using BWA mem v.0.7.15 (H. Li, R. Durbin, Fast and accurate short read alignment with Burrows-Wheeler transform. *Bioinformatics* 25, 1754-1760 (2009), incorporated herein by reference) with default parameters. Regions known to be prone to mapping artefacts were downloaded (https://sites-.google.com/site/anshulkundaje/projects/blacklists) and excluded from further analysis (E. P. Consortium, *Nature* 489, 57-74 (2012)).

Detection of Converted Bases in TAPS

Aligned reads were split into original top (OT) and original bottom (OB) strands using a custom python3 script (MF-filter.py). PCR duplicates were then removed with Picard MarkDuplicates on OT and OB separately. Overlapping segments in read pairs were removed using BamUtil clipOverlap (https://github.com/statgen/bamUtil) on the deduplicated, mapped OT and OB reads separately. Modified bases were then detected using samtools mpileup and a custom python3 script (MF-caller_MOD.py).

Sequencing Quality Analysis of TAPS and WGBS

Quality score statistics per nucleotide type were extracted from original FASTQ files as downloaded from Illumina BaseSpace with a python3 script (MF-phredder.py).

Coverage Analysis of TAPS and WGBS

Per-base genome coverage files were generated with Bedtools v2.25 genomecov (A. R. Quinlan, I. M. Hall, BEDTools: a flexible suite of utilities for comparing genomic features. *Bioinformatics* 26, 841-842 (2010), incorporated herein by reference). To compare the relative coverage distributions between TAPS and WGBS, TAPS reads were subsampled to the corresponding coverage median in WGBS using the -s option of samtools view. In the analyses comparing coverage in WGBS and subsampled TAPS, clipOverlap was used on both TAPS and WGBS bam files.

Analysis of Cytosine Modifications Measured by TAPS and WGBS

The fraction of modified reads per base was calculated from Bismark output, and the output of MF-caller_MOD.py, respectively. Intersections were performed using Bedtools intersect, and statistical analyses and figures were generated in R and Matlab. Genomic regions were visualized using IGV v2.4.6 (J. T. Robinson et al., Integrative genomics viewer. *Nat. Biotechnol.* 29, 24-26 (2011), incorporated herein by reference). To plot the coverage and modification levels around CGIs, all CGI coordinates for mm9 were downloaded from the UCSC genome browser, binned into 20 windows, and extended by up to 50 windows of size 80 bp on both sides (as long as they did not reach half the distance to the next CGI). Average modification levels (in CpGs) and coverage (in all bases, both strands) in each bin were computed using Bedtools map. The values for each bin were again averaged and subsequently plotted in Matlab.

Data Processing Time Simulation

Synthetic pair-end sequencing reads were simulated using ART42 based on the lambda phage genome (with parameters -p -ss NS50 --errfree --minQ 15 -k 0 -nf 0-l 75 -c 1000000 -m 240 -s 0 -ir 0 -ir2 0 -dr 0 -dr2 0 -sam -rs 10). 50% of all CpG positions were subsequently marked as modified and two libraries were produced, either as TAPS (convert modified bases) or as WGBS (convert unmodified bases), using a custom python3 script. The reads were then processed following the pipeline used for each of the methods in the paper. Processing time was measured with Linux command time. All steps of the analysis were performed in single-threaded mode on one Intel Xeon CPU with 250 GB of memory.

Results and Discussion

Figure 2:
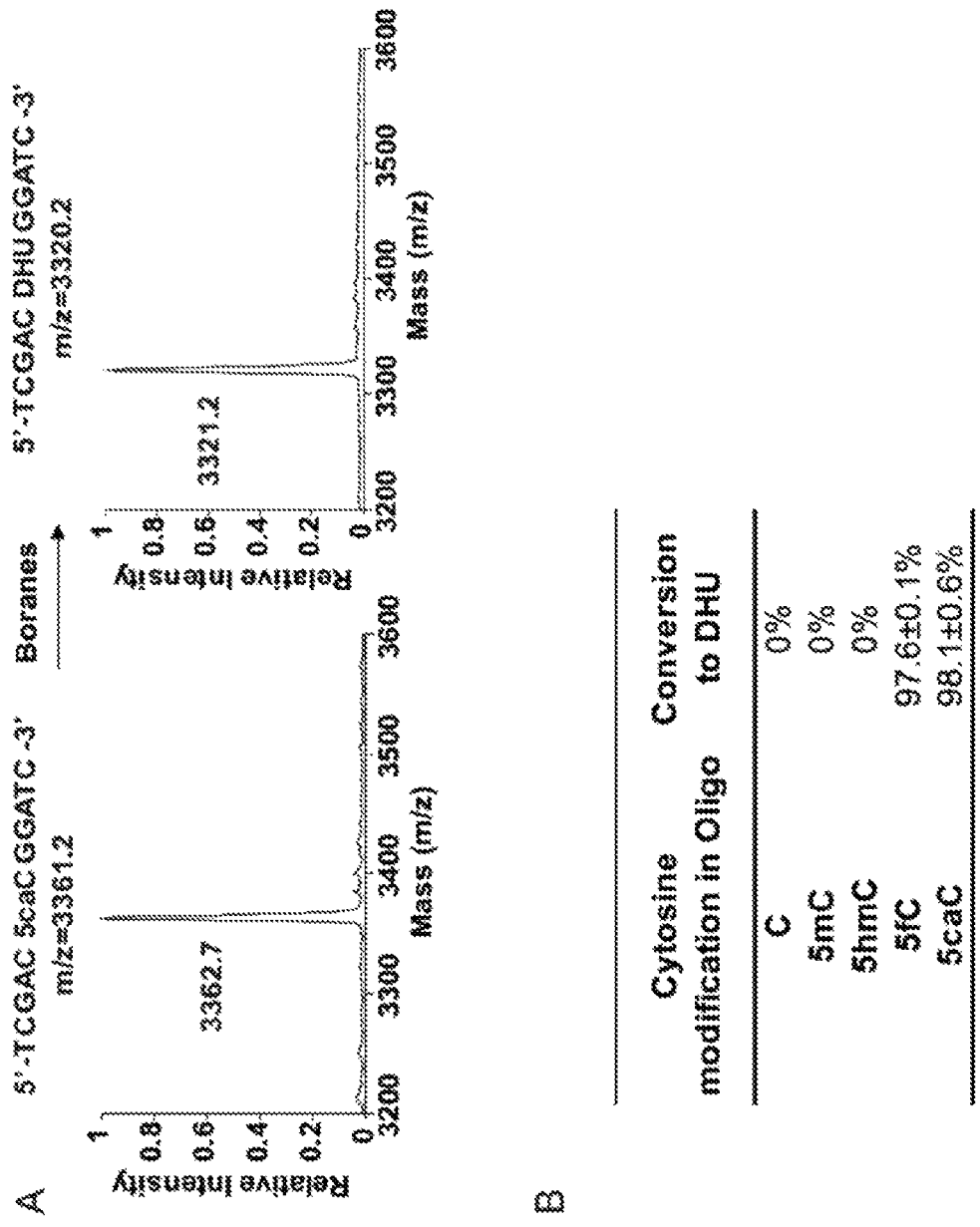
FIG. 2A-B. Pic-borane reaction on DNA oligos. (A) MALDI characterization of 5caC-containing 11mer model DNA treated with pic-borane. Calculated mass (m/z) shown above each graph, observed mass shown to the left of the peak. (B) The conversion rates of dC and various cytosine derivatives were quantified by HPLC-MS/MS. Data shown as mean±SD of three replicates.
Figure 3:
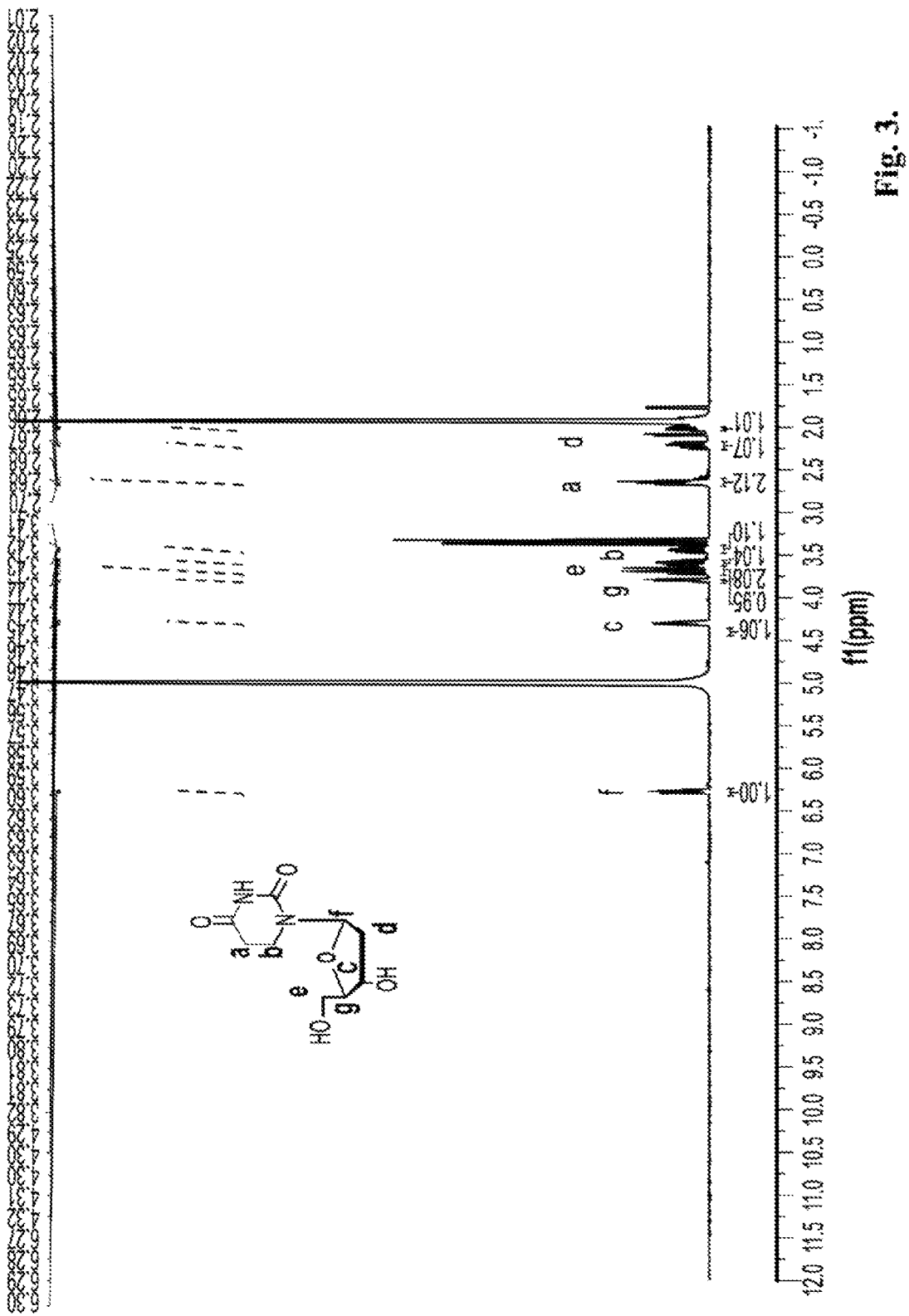
FIG. 3A-B. Single nucleoside pic-borane reaction. $^1$H and $^{13}$C NMR results were in accordance with previous report on 2'-deoxy-5,6-dihydrouridine (I. Aparici-Espert et al., J. Org. Chem. 81, 4031-4038 (2016)). (A) $^1$H NMR (MeOH-d$_4$, 400 MHz) chart of the single nucleoside pic-borane reaction product. δ ppm: 6.28 (t, 1H, J=7 Hz), 4.30 (m, 1H), 3.81 (m, 1H), 3.63 (m, 2H), 3.46 (m, 2H), 2.65 (t, 2H, J=6 Hz), 2.20 (m, 1H), 2.03 (m, 1H). (B) $^{13}$C NMR (MeOH-d$_4$, 400 MHz) chart of the single nucleoside pic-borane reaction product. δ ppm: 171.56 (CO), 153.54 (CO), 85.97 (CH), 83.86 (CH), 70.99 (CH), 61.92 (CH$_2$), 36.04 (CH$_2$), 35.46 (CH$_2$), 30.49 (CH$_2$).
Figure 3:
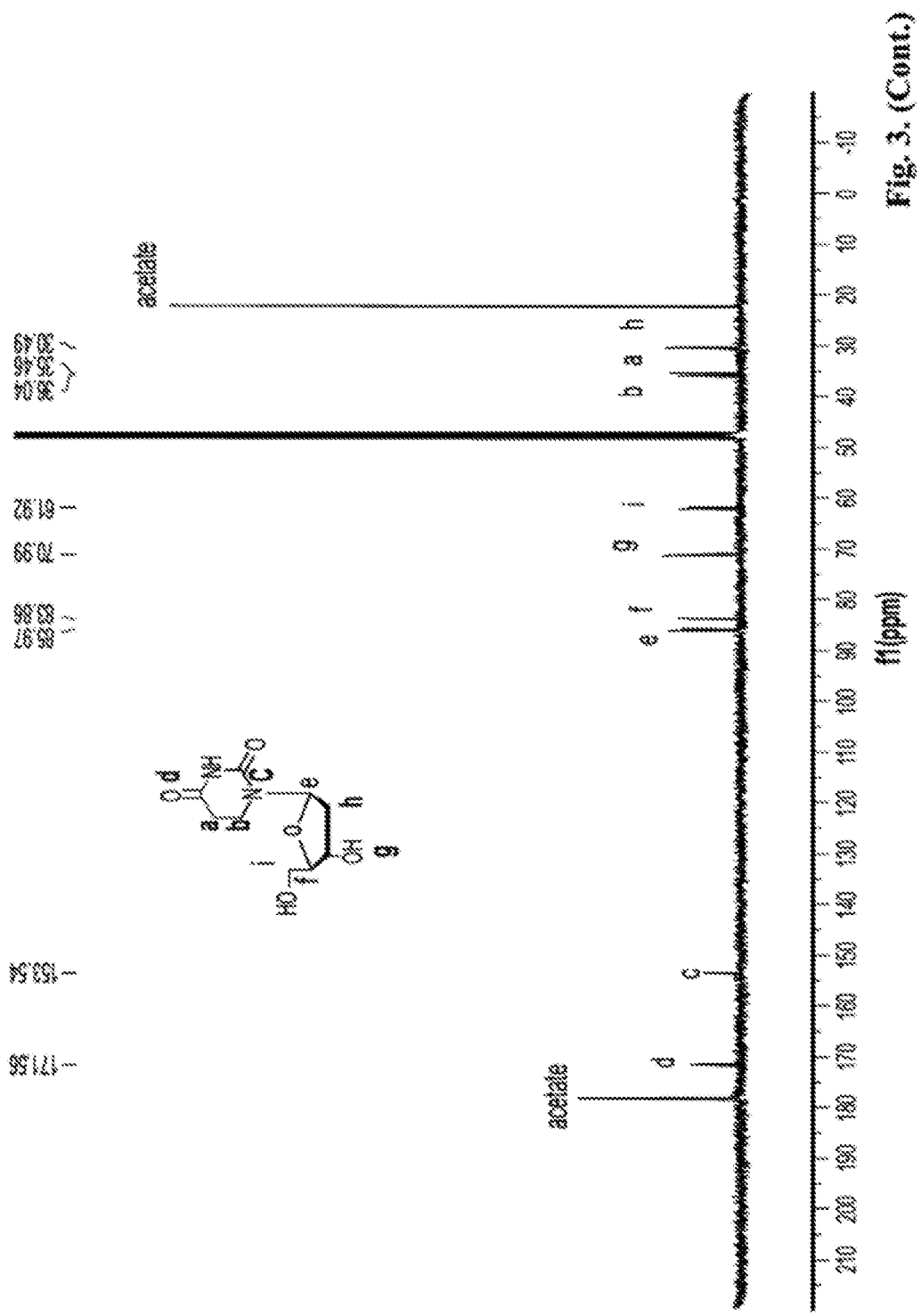
Figure 4:
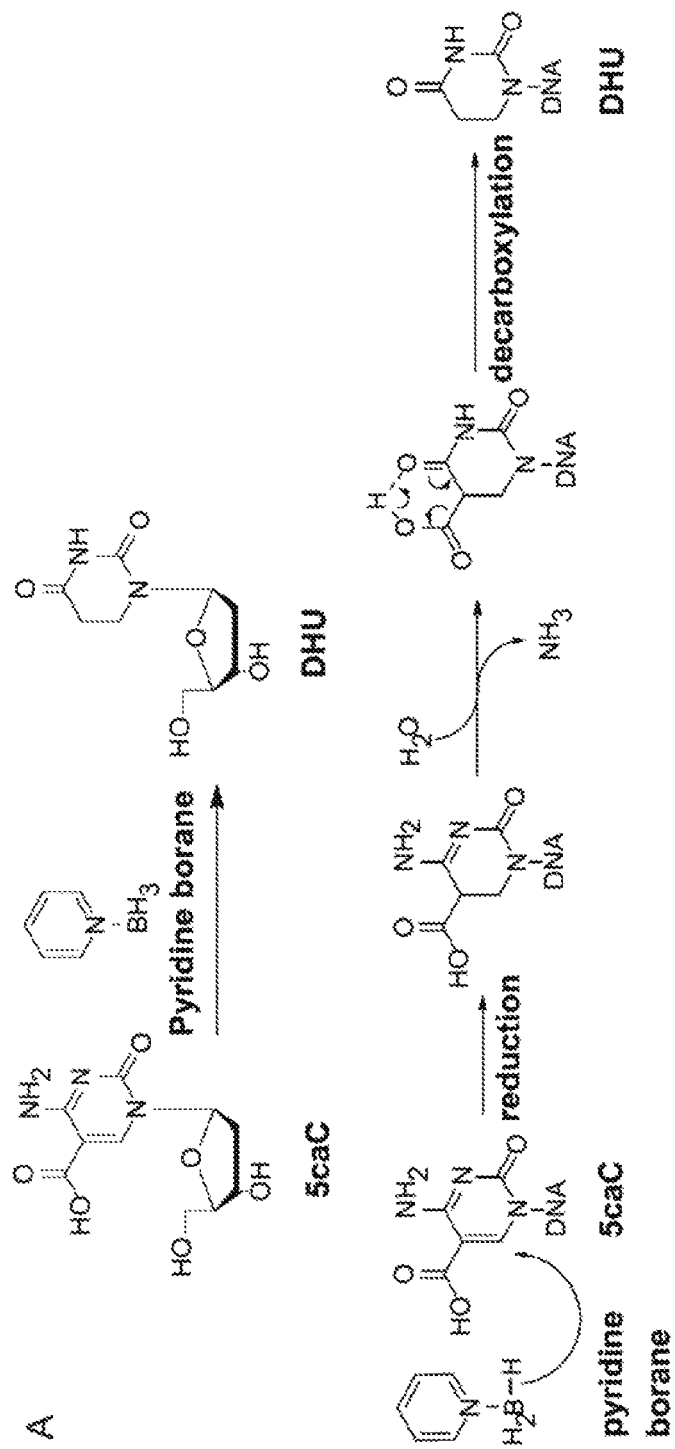
FIG. 4A-B. A diagram showing (A) borane conversion of 5caC to DHU and a proposed mechanism for borane reaction of 5caC to DHU; and (B) borane conversion of 5fC to DHU and a proposed mechanism for borane reaction of 5fC to DHU.
Figure 4:
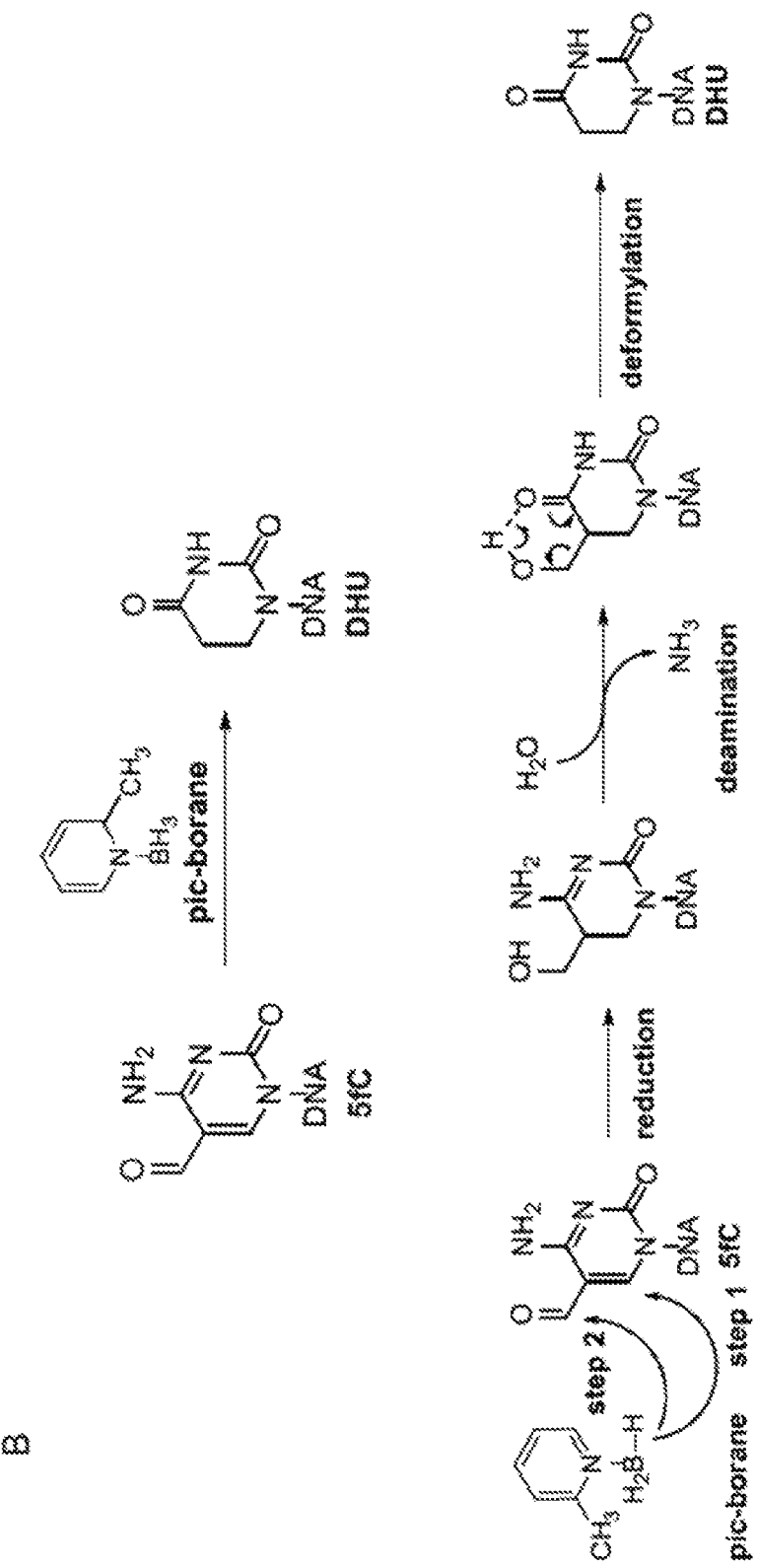

It was discovered that pic-$BH_3$ can readily convert 5fC and 5caC to DHU by a previously unknown reductive decarboxylation/deamination reaction (FIG. 4). The reaction was shown to be quantitative both in single nucleoside and in oligonucleotides using MALDI (FIGS. 2-3, and 6-7).

An 11mer 5caC-containing DNA oligo was used as a model to screen chemicals that could react with 5caC, as monitored by matrix-assisted laser desorption/ionization mass spectroscopy (MALDI). Certain borane-containing compounds were found to efficiently react with the 5caC oligo, resulting in a molecular weight reduction of 41 Da (FIGS. 1 and 2). Pyridine borane and its derivative 2-picoline borane (pic-borane) were selected for further study as they are commercially available and environmentally benign reducing agents.

Figure 6:
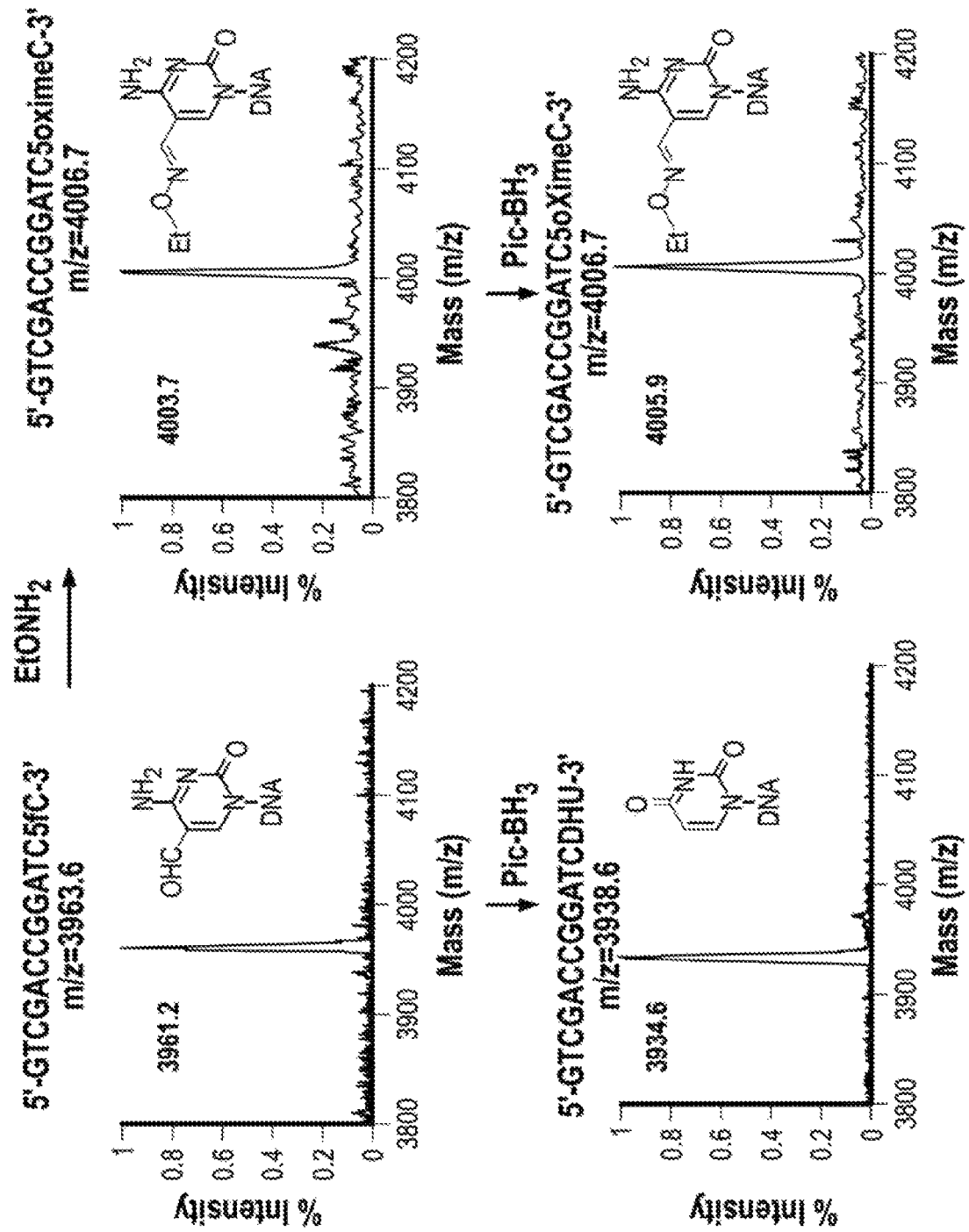
FIG. 6. MALDI characterization of 5fC and 5caC containing model DNA oligos treated by pic-borane with or without blocking 5fC and 5caC. 5fC and 5caC are converted to dihydrouracil (DHU) with pic-BH$_3$. 5fC was blocked by hydroxylamine derivatives such as O-ethylhydroxylamine (EtONH$_2$) which would become oxime and resist pic-borane conversion. 5caC was blocked by ethylamine via EDC conjugation and converted to amide which blocks conversion by pic-borane. Calculated MS (m/z) shown above each graph, observed MS shown to the left of the peak.
Figure 6:
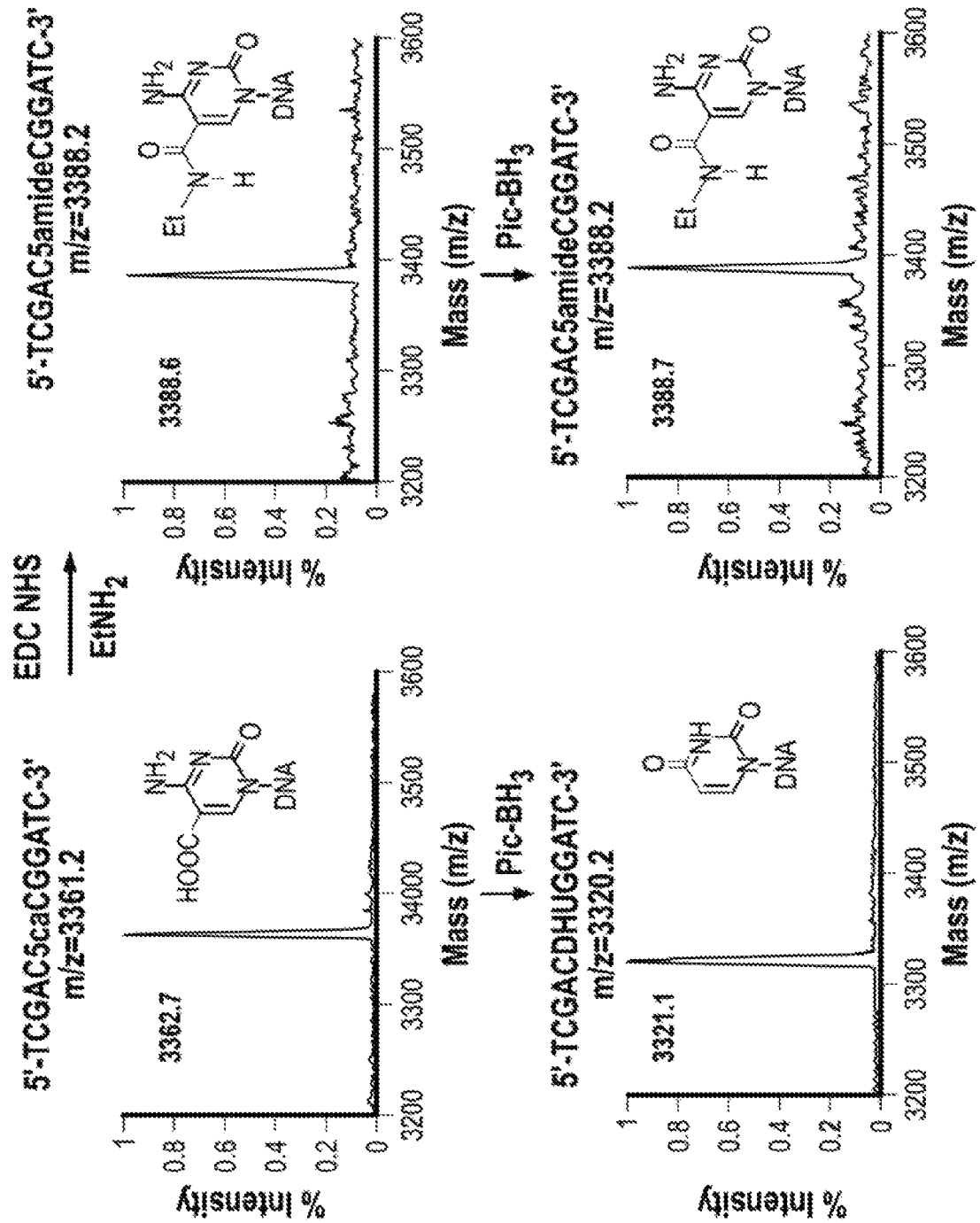

The reaction on a single 5caC nucleoside was repeated and confirmed that pyridine borane and pic-borane convert 5caC to dihydrouracil (DHU) (FIGS. 3, 4B). Interestingly, pyridine borane and pic-borane was found to also convert 5fC to DHU through an apparent reductive decarboxylation/deamination mechanism (FIGS. 4C and 6). The detailed mechanism of both reactions remains to be defined. Quantitative analysis of the borane reaction on the DNA oligo by HPLC-MS/MS confirms that pic-borane converts 5caC and 5fC to DHU with around 98% efficiency and has no activity against unmethylated cytosine, 5mC or 5hmC (FIG. 2B).

As a uracil derivative, DHU can be recognized by both DNA and RNA polymerases as thymine. Therefore, borane reduction can be used to induce both 5caC-to-T and 5fC-to-T transitions, and can be used for base-resolution sequencing of 5fC and 5caC, which we termed Pyridine borane Sequencing ("PS") (Table 6). The borane reduction of 5fC and 5caC to T can be blocked through hydroxylamine conjugation (C. X. Song et al., Genome-wide profiling of 5-formylcytosine reveals its roles in epigenetic priming. *Cell* 153, 678-691 (2013), incorporated herein by reference) and EDC coupling (X. Lu et al., Chemical modification-assisted bisulfite sequencing (CAB-Seq) for 5-carboxyl cytosine detection in DNA. *J. Am. Chem. Soc.* 135, 9315-9317 (2013), incorporated herein by reference), respectively (FIG. 6). This blocking allows PS to be used to sequence 5fC or 5caC specifically (Table 6).

TABLE 6

Comparison of BS and related methods versus PS for 5 fC and 5 caC sequencing.

| Base | BS | fCAB-Seq/ redBS-Seq | caCAB-Seq | fC-CET | PS | PS with 5 fC blocking | PS with 5 caC blocking |
|---|---|---|---|---|---|---|---|
| C | T | T | T | C | C | C | C |
| 5 mC | C | C | C | C | C | C | C |
| 5 hmC | C | C | C | C | C | C | C |
| 5 fC | T | C | T | T | T | C | T |
| 5 caC | T | T | C | C | T | T | C |

Figure 5:
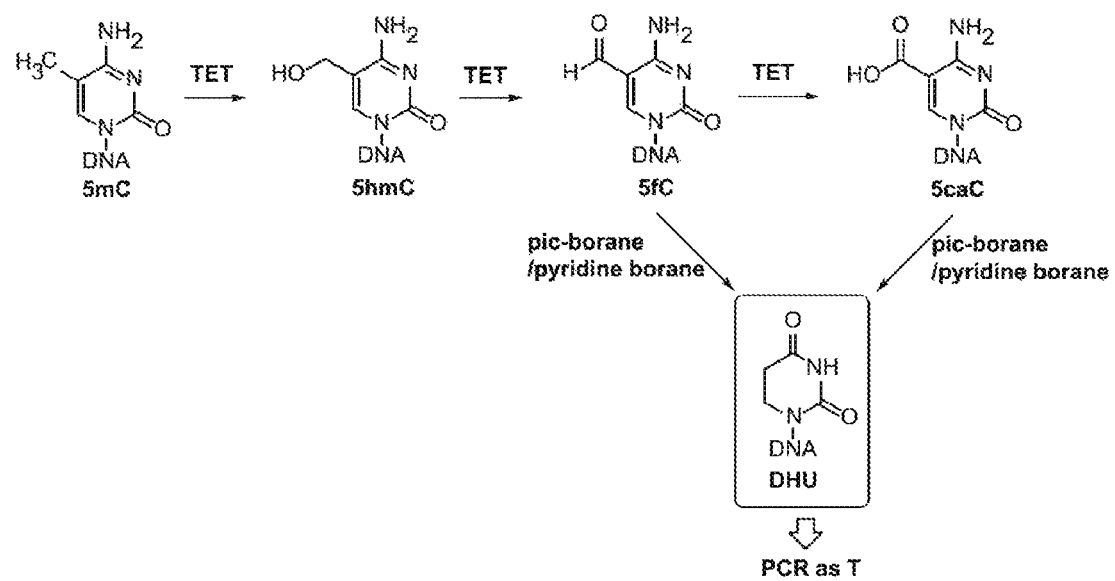
FIG. 5A-B. (A) Diagram showing that the TAPS method converts both 5mC and 5hmC to DHU, which upon replication acts as thymine. (B) Overview of the TAPS, TAPSβ, and CAPS methods.
Figure 5:
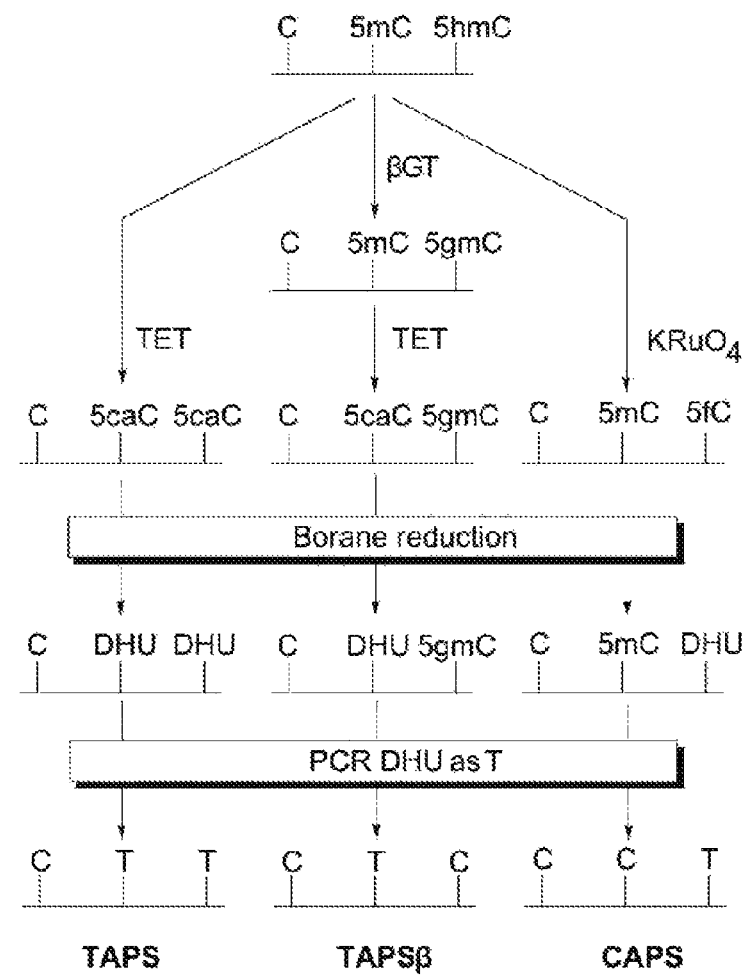

Furthermore, TET enzymes can be used to oxidize 5mC and 5hmC to 5caC, and then subject 5caC to borane reduction in a process herein called TET-Assisted Pyridine borane Sequencing ("TAPS") (FIG. 5A-B, Table 1). TAPS can induce a C-to-T transition of 5mC and 5hmC, and therefore can be used for base-resolution detection of 5mC and 5hmC.

Figure 7:
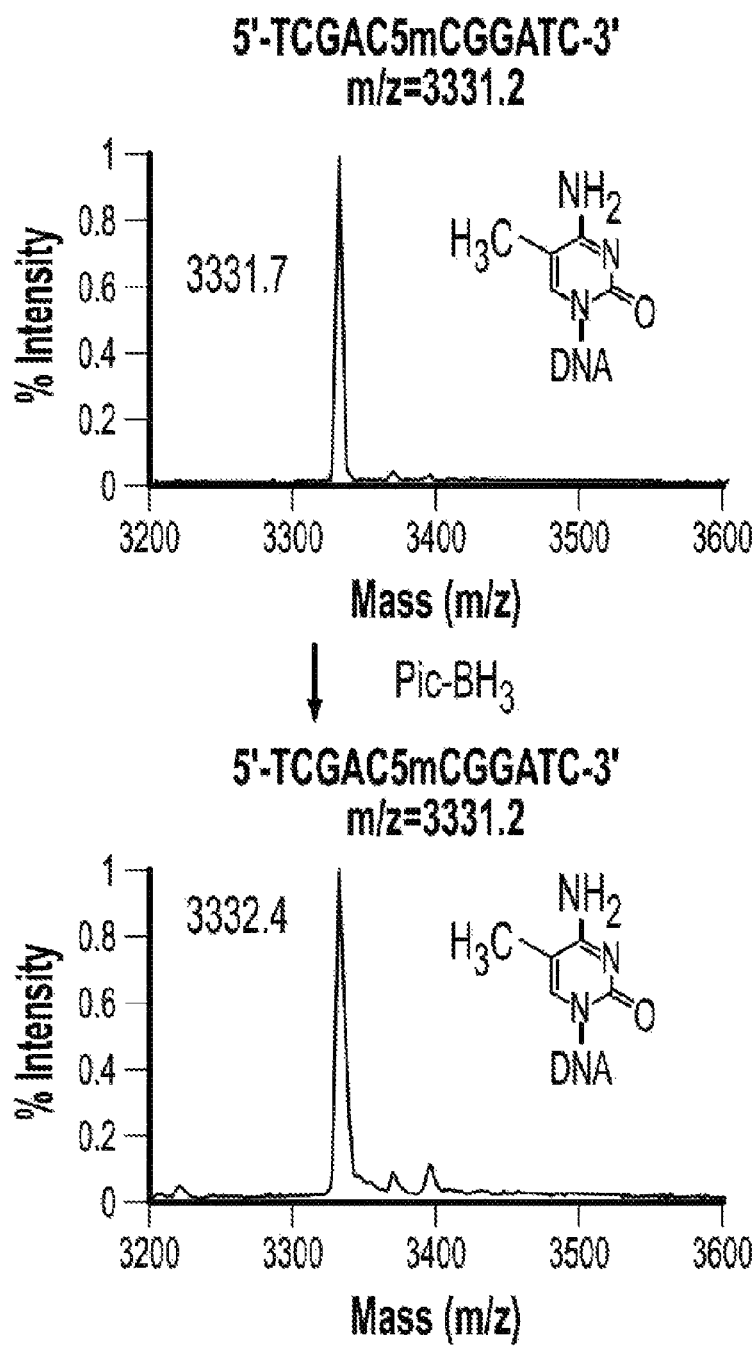
FIG. 7. MALDI characterization of 5mC and 5hmC containing model DNA oligos treated by KRuO$_4$ and pic-borane with or without blocking of 5hmC. 5hmC could be blocked by βGT with glucose and converted to 5gmC. 5mC, 5hmC and 5gmC could not be converted by pic-borane. 5hmC could be oxidized by KRuO$_4$ to 5fC, and then converted to DHU by pic-borane. Calculated MS (m/z) shown above each graph, observed MS shown to the left of the peak.
Figure 7:
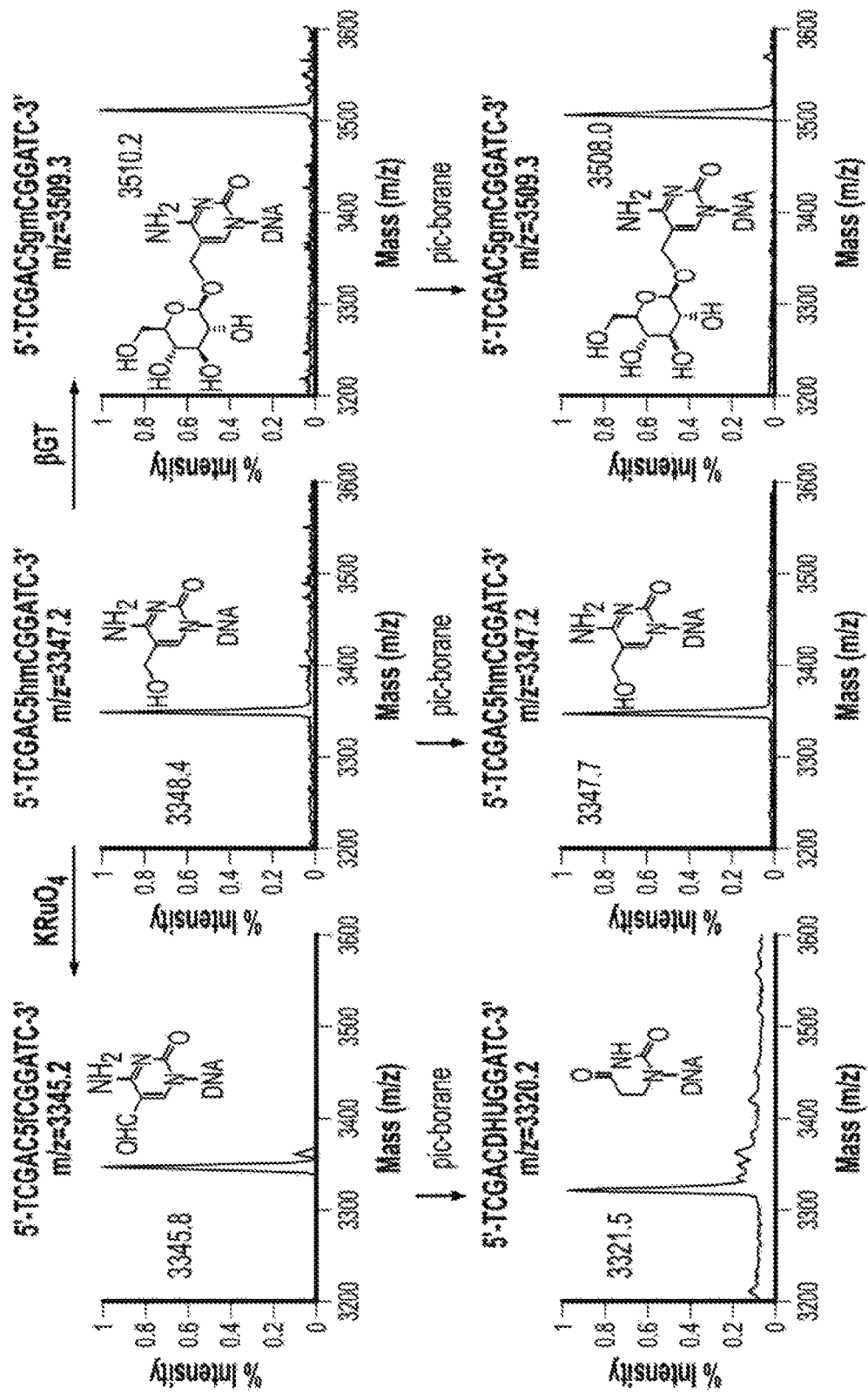

In addition, β-glucosyltransferase (βGT) can label 5hmC with glucose and thereby protect it from TET oxidation (M. Yu et al., Base-resolution analysis of 5-hydroxymethylcytosine in the mammalian genome. Cell 149, 1368-1380 (2012)) and borane reduction (FIG. 7), enabling the selective sequencing of only 5mC, in a process referred to herein as TAPSβ (FIG. 5B, Table 1). 5hmC sites can then be deduced by subtraction of TAPSβ from TAPS measurements. Alternatively, potassium perruthenate ($KRuO_4$), a reagent previously used in oxidative bisulfite sequencing (oxBS) (M. J. Booth et al., Quantitative Sequencing of 5-Methylcytosine and 5-Hydroxymethylcytosine at Single-Base Resolution. Science 336, 934-937 (2012)), can be used to replace TET as a chemical oxidant to specifically oxidize 5hmC to 5fC (FIG. 7). This approach, referred to herein as Chemical-Assisted Pyridine borane Sequencing ("CAPS"), can be used to sequence 5hmC specifically (FIG. 5B, Table 1). Therefore, TAPS and related methods can in principle offer a comprehensive suite to sequence all four cytosine epigenetic modifications (FIG. 5B, Table 1, Table 6).

TAPS alone will detect the existing 5fC and 5caC in the genome as well. However, given the extremely low levels of 5fC and 5caC in genomic DNA under normal conditions, this will be acceptable. If under certain conditions, one would like to eliminate the 5fC and 5caC signals completely, it can also be readily accomplished by protecting the 5fC and 5caC by hydroxylamine conjugation and EDC coupling, respectively, thereby preventing conversion to DHU.

Figure 8:
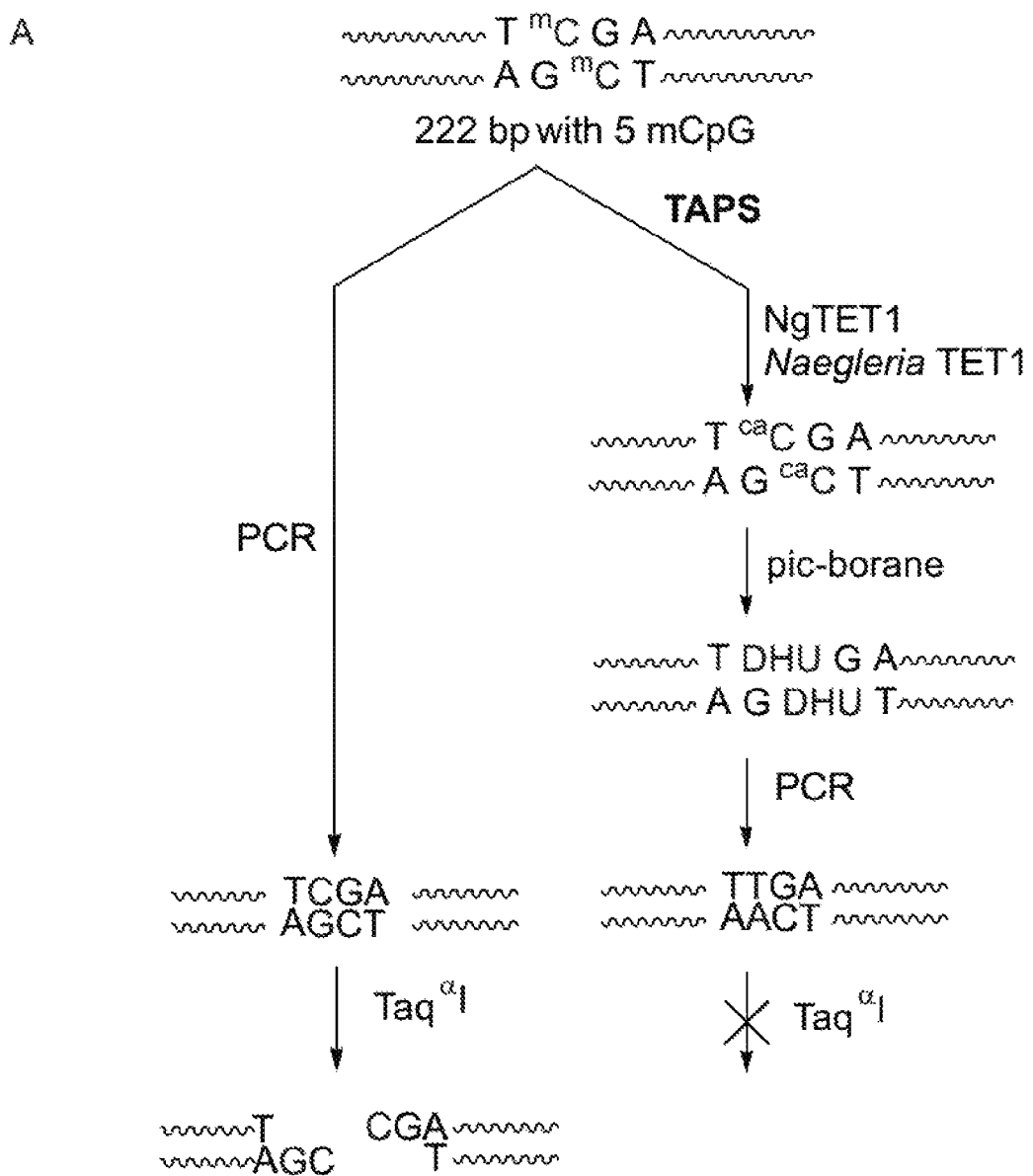
FIG. 8A-B. Restriction enzyme digestion showed TAPS could effectively convert 5mC to T. (A) Illustration of restriction enzyme digestion assay to confirm sequence change caused by TAPS. (B) TaqαI-digestion tests to confirm the C-to-T transition caused by TAPS. TAPS was performed on a 222 bp model DNA having a TaqαI restriction site and containing 5 fully methylated CpG sites (5mC) and its unmethylated control (C). PCR-amplified 222 bp model DNA can be cleaved with TaqαI to ~160 bp and ~60 bp fragments as shown in the 5mC, C and C TAPS. After TAPS on the methylated DNA, the T(mC)GA sequence is converted to TTGA and is no longer cleaved by TaqαI digestion as shown in the 5mC-TAPS lanes.
Figure 8:
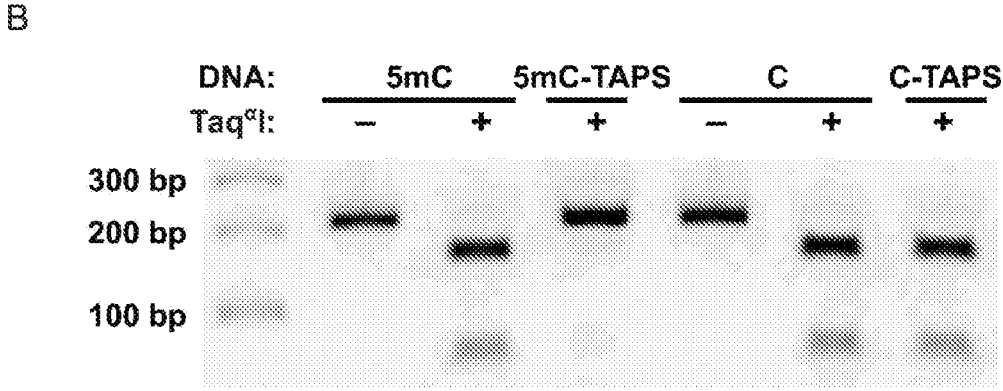
Figure 9:
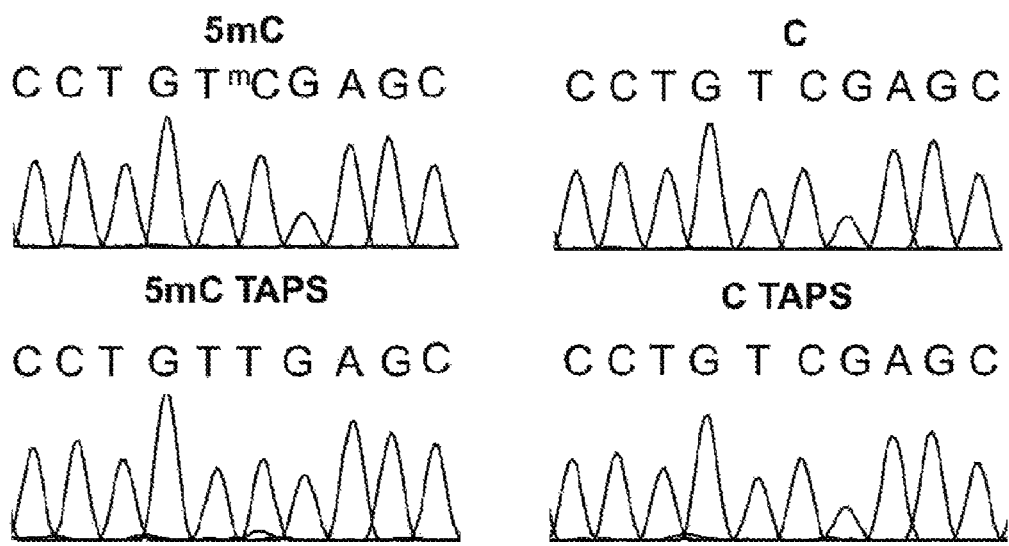
FIG. 9A-B. TAPS on a 222 bp model DNA and mESC gDNA. (A) Sanger sequencing results for the 222 bp model DNA containing 5 fully methylated CpG sites and its unmethylated control before (5mC, C) and after TAPS (5mC TAPS, C TAPS). Only 5mC is converted to T by the TAPS method. (B) HPLC-MS/MS quantification of relative modification levels in the mESCs gDNA control, after NgTET1 oxidation and after pic-borane reduction. Data shown as mean±SD of three replicates.
Figure 9:
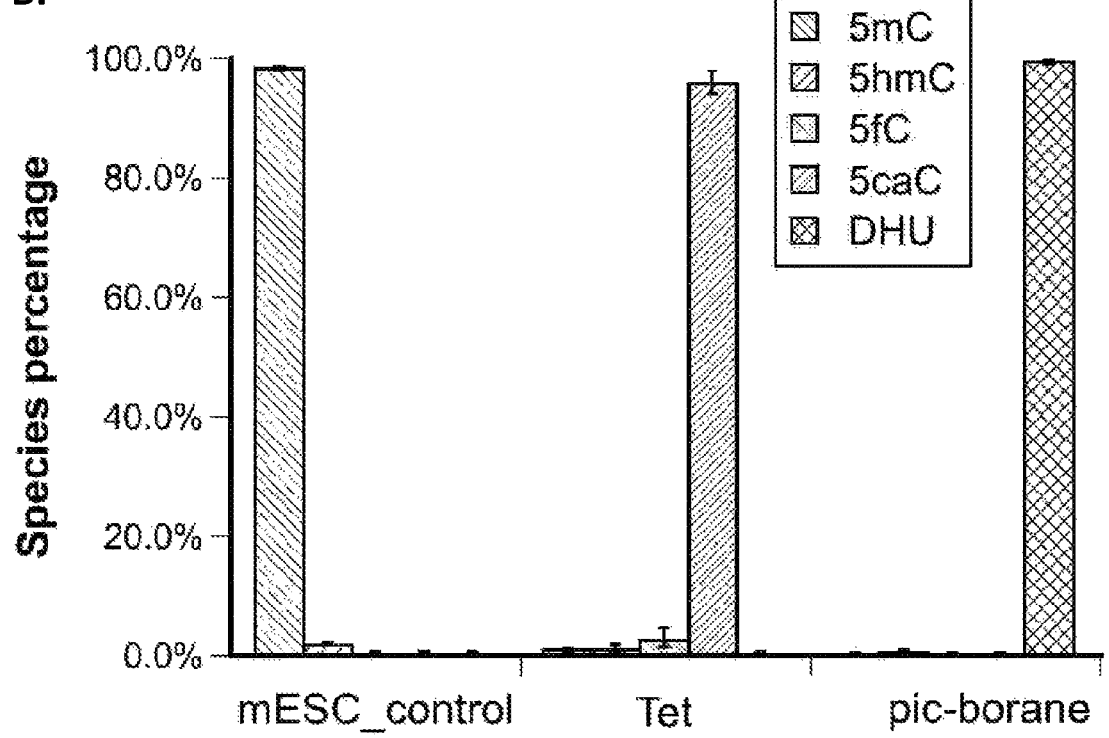
Figure 12:
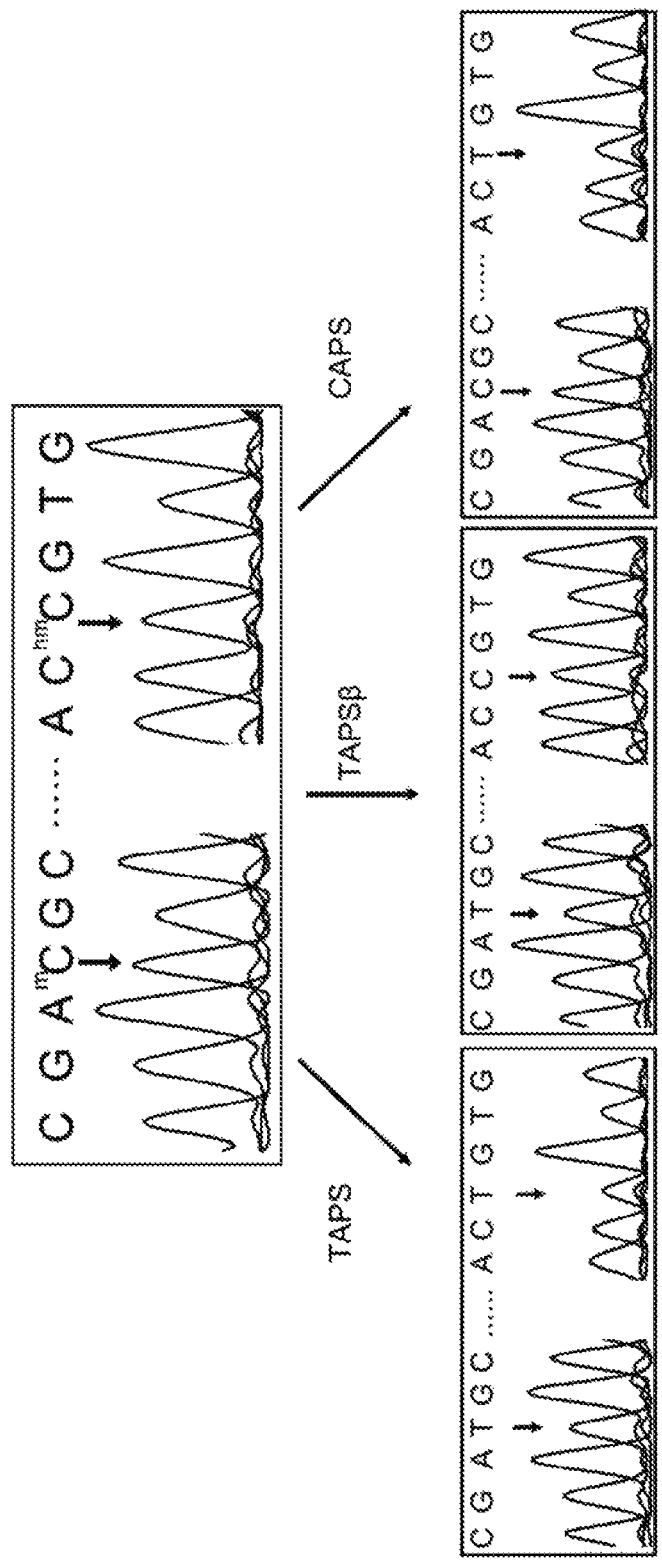
FIG. 12. Complete C-to-T transition induced after TAPS, TAPSβ and CAPS as demonstrated by Sanger sequencing. Model DNA containing single methylated and single hydroxymethylated CpG sites was prepared as described herein. TAPS conversion was done following NgTET1 oxidation and pyridine borane reduction protocol as described herein. TAPSβ conversion was done following 5hmC blocking, NgTET1 Oxidation and Pyridine borane reduction protocol. CAPS conversion was done following 5hmC oxidation and Pyridine borane reduction protocol. After conversion, 1 ng of converted DNA sample was PCR amplified by Taq DNA Polymerase and processed for Sanger sequencing. TAPS converted both 5mC and 5hmC to T. TAPSβ selectively converted 5mC whereas CAPS selectively converted 5hmC. None of the three methods caused conversion on unmodified cytosine and other bases.

The performance of TAPS was evaluated in comparison with bisulfite sequencing, the current standard and most widely used method for base-resolution mapping of 5mC and 5hmC. Naegleria TET-like oxygenase (NgTET1) and mouse Tet1 (mTet1) were used because both can efficiently oxidize 5mC to 5caC in vitro. To confirm the 5mC-to-T transition, TAPS was applied to model DNA containing fully methylated CpG sites and showed that it can effectively convert 5mC to T, as demonstrated by restriction enzyme digestion (FIG. 8A-B) and Sanger sequencing (FIG. 9A). TAPSβ and CAPS were also validated by Sanger sequencing (FIG. 12).

TAPS was also applied to genomic DNA (gDNA) from mouse embryonic stem cells (mESCs). HPLC-MS/MS quantification showed that, as expected, 5mC accounts for 98.5% of cytosine modifications in the mESCs gDNA; the remainder is composed of 5hmC (1.5%) and trace amounts 5fC and 5caC, and no DHU (FIG. 9B). After TET oxidation, about 96% of cytosine modifications were oxidized to 5caC and 3% were oxidized to 5fC (FIG. 9B). After borane reduction, over 99% of the cytosine modifications were converted into DHU (FIG. 9B). These results demonstrate both TET oxidation and borane reduction work efficiently on genomic DNA.

Figure 10:
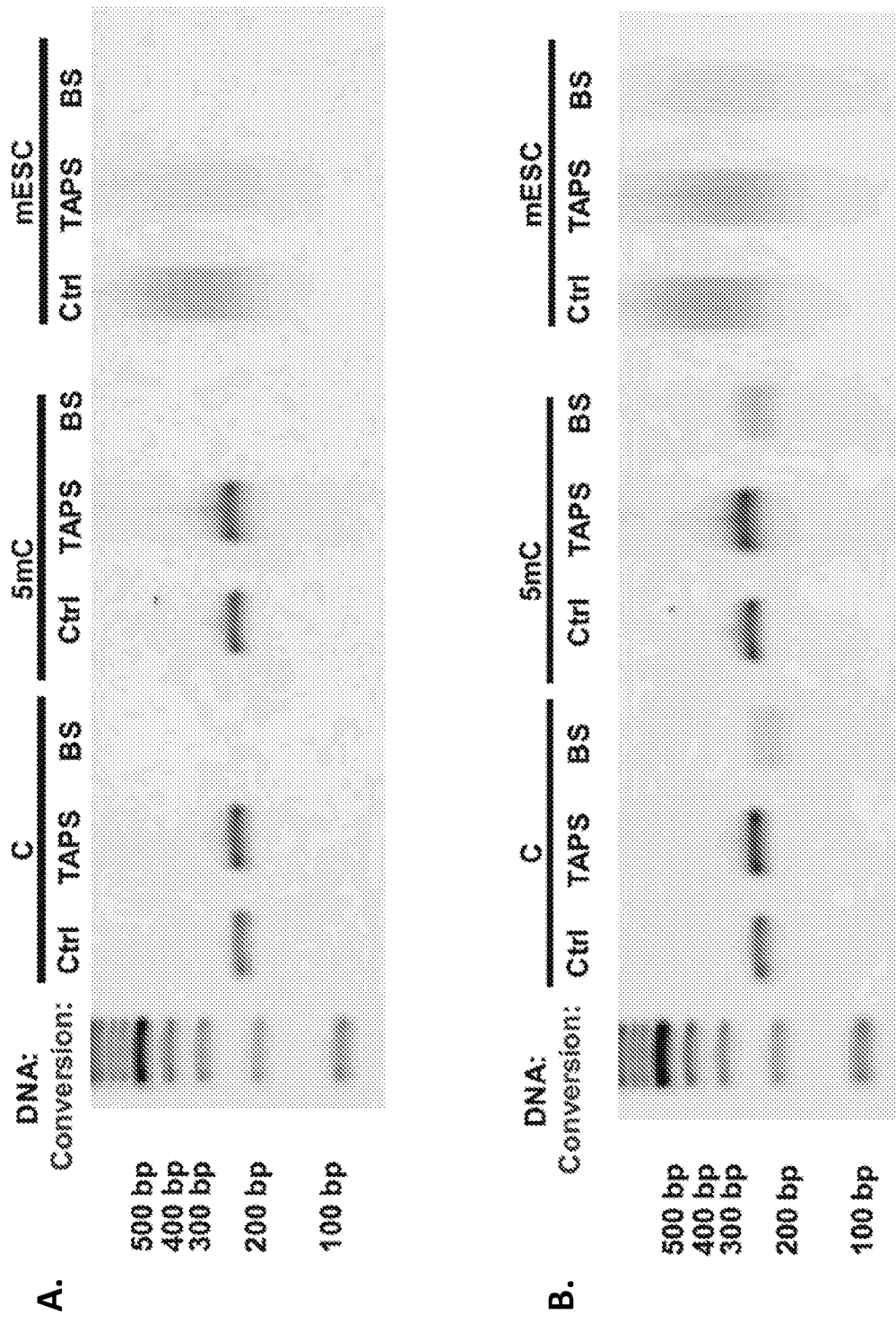
FIG. 10A-D. TAPS caused no significant DNA degradation compared to bisulfite. Agarose gel images of 222 bp unmethylated DNA, 222 bp methylated DNA, and mESC gDNA (A) before and (B) after chilling in an ice bath. No detectable DNA degradation was observed after TAPS and DNA remained double-stranded and could be visualized without chilling. Bisulfite conversion created degradation and DNA became single-stranded and could be visualized only after chilled on ice. (C) Agarose gel images of mESC gDNA of various fragment lengths treated with TAPS and bisulfite before (left panel) and after (right panel) cooling down on ice. DNA after TAPS remained double-stranded and could be directly visualized on the gel. Bisulfite treatment caused more damage and fragmentation to the samples and DNA became single-stranded and could be visualized only after chilled on ice. TAPS conversion was complete for all gDNA regardless of fragment length as shown in FIG. 15. (D) Agarose gel imaging of a 222 bp model DNA before and after TAPS (three independent repeats) showed no detectable degradation after the reaction.
Figure 10:
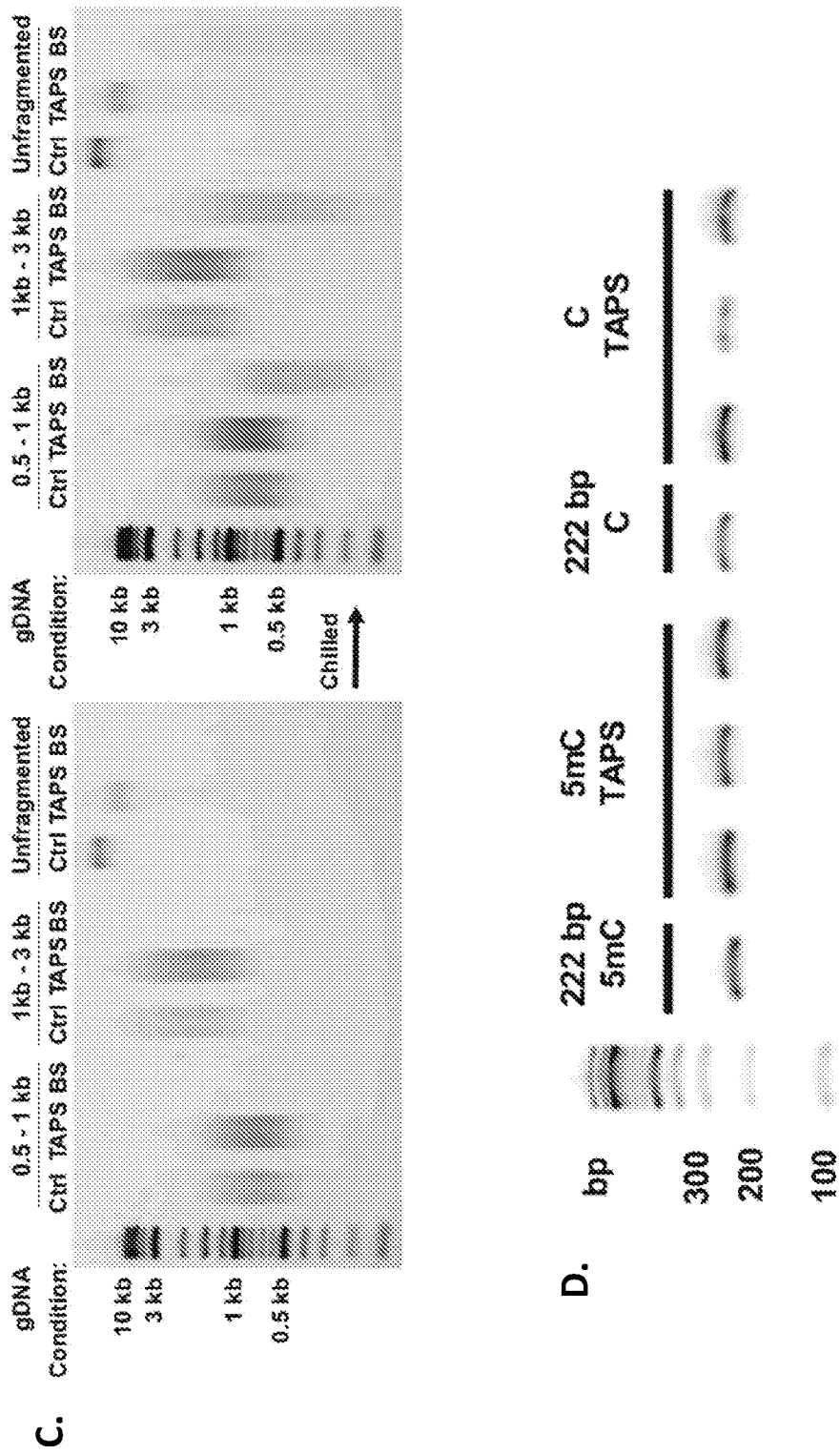
Figure 15:
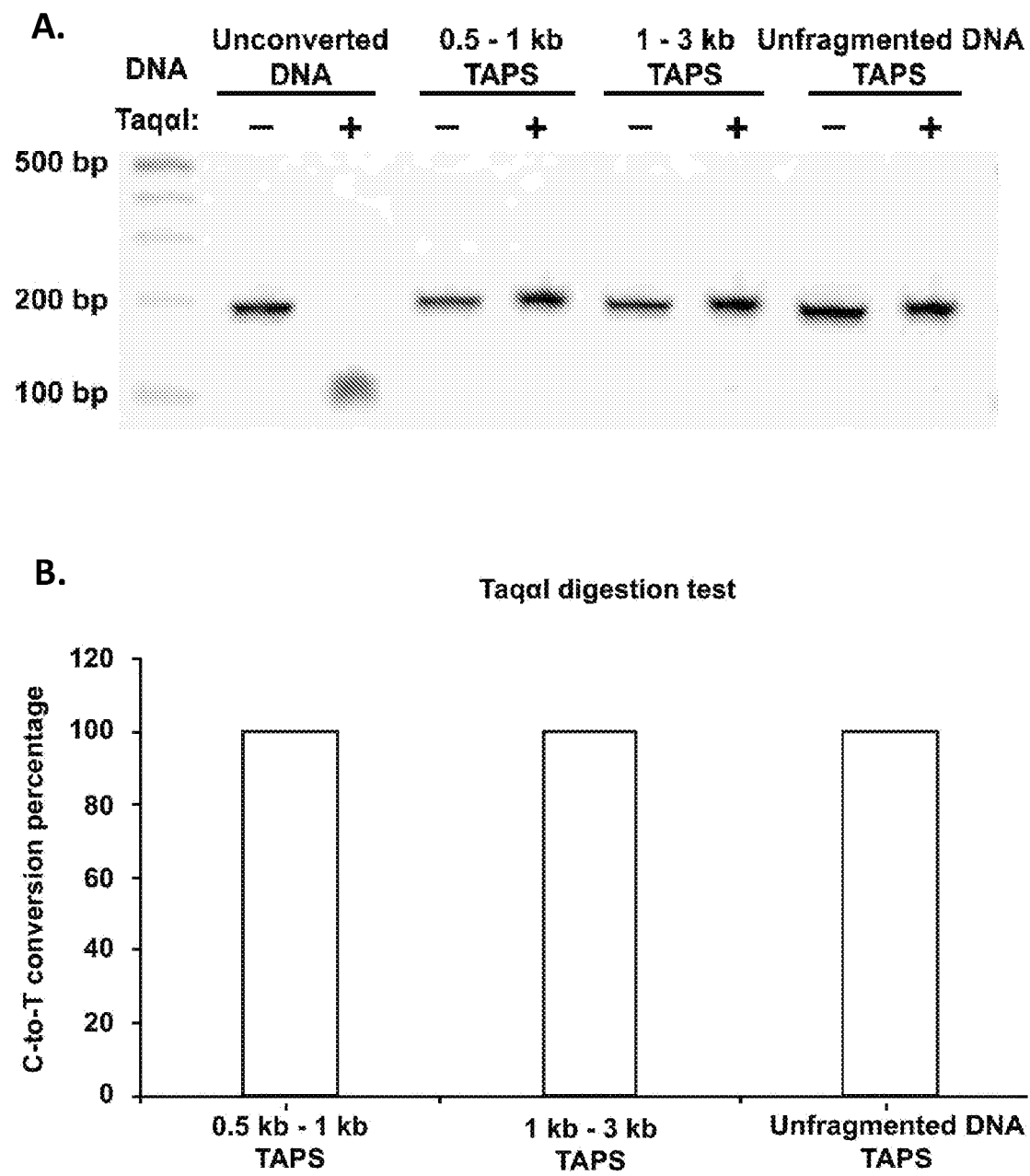
FIG. 15A-B. TAPS completely converted 5mC to T regardless of DNA fragment length. (A) Agarose gel images of TaqαI-digestion assay confirmed complete 5mC to T conversion in all samples regardless of DNA fragment lengths. 194 bp model sequence from lambda genome was PCR amplified after TAPS and digested with TaqαI enzyme. PCR product amplified from unconverted sample could be cleaved, whereas products amplified on TAPS treated samples stayed intact, suggesting loss of restriction site and hence complete 5mC-to-T transition. (B) The C-to-T conversion percentage was estimated by gel band quantification and shown 100% for all DNA fragment lengths tested.

Both TET oxidation and borane reduction are mild reactions, with no notable DNA degradation compared to bisulfite (FIG. 10A-D) and thereby provide high DNA recovery. Another notable advantage over bisulfite sequencing is that TAPS is non-destructive and can preserve DNA up to 10 kbs long (FIG. 10C). Moreover, DNA remains double stranded after TAPS (FIG. 10A-C), and the conversion is independent of the DNA length (FIG. 15A-B).

Figure 13:
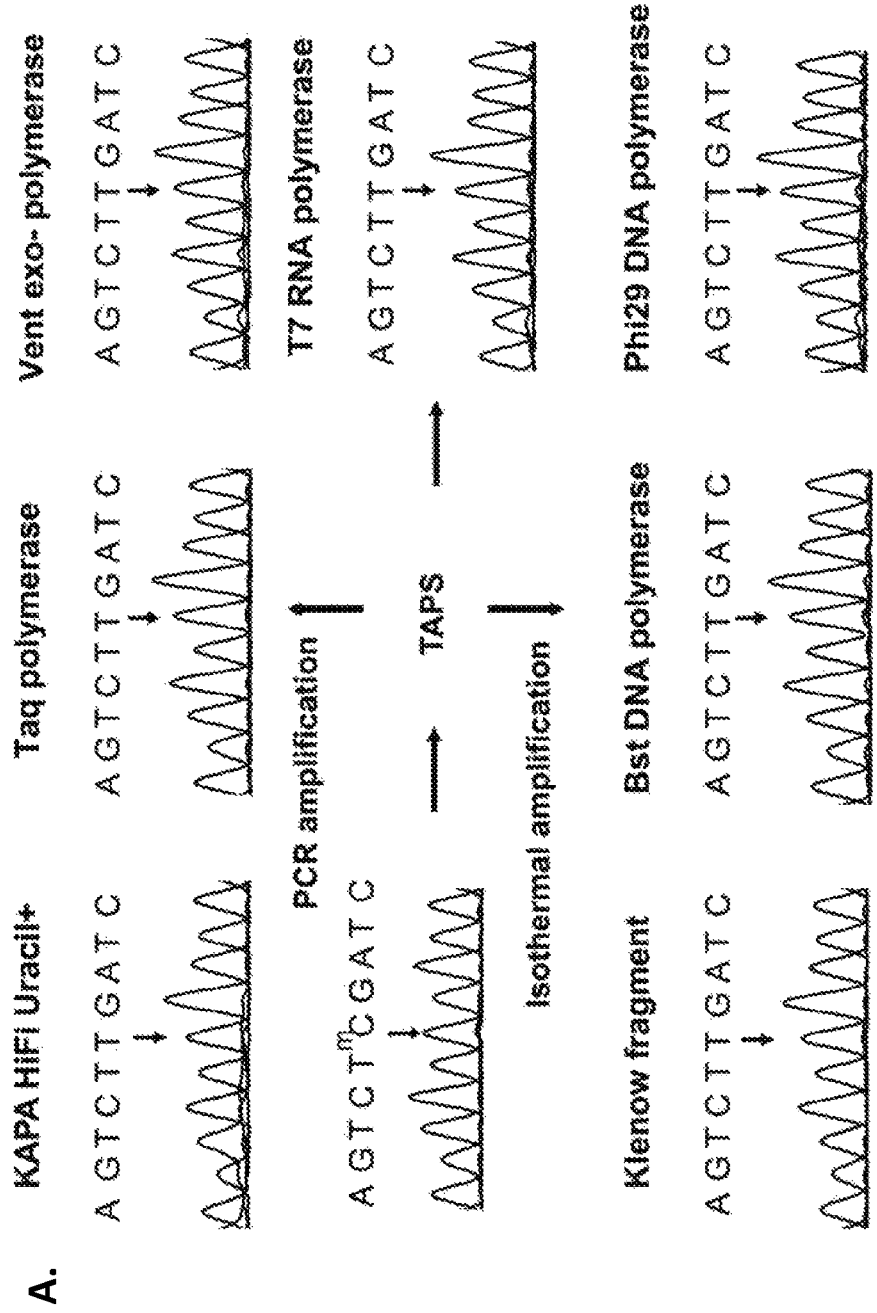
FIG. 13A-B. (A) TAPS is compatible with various DNA and RNA polymerase and induces complete C-to-T transition as shown by Sanger sequencing. Model DNA containing methylated CpG sites for the polymerase test and primer sequences are described herein. After TAPS treatment, 5mC was converted to DHU. KAPA HiFi Uracil plus polymerase, Taq polymerase, and Vent exo-polymerase would read DHU as T and therefore induce complete C-to-T transition after PCR. Alternatively, primer extension was done with biotin-labelled primer and isothermal polymerases including Klenow fragment, Bst DNA polymerase, and phi29 DNA polymerase. The newly synthesized DNA strand was separated by Dynabeads MyOne Streptavidin Cl and then amplified by PCR with Taq polymerase and processed for Sanger sequencing. T7 RNA polymerase could efficiently bypass DHU and insert adenine opposite to DHU site, which is proved by RT-PCR and Sanger sequencing. (B) Certain other commercialized polymerases did not amplify DHU containing DNA efficiently. After TAPS treatment, 5mC was converted to DHU. KAPA HiFi Uracil plus polymerase and Taq polymerase would read DHU as T and therefore induce complete C-to-T transition. Low or no C-to-T transition was observed with certain other commercialized polymerases including KAPA HiFi polymerase, Pfu polymerase, Phusion polymerase and NEB Q5 polymerase (not shown).
Figure 13:
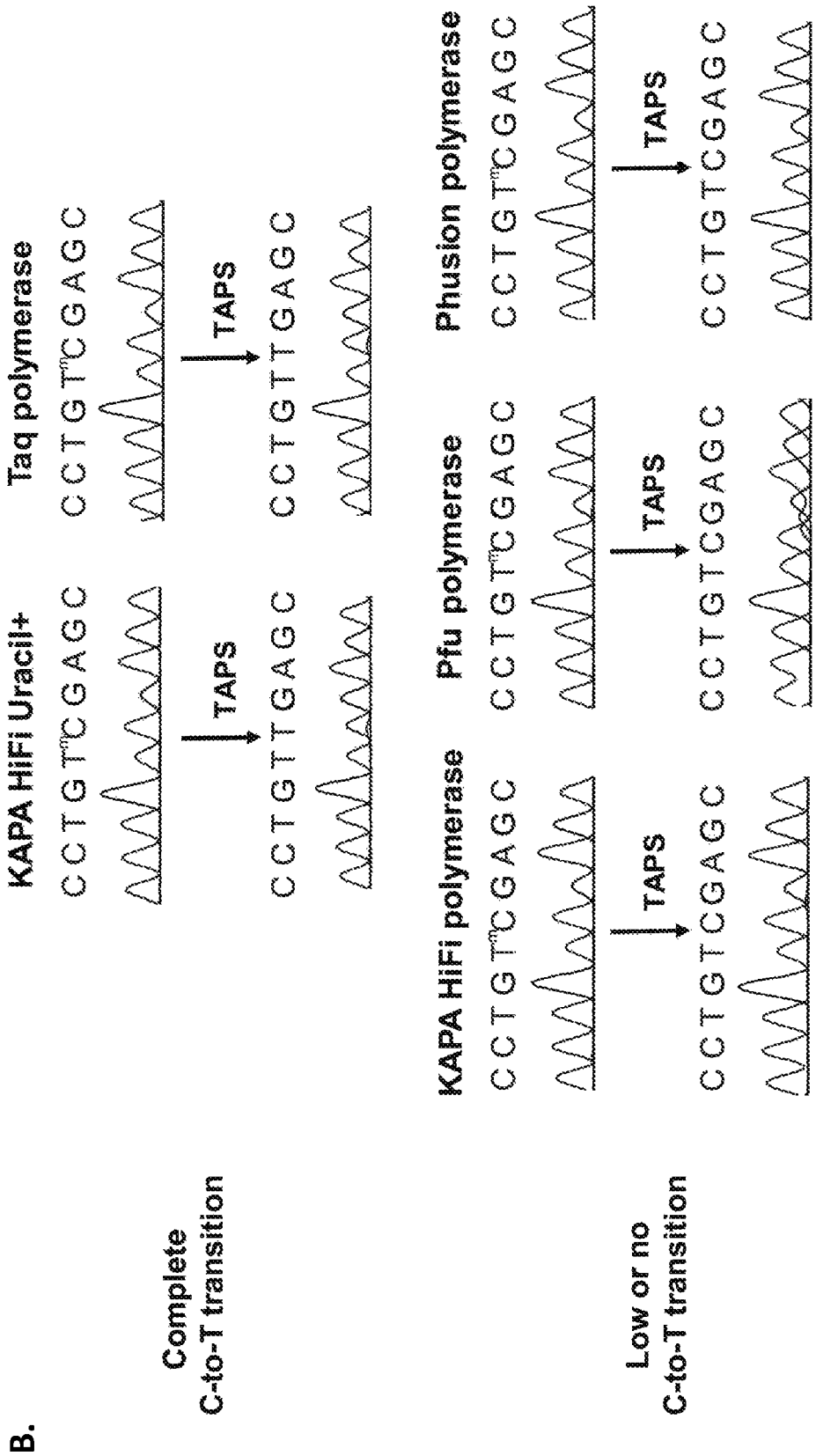
Figure 14:
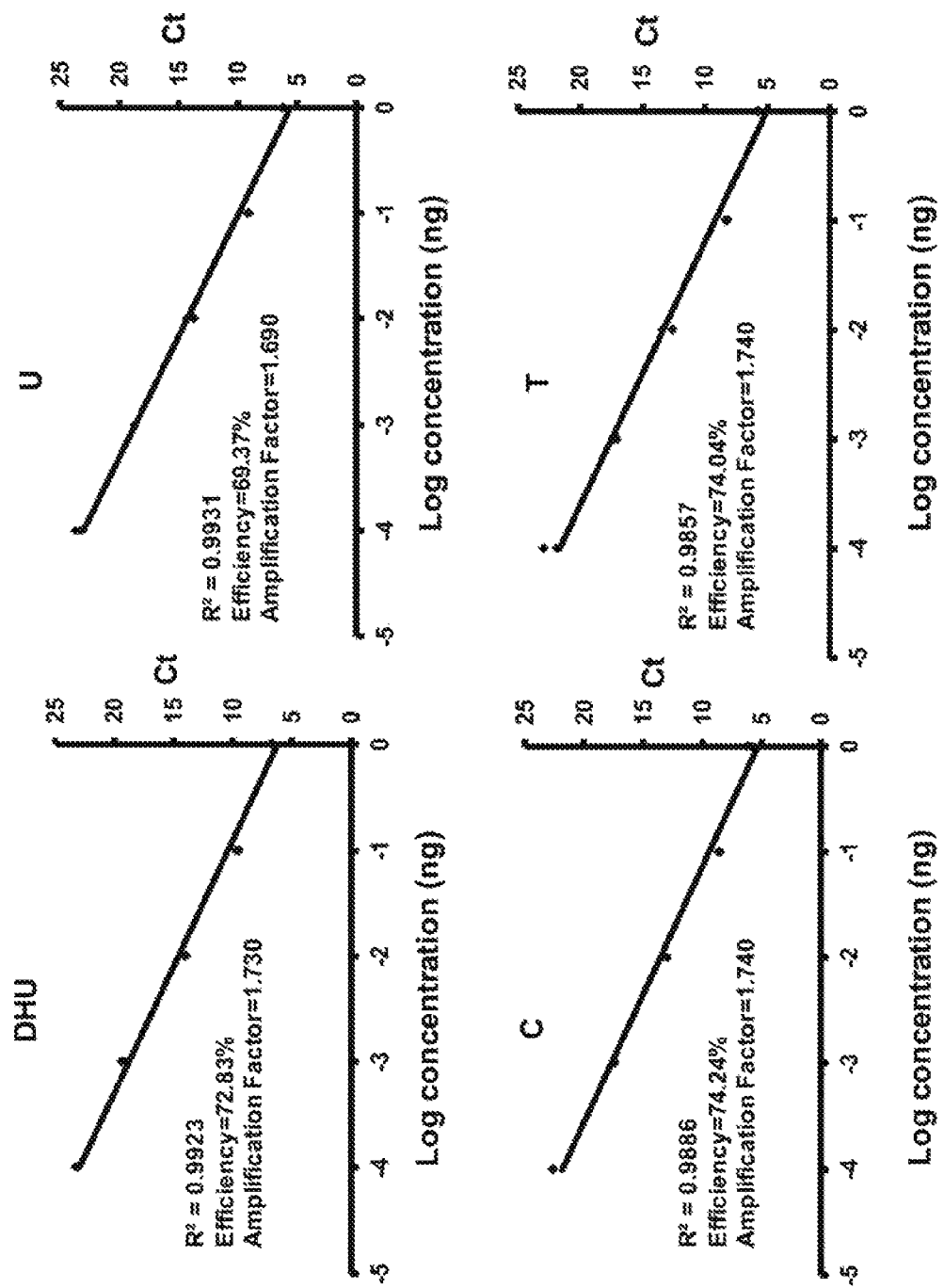
FIG. 14. DHU does not show PCR bias compared to T and C. Model DNA containing one DHU/U/T/C modification was synthesized with the corresponding DNA oligos as described in herein. Standard curves for each model DNA with DHU/U/T/C modification were plotted based on qPCR reactions with 1:10 serial dilutions of the model DNA input (from 0.1 pg to 1 ng, every qPCR experiment was run in triplicates). The slope of the regression between the log concentration (ng) values and the average Ct values was calculated by SLOPE function in Excel. PCR efficiency was calculated using the following equation: Efficiency %=(10^(-1/Slope)-1)*100%. Amplification factor was calculated using the following equation: Amplification factor=10^(-1/Slope). PCR efficiency for model DNAs with DHU or T or C modification were almost the same, which demonstrated that DHU could be read through as a regular base and would not cause PCR bias.

In addition, because DHU is close to a natural base, it is compatible with various DNA polymerases and isothermal DNA or RNA polymerases (FIGS. 13A-B) and does not show a bias compared to T/C during PCR (FIG. 14).

Whole genome sequencing was performed on two samples of mESC gDNA, one converted using TAPS and the other using standard whole-genome bisulfite sequencing (WGBS) for comparison.

Figure 17:
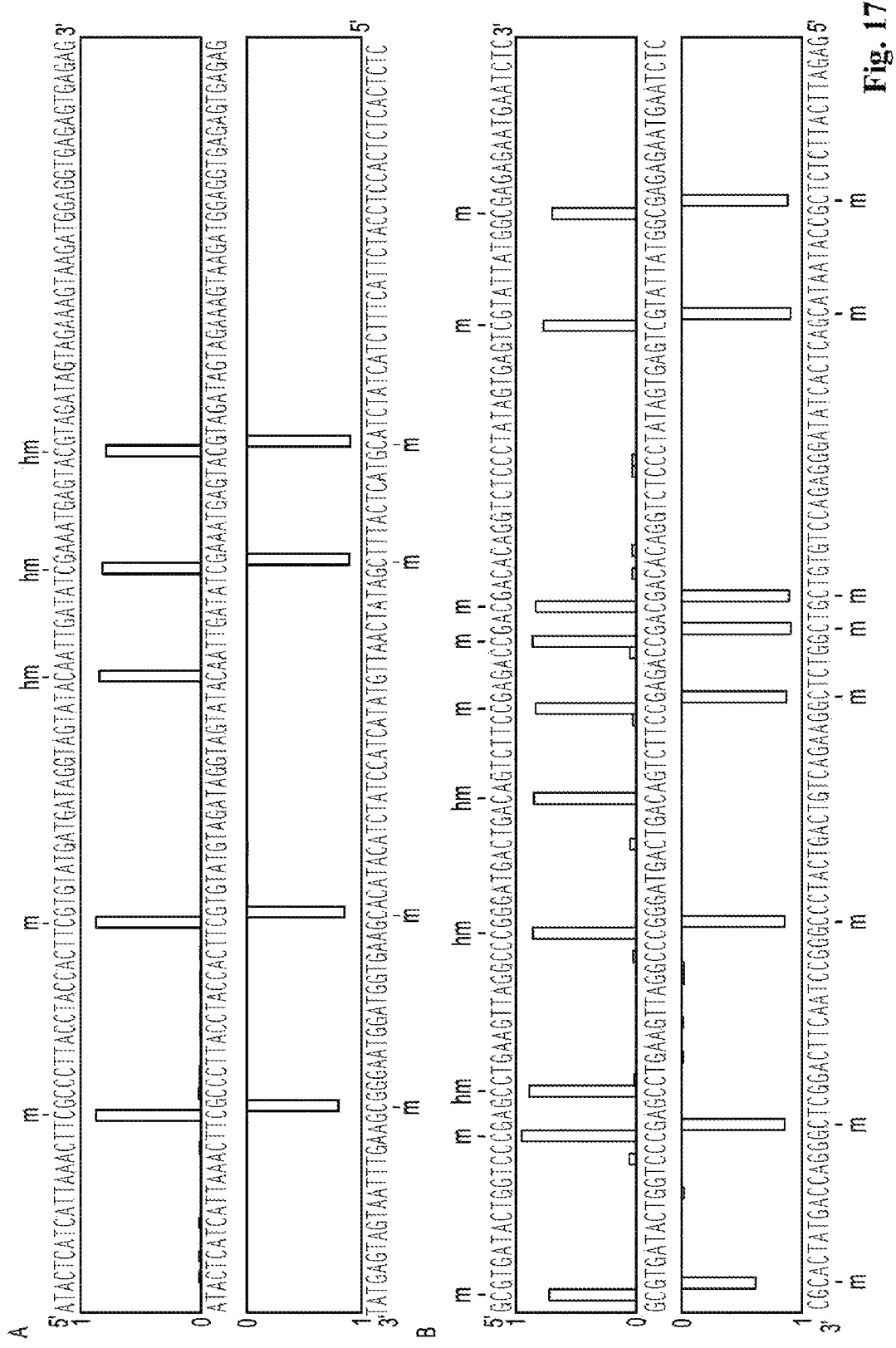
FIG. 17A-B. Conversion rate on short spike-ins. (A) 120mer-1 and (B) 120mer-2 containing 5mC and 5hmC. Near complete conversion was archived on 5mC and 5hmC sites from both strands. Actual sequences with modification status shown on top and bottom.

To assess the accuracy of TAPS, spike-ins of different lengths were added that were either fully unmodified, in vitro methylated using CpG Methyltransferase (M.SssI) or GpC Methyltransferase (M.CviPI) (using the above methods). For short spike-ins (120mer-1 and 120mer-2) containing 5mC and 5hmC, near complete conversion was observed for both modifications on both strands in both CpG and non-CpG contexts (FIG. 17A-B).

Figure 16:
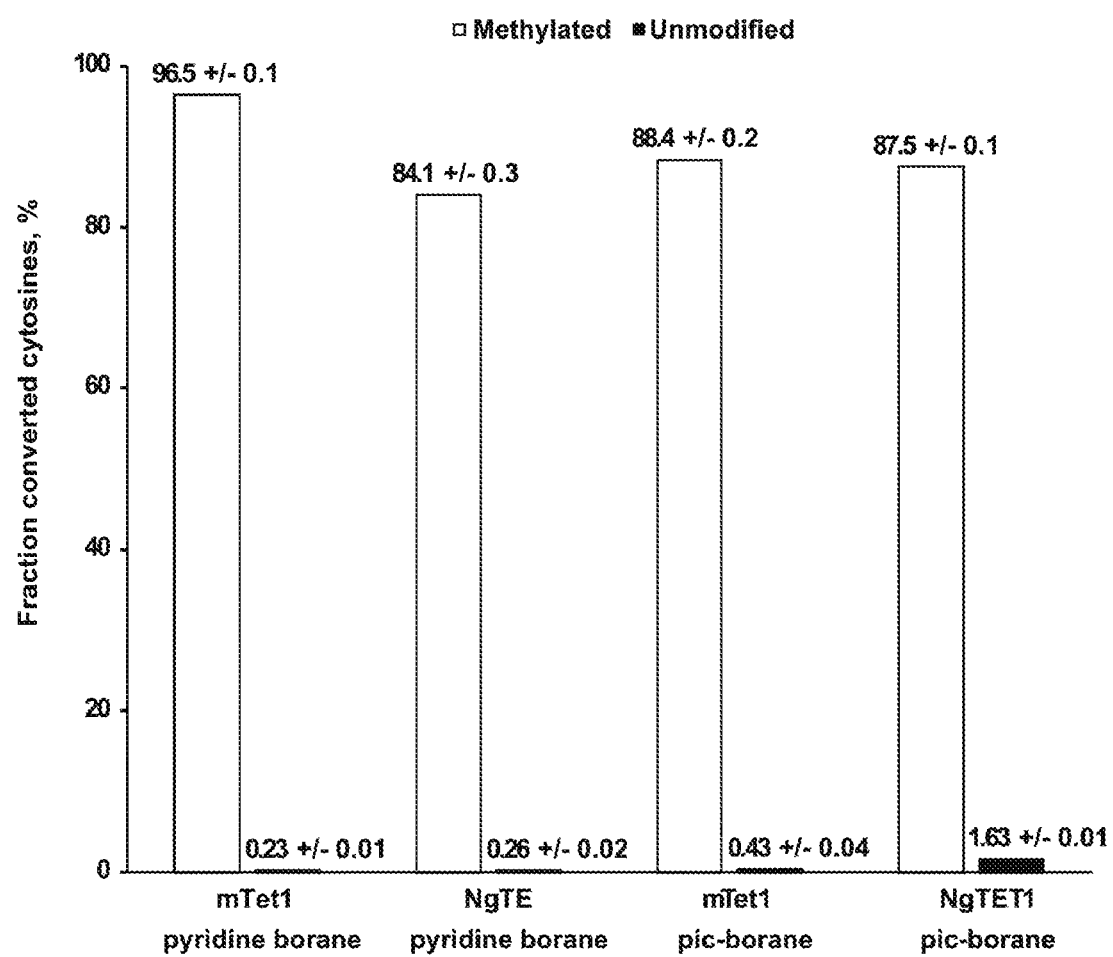
FIG. 16. The conversion and false positive for different TAPS conditions. The combination of mTet1 and pyridine borane achieved the highest conversion rate of methylated C (96.5%, calculated with fully CpG methylated Lambda DNA) and the lowest conversion rate of unmodified C (0.23%, calculated with 2 kb unmodified spike-in), compared to other conditions with NgTET1 or pic-borane. Showing above bars the conversion rate+/−SE of all tested cytosine sites.
Figure 18:
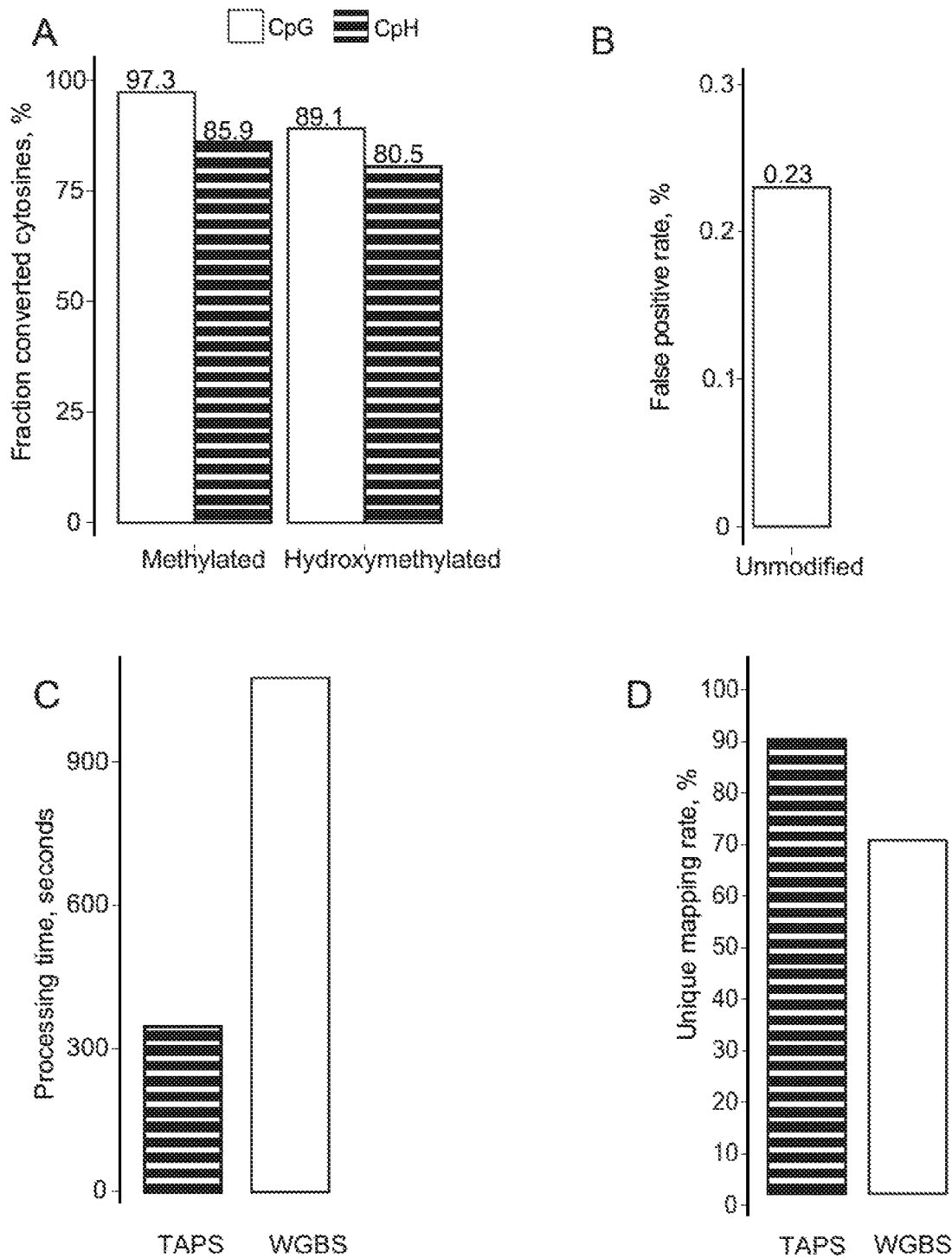
FIG. 18A-E. Improved sequencing quality of TAPS over Whole Genome Bisulfite Sequencing (WGBS). (A) Conversion rate of 5mC and 5hmC in TAPS-treated DNA. Left: Synthetic spike-ins (CpN) methylated or hydroxymethylated at known positions. (B) False positive rate of TAPS from unmodified 2 kb spike-in. (C) Total run time of TAPS and WGBS when processing 1 million simulated reads on one core of one Intel Xeon CPU. (D) Fraction of all sequenced read pairs (after trimming) mapped to the genome. (E) Sequencing quality scores per base for the first and second reads in all sequenced read pairs, as reported by Illumina BaseSpace. Top: TAPS. Bottom: WGBS.
Figure 18:
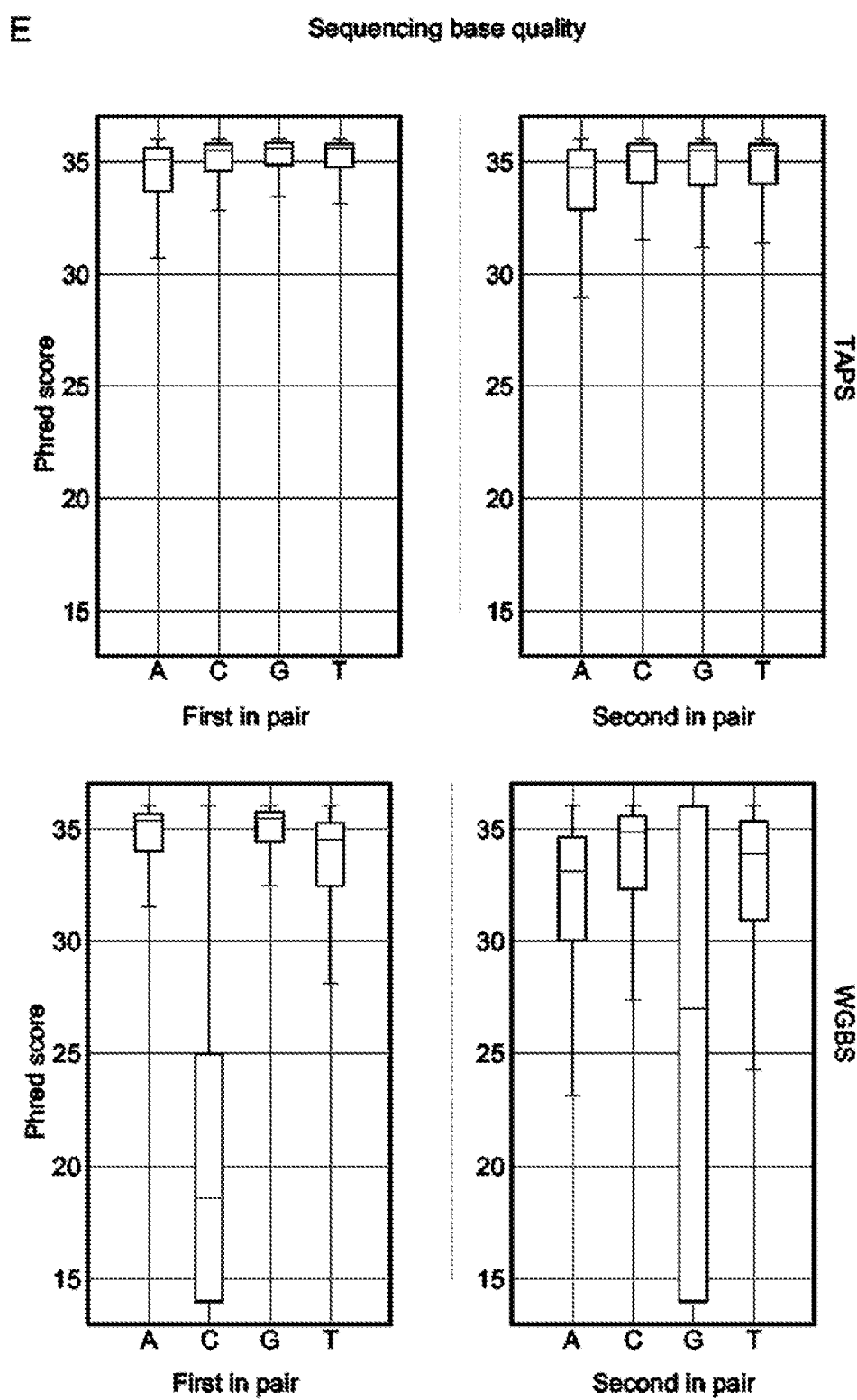

100 ng gDNA was used for TAPS, compared to 200 ng gDNA for WGBS. To assess the accuracy of TAPS, we added three different types of spike-in controls. Lambda DNA where all CpGs were fully methylated was used to estimate the false negative rate (non-conversion rate of 5mC); a 2 kb unmodified amplicon was used to estimate the false positive rate (conversion rate of unmodified C); synthetic oligo spike-ins containing both a methylated and hydroxymethylated C surrounded by any other base (N5mCNN and N5hmCNN, respectively) were used to compare the conversion rate on 5mC and 5hmC in different sequence contexts. The combination of mTet1 and pyridine borane achieved the highest 5mC conversion rate (96.5% and 97.3% in lambda and synthetic spike-ins, respectively) and the lowest conversion rate of unmodified C (0.23%) (FIG. 18A-B and FIG. 16). A false negative rate between 2.7% and 3.5%, with a false-positive rate of only 0.23%, is comparable to bisulfite sequencing: a recent study showed 9 commercial bisulfite kits had average false negative and false positive rates of 1.7% and 0.6%, respectively (Holmes, E. E. et al. Performance evaluation of kits for bisulfite-conversion of DNA from tissues, cell lines, FFPE tissues, aspirates, lavages, effusions, plasma, serum, and urine. PLoS One 9, e93933 (2014)). The synthetic spike-ins suggest that TAPS works well on both 5mC and 5hmC, and that TAPS performs only slightly worse in non-CpG contexts. The conversion for 5hmC is 8.2% lower than 5mC, and the conversion for non-CpG contexts is 11.4% lower than for CpG contexts (FIG. 18A).

WGBS data requires special software both for the alignment and modification-calling steps. In contrast, our processing pipeline uses a standard genomic aligner (bwa), followed by a custom modification-calling tool that we call "asTair". When processing simulated WGBS and TAPS reads (derived from the same semi-methylated source sequence), TAPS/asTair was more than 3× faster than WGBS/Bismark (FIG. 18C).

Due to the conversion of nearly all cytosine to thymine, WGBS libraries feature an extremely skewed nucleotide composition which can negatively affect Illumina sequencing. Consequently, WGBS reads showed substantially lower sequencing quality scores at cytosine/guanine base pairs compared to TAPS (FIG. 18E). To compensate for the nucleotide composition bias, at least 10 to 20% PhiX DNA (a base-balanced control library) is commonly added to WGBS libraries (see, e.g., Illumina's Whole-Genome Bisulfite Sequencing on the HiSeq 3000/HiSeq 4000 Systems). Accordingly, we supplemented the WGBS library with 15% PhiX. This, in combination with the reduced information content of BS-converted reads, and DNA degradation as a result of bisulfite treatment, resulted in significantly lower mapping rates for WGBS compared to TAPS (FIG. 18D and Table 7).

TABLE 7

Mapping and sequencing quality statistics for WGBS and TAPS.

| Measure | WGBS | TAPS |
|---|---|---|
| Total raw reads | 376062375 | 455548210 |
| Trimmed reads | 367860813 | 453028186 |
| Mapped reads (mm9 + spike-ins + PhiX) | 251940139 | 451077132 |
| PCR deduplicated reads | 232303596 | 398127851 |
| Mapping rate (mapped reads/trimmed reads) | 68.49% | 99.57% |
| Unique mapping rate (unique reads [MAPQ > 0 for TAPS]/trimmed reads) | 68.49% | 88.08% |
| Unique PCR deduplicated mapping rate (unique PCR deduplicated reads [MAPQ > 0 for TAPS]/trimmed reads) | 63.15% | 81.31% |

Figure 19:
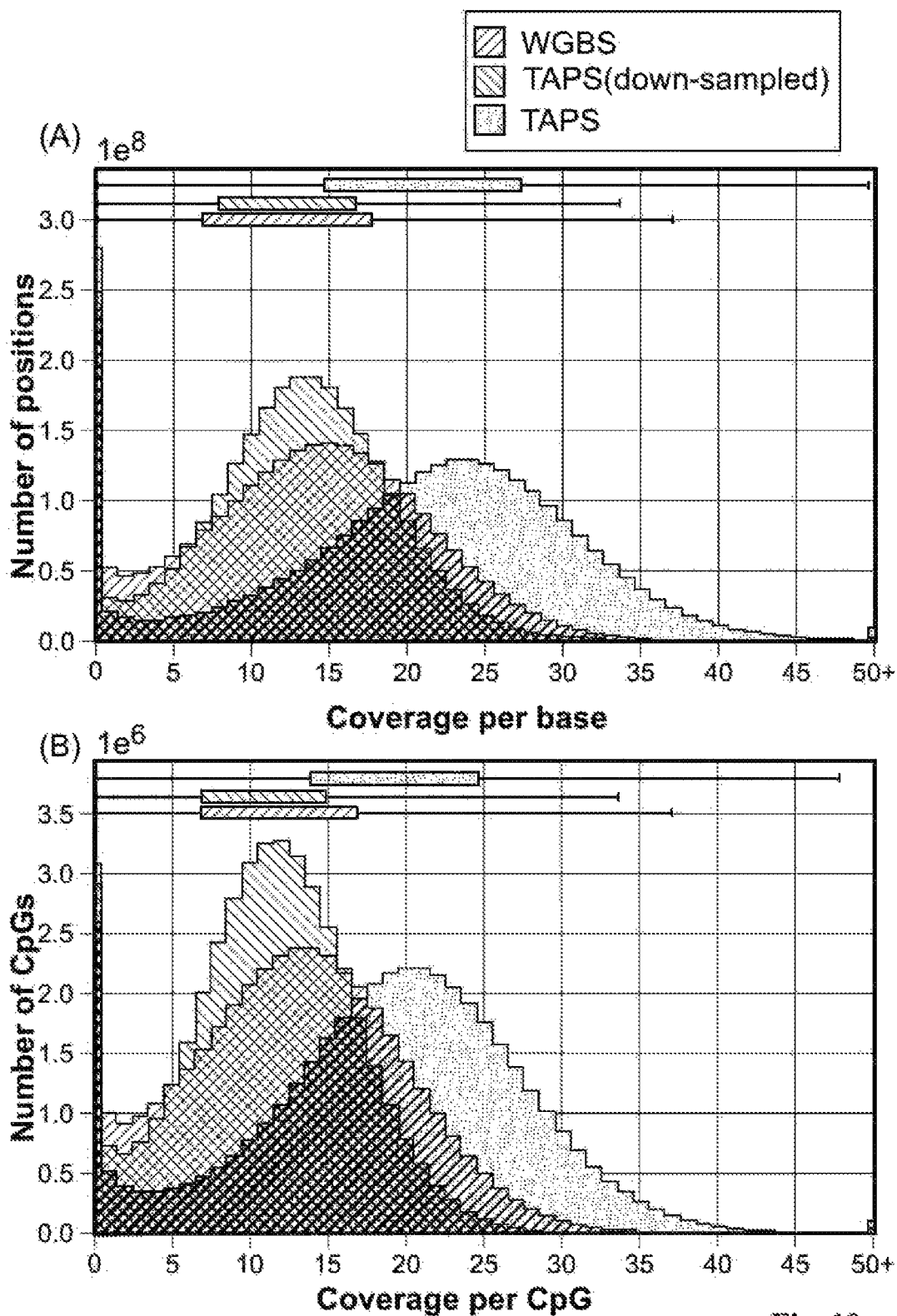
FIG. 19A-B. TAPS resulted in more even coverage and fewer uncovered positions than WGBS. Comparison of depth of coverage across (A) all bases and (B) CpG sites between WGBS and TAPS, computed on both strands. For "TAPS (down-sampled)", random reads out of all mapped TAPS reads were selected so that the median coverage matched the median coverage of WGBS. Positions with coverage above 50× are shown in the last bin.

Therefore, for the same sequencing cost (one NextSeq High Output run), the average depth of TAPS exceeded that of WGBS (21× and 13.1×, respectively; Table 8). Furthermore, TAPS resulted in fewer uncovered regions, and overall showed a more even coverage distribution, even after down-sampling to the same sequencing depth as WGBS (inter-quartile range: 9 and 11, respectively; FIG. 19A and Table 8).

TABLE 8

Coverage statistics for TAPS, WGBS and TAPS down-sampled to have approximately the same mean coverage as WGBS. Here, coverage was computed for both strands at all positions in the genome.

| Measure | WGBS | TAPS with down-sampling | TAPS without down-sampling |
|---|---|---|---|
| Mean | 13.078 | 12.411 | 21.001 |
| Variance | 1988.242 | 482.242 | 1371.912 |
| median | 13 | 13 | 22 |
| qtl25 | 7 | 8 | 15 |
| qtl75 | 18 | 17 | 28 |
| iqr | 11 | 9 | 13 |
| maximum | 116084 | 37329 | 63526 |

Figure 21:
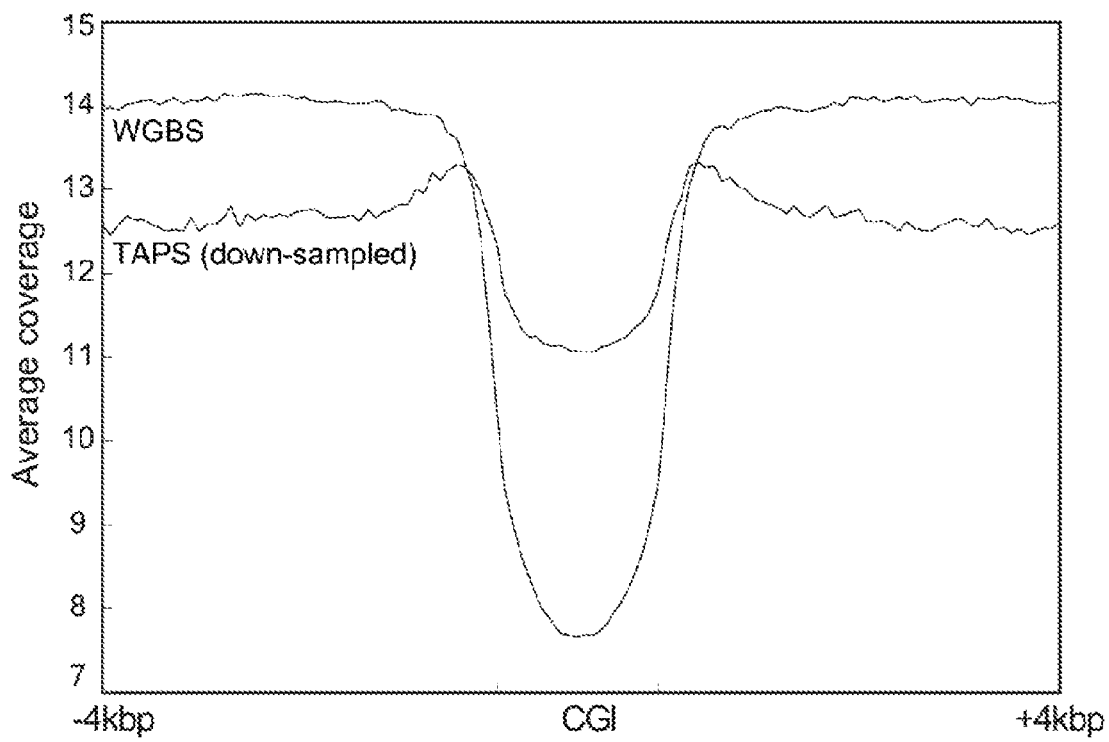
FIG. 21A-E. Comparison of genome-wide methylome measurements by TAPS and WGBS. (A) Average sequencing coverage depth in all mouse CpG islands (binned into 20 windows) and 4 kbp flanking regions (binned into 50 equally sized windows). To account for differences in sequencing depth, all mapped TAPS reads were down-sampled to match the median number of mapped WGBS reads across the genome. (B) CpG sites covered by at least three reads by TAPS alone, both TAPS and WGBS, or WGBS alone. (C) Number of CpG sites covered by at least three reads and modification level >0.1 detected by TAPS alone, TAPS and WGBS, or WGBS alone. (D) Example of the chromosomal distribution of modification levels (in %) for TAPS and WGBS. Average fraction of modified CpGs per 100 kb windows along mouse chromosome 4, smoothed using a Gaussian-weighted moving average filter with window size 10. (E) Heatmap representing the number of CpG sites covered by at least three reads in both TAPS and WGBS, broken down by modification levels as measured by each method. To improve contrast, the first bin, containing CpGs unmodified in both methods, was excluded from the color scale and is denoted by a star.
Figure 21:
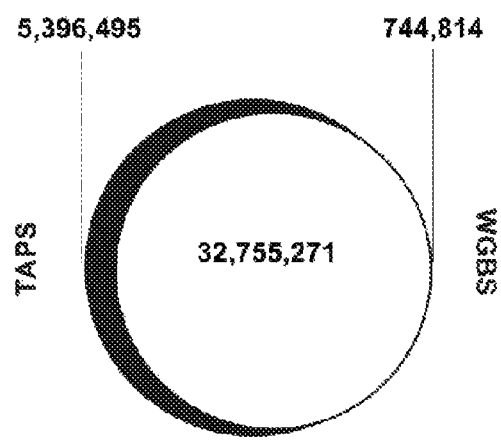
Figure 21:
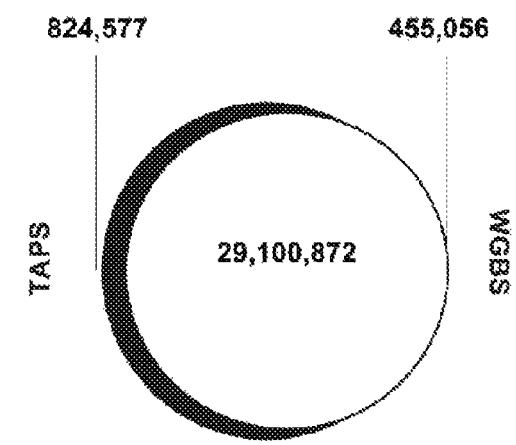
Figure 21:
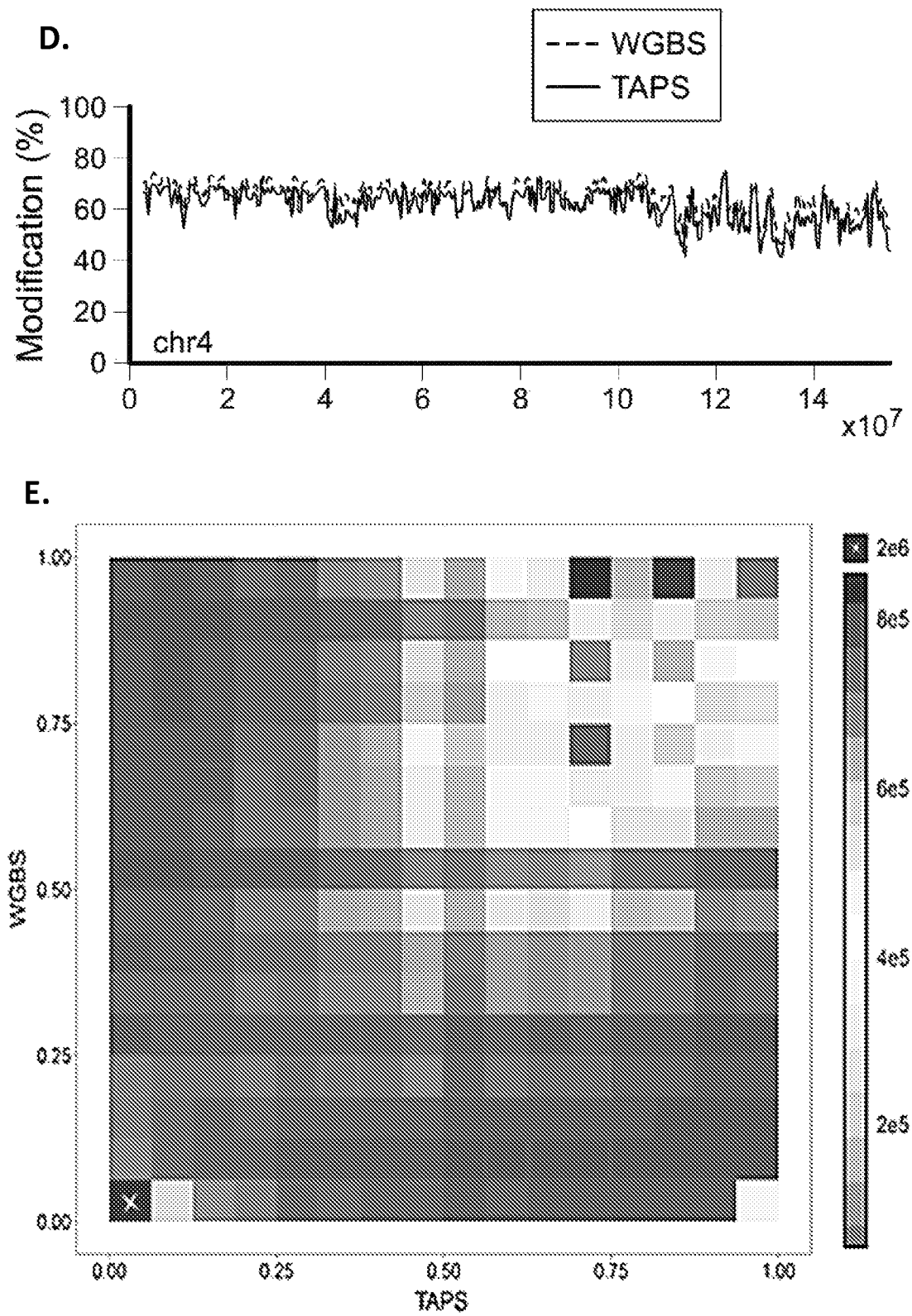
Figure 22:
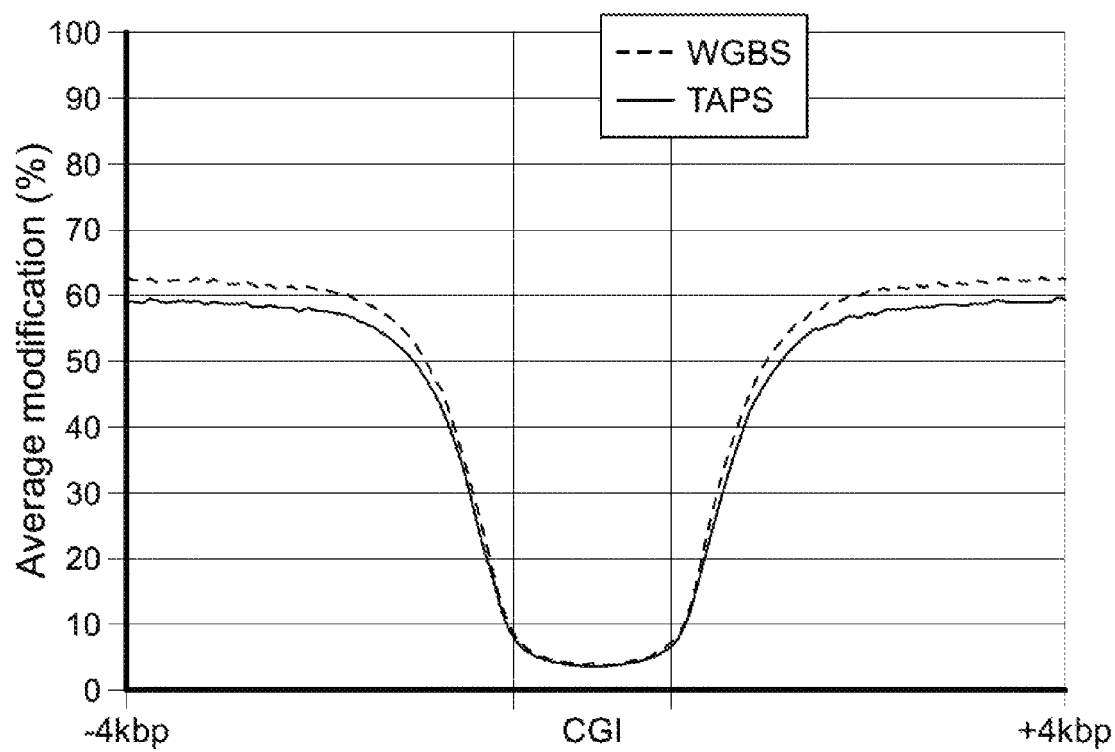
FIG. 22. Modification levels around CpG Islands. Average modification levels in CpG islands (binned into 20 windows) and 4 kbp flanking regions (binned into 50 equally sized windows). Bins with coverage below 3 reads were ignored.
Figure 23:
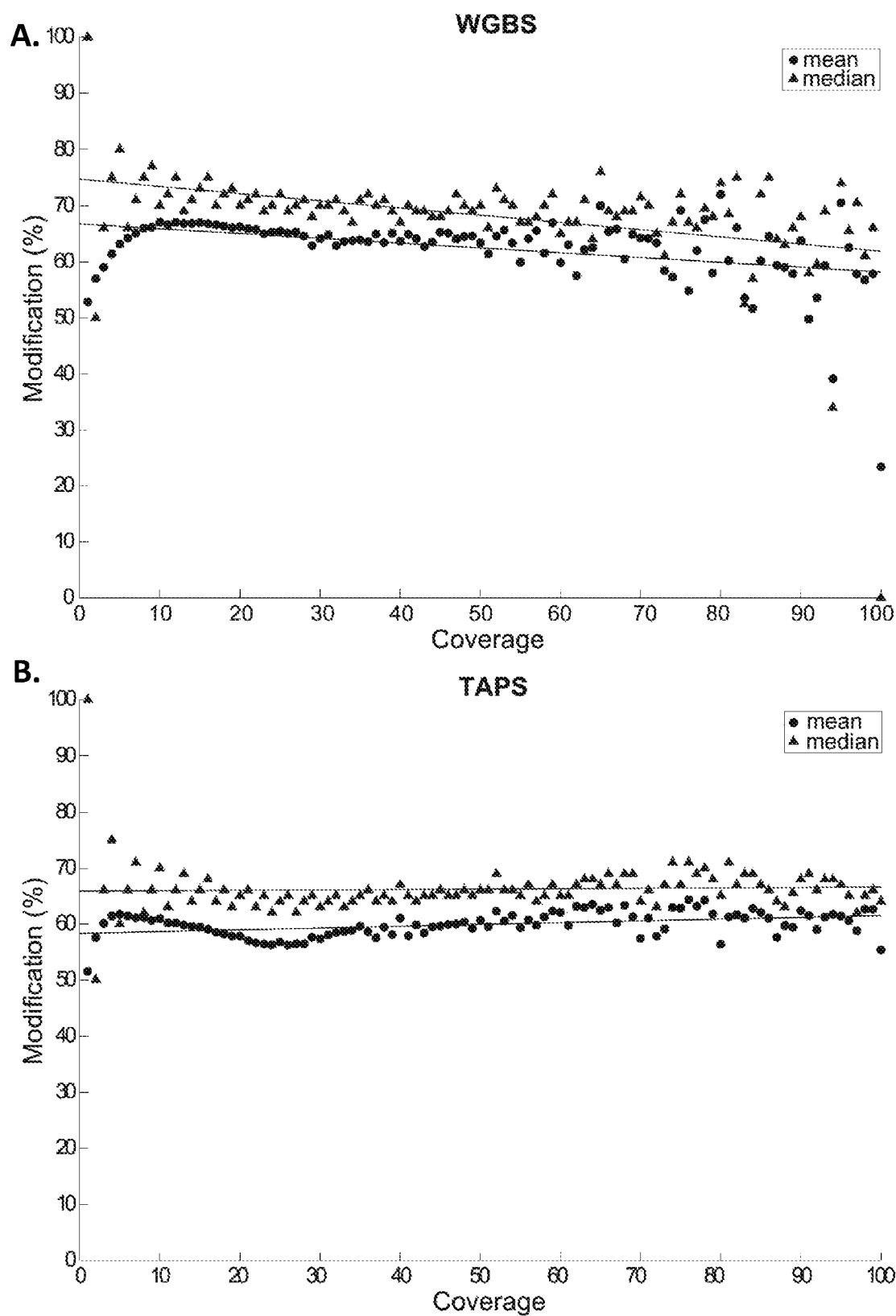
FIG. 23A-B. TAPS exhibits smaller coverage-modification bias than WGBS. All CpG sites were binned according to their coverage and the mean (circles) and the median (triangles) modification value is shown in each bin for WGBS (A) and TAPS (B). The CpG sites covered by more than 100 reads are shown in the last bin. The lines represent a linear fit through the data points.
Figure 24:
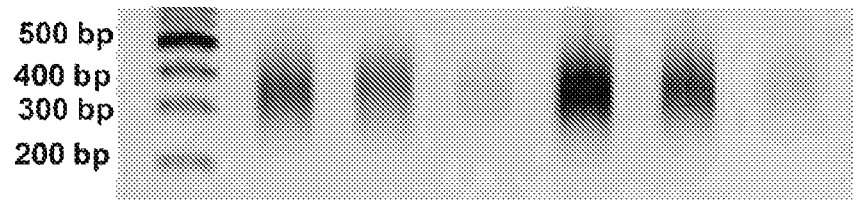
FIG. 24A-C. Low-input gDNA and cell-free DNA TAPS prepared with dsDNA and ssDNA library preparation kits. (A) Sequencing libraries were successfully constructed with down to 1 ng of murine embryonic stem cell (mESC) genomic DNA (gDNA) with dsDNA library kits NEBNext Ultra II or KAPA HyperPrep kits. ssDNA library kit Accel-NGS Methyl-Seq kit was used to further lower the input DNA amount down to (B) 0.01 ng of mESC gDNA or (C) 1 ng of cell-free DNA.
Figure 24:
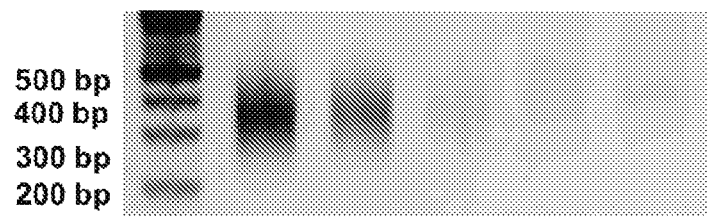
Figure 24:
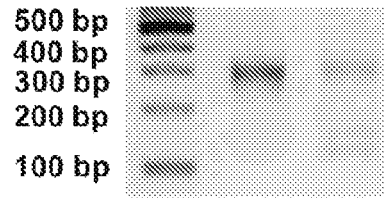
Figure 25:
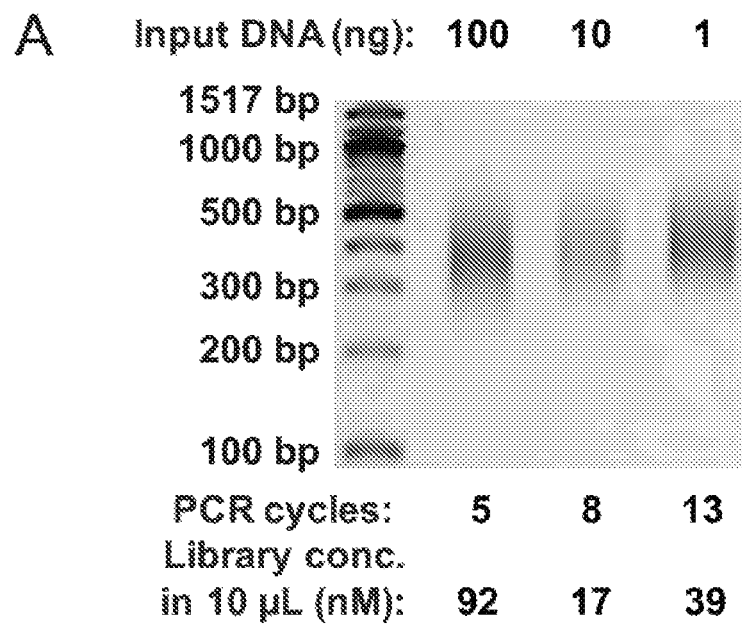
FIG. 25A-B. Low-input gDNA and cell-free DNA TAPS libraries prepared with dsDNA KAPA HyperPrep library preparation kit. Sequencing libraries were successfully constructed with as little as 1 ng of (A) mESC gDNA and (B) cell-free DNA with KAPA HyperPrep kit. Cell-free DNA has a sharp length distribution around 160 bp (nucleosome size) due to plasma nuclease digestion. After library construction, it becomes ~300 bp, which is the sharp band in (B).
Figure 25:
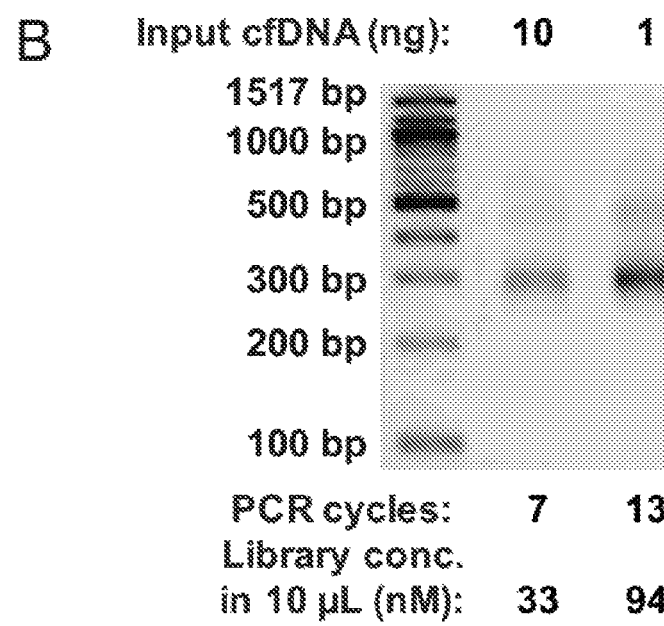

For example, CpG Islands (CGIs) in particular were generally better covered by TAPS, even when controlling for differences in sequencing depth between WGBS and TAPS (FIG. 21A), while both showed equivalent demethylation inside CGIs (FIG. 22). Moreover, WGBS showed a slight bias of decreased modification levels in highly covered CpG sites (FIG. 23A), while our results suggest that TAPS exhibits very little of the modification-coverage bias (FIG. 23B). These results demonstrate that TAPS dramatically improved sequencing quality compared to WGBS, while effectively halving the sequencing cost.

Figure 20:
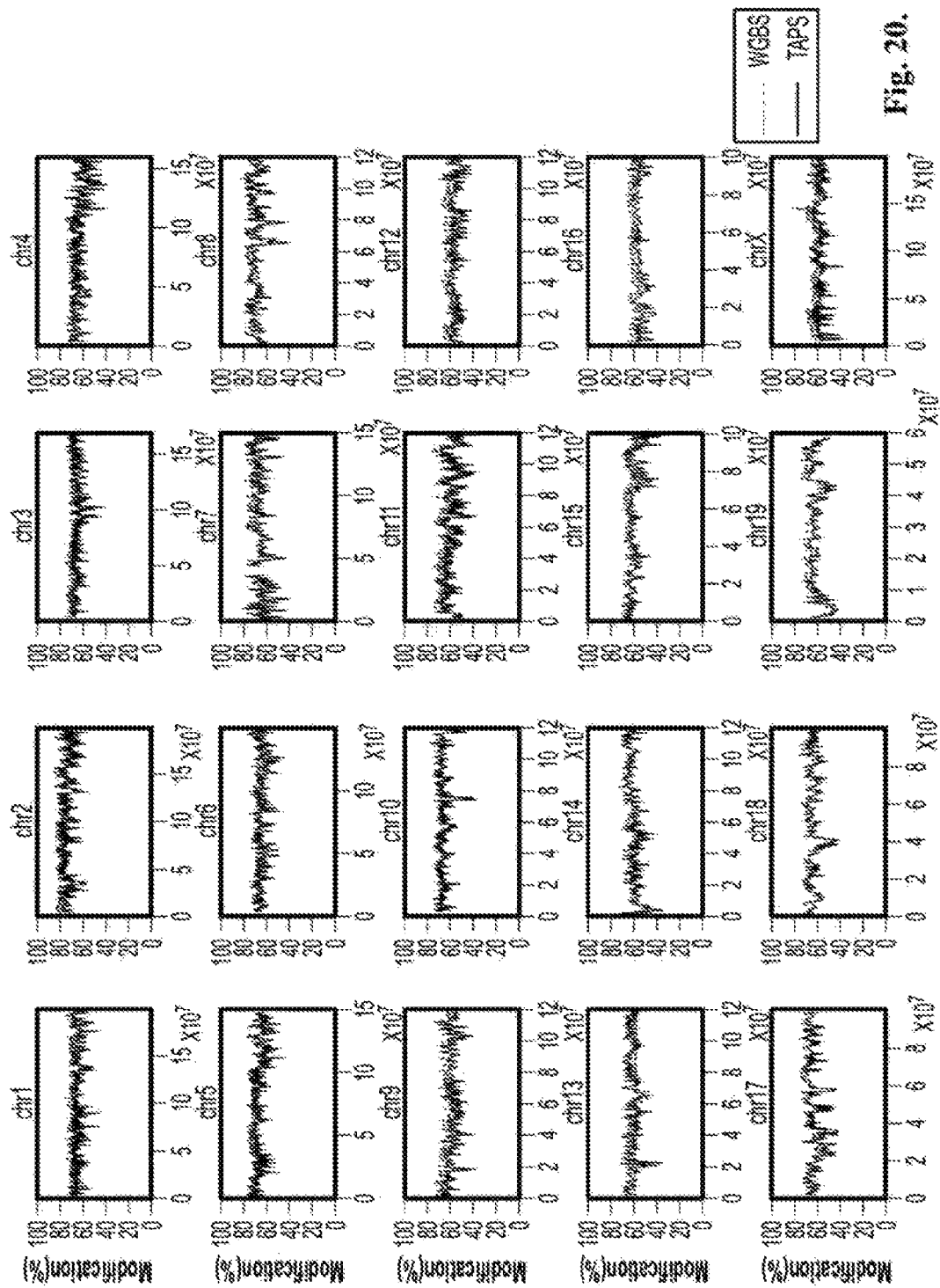
FIG. 20. Distribution of modification levels across all chromosomes. Average modification levels in 100 kb windows along mouse chromosomes, weighted by the coverage of CpG, and smoothed using a Gaussian weighted moving average filter with window size 10.

The higher and more even genome coverage of TAPS resulted in a larger number of CpG sites covered by at least three reads. With TAPS, 88.3% of all 43,205,316 CpG sites in the mouse genome were covered at this level, compared to only 77.5% with WGBS (FIGS. 21B and 19B). TAPS and WGBS resulted in highly correlated methylation measurements across chromosomal regions (FIG. 21D and FIG. 20). On a per-nucleotide basis, 32,755,271 CpG positions were covered by at least three reads in both methods (FIG. 21B). Within these sites, we defined "modified CpGs" as all CpG positions with a modification level of at least 10% (L. Wen et al., Whole-genome analysis of 5-hydroxymethylcytosine and 5-methylcytosine at base resolution in the human brain. *Genome Biology* 15, R49 (2014)). Using this threshold, 95.8% of CpGs showed matching modification states between TAPS and WGBS. 98.5% of all CpGs that were covered by at least three reads and found modified in WGBS were recalled as modified by TAPS, indicating good agreement between WGBS and TAPS (FIG. 21C). When comparing modification levels per each CpG covered by at least three reads in both WGBS and TAPS, good correlation between TAPS and WGBS was observed (Pearson r=0.63, p<2e-16, FIG. 21E). Notably, TAPS identified a subset of highly modified CpG positions which were missed by WGBS (FIG. 21E, bottom right corner). We further validated 7 of these CpGs, using an orthogonal restriction digestion and real-time PCR assay, and confirmed all of them are fully methylated and/or hydroxymethylated (Table 9).

TABLE 9

Comparison of CmCGG methylation level in mESC gDNA quantified by TAPS, WGBS and HpaII-qPCR assay. Coverage and methylation level ($^mC\%$) by TAPS and WGBS were computed for per strand. Ct value for HpaII digested sample ($Ct_{HpaII}$) or control sample ($Ct_{Ctrl}$) in the HpaII-qPCR assay was average of triplicates. mC% is calculated using following equation:
$^mC\% = 2^{\wedge}(Ct_{Ctrl} - Ct_{HpaII}) * 100\%$.

| Position of C$^m$CGG | TAPS Coverage | $^mC\%$ | WGBS Coverage | $^mC\%$ | HpaII-qPCR assay | | | Forward and reverse primer (5'-3') |
|---|---|---|---|---|---|---|---|---|
| | | | | | $Ct_{HpaII}$ | $Ct_{Ctrl}$ | $^mC\%$ | |
| chr6: 135868201 | 17 | 100% | 11 | 0% | 29.628 | 29.642 | 101.0% | GCTGCAGATTGGAGC CAAAG TTGATGGTGATGGTG GAGCC |
| chr3: 31339449 | 15 | 100% | 10 | 0% | 22.162 | 22.111 | 96.5% | TCAGTGCTCATGGAC TCATACT |

TABLE 9-continued

Comparison of CmCGG methylation level in mESC gDNA quantified by TAPS, WGBS and HpaII-qPCR assay. Coverage and methylation level ($^mC\%$) by TAPS and WGBS were computed for per strand. Ct value for HpaII digested sample ($Ct_{HpaII}$) or control sample ($Ct_{Ctrl}$) in the HpaII-qPCR assay was average of triplicates. mC% is calculated using following equation:
$$^mC\% = 2^{(Ct_{Ctrl} - Ct_{HpaII})} *100\%.$$

| Position of C$^m$CGG | TAPS Coverage | TAPS $^mC\%$ | WGBS Coverage | WGBS $^mC\%$ | HpaII-qPCR assay $Ct_{HpaII}$ | HpaII-qPCR assay $Ct_{Ctrl}$ | HpaII-qPCR assay $^mC\%$ | Forward and reverse primer (5'-3') |
|---|---|---|---|---|---|---|---|---|
| | | | | | | | | ATACCCTGGGAGCAAAGTTGTTG |
| chr4: 128271030 | 12 | 100% | 10 | 0% | 31.304 | 31.279 | 98.3% | CCCACTAGACATGCTCTGCC |
| | | | | | | | | CAAAATGTTGCTTGCCTTCCG |
| chr1: 58635199 | 11 | 100% | 8 | 0% | 22.008 | 22.026 | 101.3% | TCCCTGAGCCCTGATCTAGT |
| | | | | | | | | AATACTGGCTGACCGGTTCT |
| chr14: 36331351 | 11 | 100% | 14 | 0% | 21.228 | 21.053 | 88.6% | ACACCACAGCAGAAGAGAGC |
| | | | | | | | | TAGGATTGTTGCACAGGCCA |
| chr19: 42893499 | 11 | 100% | 18 | 0% | 22.515 | 22.558 | 103.0% | GCTGAGCTGTATCCTTGAGGT |
| | | | | | | | | ACACGTGGGTATTCCACAGC |
| chr3: 113611193 | 10 | 100% | 5 | 0% | 22.439 | 22.545 | 107.6% | GTGGATCTTCAGTGGTGGCA |
| | | | | | | | | ATGCTCCCTCATCCTTTGCA |
| Negative CCGG site | | | | | | | | |
| chr19: 9043049 | 25 | 0% | 17 | 0% | 27.11 | 21.409 | 1.9% | AGCCTCTGAACTTGACTGCC |
| | | | | | | | | GCCTGGAACTCCTGACAGTC |
| Positive CCGG site | | | | | | | | |
| chr15: 39335961 | 16 | 100% | 4 | 100% | 22.163 | 22.248 | 106.1% | GGTCCTTGATCCACCCAGAC |
| | | | | | | | | ACATGGTGCTGGTCTAACCG |

Together, these results indicate that TAPS can directly replace WGBS, and in fact provides a more comprehensive view of the methylome than WGBS.

Finally, TAPS was tested with low input DNA and TAPS was shown to work with as little as 1 ng gDNA and in some instances down to 10 pg of gDNA, close to single-cell level. TAPS also works effectively with down to 1 ng of circulating cell-free DNA. These results demonstrate the potential of TAPS for low input DNA and clinical applications (FIG. 24A-C, FIG. 25A-B).

Figure 26:
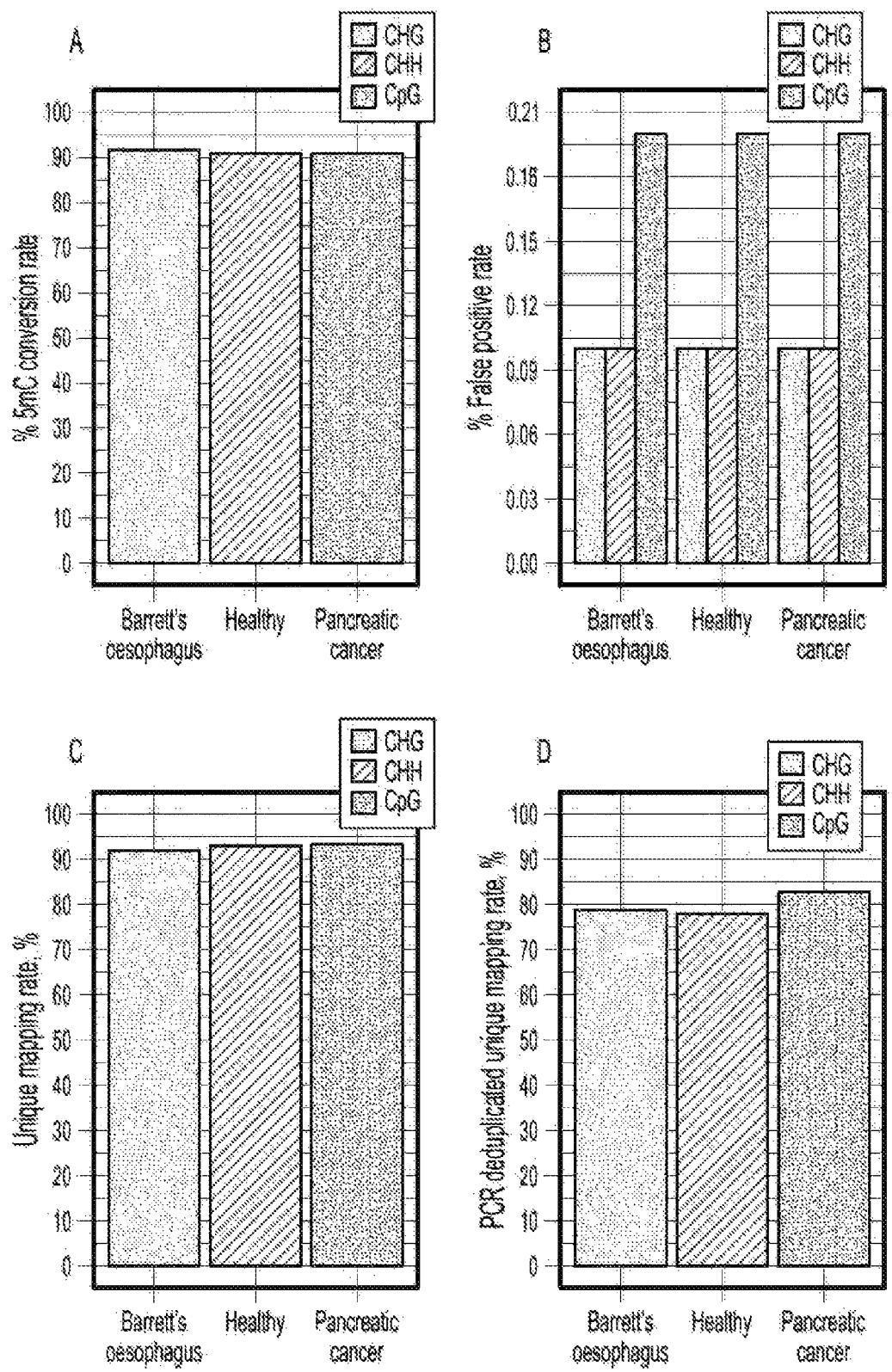
FIG. 26A-D. High-quality cell-free DNA TAPS. (A) Conversion rate of 5mC in TAPS-treated cfDNA. (B) False positive rate in TAPS-treated cfDNA. (C) Fraction of all sequenced read pairs that were uniquely mapped to the genome. (D) Fraction of all sequenced read pairs that were uniquely mapped to the genome and after removal of PCR duplication reads. CHG and CHH are non-CpG contexts.

TAPS was tested on three circulating cell-free DNA samples (cfDNA) from one healthy sample, one Barrett's oesophagus (Barrett's) sample, and one pancreatic cancer sample that were obtained from 1-2 ml of plasma. Standard TAPS protocol was followed and each sample sequenced to ~10× coverage. Analysis of the cfDNA TAPS results showed that TAPS provided the same high-quality methylome sequencing from low-input cfDNA as from bulk genomic DNA, including high 5mC conversion rate (FIG. 26A), low false positive rate (conversion of unmodified cytosine, FIG. 26B), high mapping rate (FIG. 26C), and low PCR duplication rate (FIG. 26D). These results demonstrate the power of TAPS for disease diagnostics from cfDNA.

Figure 27:
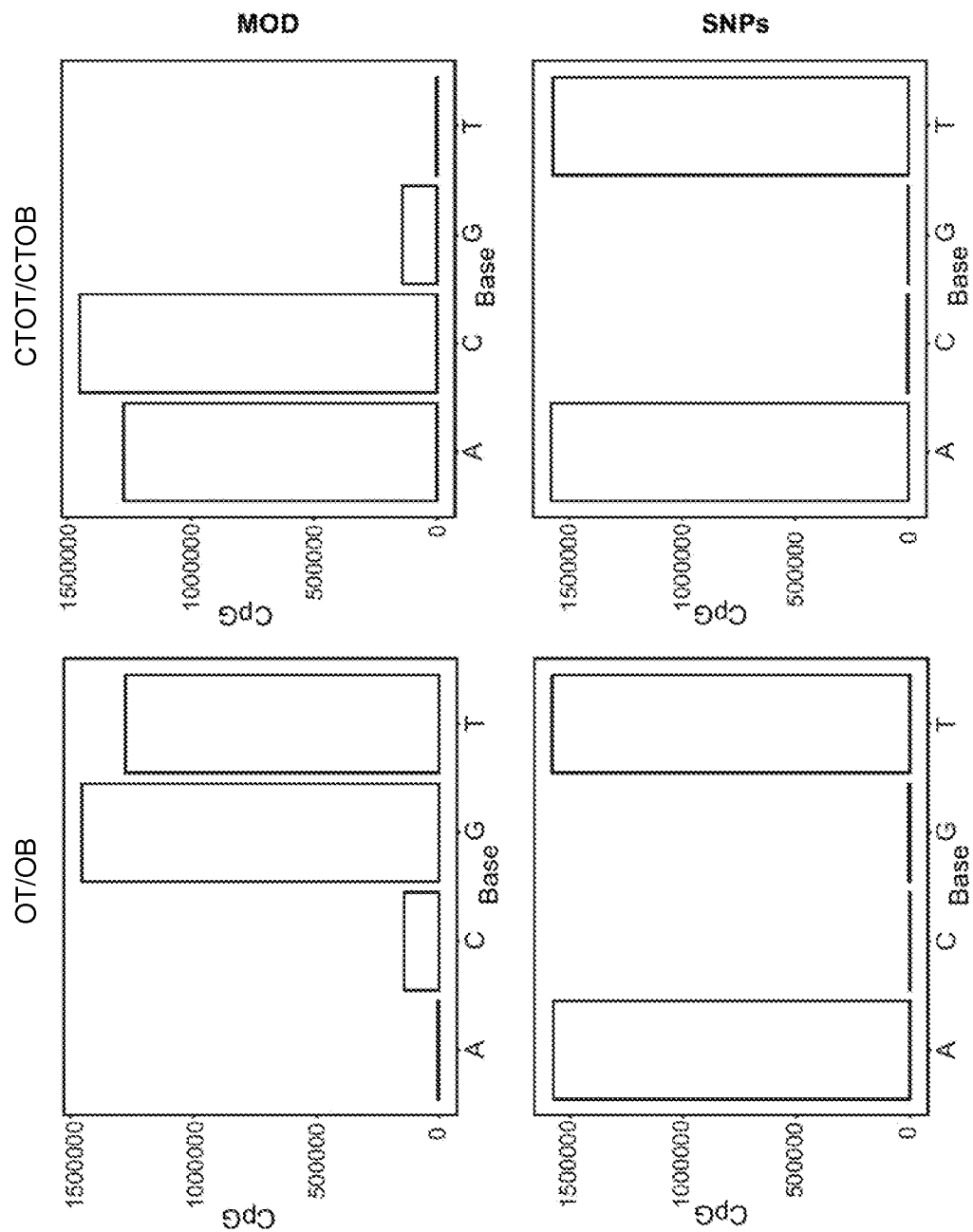
FIG. 27. TAPS can detect genetic variants. Methylation (MOD, top row) and C-to-T SNPs (bottom row) showed distinct base distribution patterns in original top strand (OT)/original bottom strand (OB), left column, and in strands complementary to OT (CTOT) and OB (CTOB), right column.

TAPS can also differentiate methylation from C-to-T genetic variants or single nucleotide polymorphisms (SNPs), therefore could detect genetic variants. Methylations and C-to-T SNPs result in different patterns in TAPS: methylations result in T/G reads in original top strand (OT)/original bottom strand (OB) and A/C reads in strands complementary to OT (CTOT) and OB (CTOB), whereas C-to-T SNPs result in T/A reads in OT/OB and (CTOB/CTOT) (FIG. 27). This further increases the utility of TAPS in providing both methylation information and genetic variants, and therefore mutations, in one experiment and sequencing run. This ability of the TAPS method disclosed herein provides integration of genomic analysis with epigenetic analysis, and a substantial reduction of sequencing cost by eliminating the need to perform standard whole genome sequencing (WGS).

In summary, we have developed a series of PS-derived bisulfite-free, base-resolution sequencing methods for cytosine epigenetic modifications and demonstrated the utility of TAPS for whole-methylome sequencing. By using mild enzymatic and chemical reactions to detect 5mC and 5hmC directly at base-resolution with high sensitivity and specificity without affecting unmodified cytosines, TAPS out performs bisulfite sequencing in providing a high quality and more complete methylome at half the sequencing cost. As such TAPS could replace bisulfite sequencing as the new standard in DNA methylcytosine and hydroxymethylcytosine analysis. Rather than introducing a bulky modification on cytosines in the bisulfite-free 5fC sequencing method reported recently (B. Xia et al., Bisulfite-free, base-resolution analysis of 5-formylcytosine at the genome scale. *Nat. Methods* 12, 1047-1050 (2015); C. Zhu et al., Single-Cell 5-Formylcytosine Landscapes of Mammalian Early Embryos and ESCs at Single-Base Resolution. *Cell Stem Cell* 20, 720-731 (2017)), TAPS converts modified cytosine into DHU, a near natural base, which can be "read" as T by common polymerases and is potentially compatible with PCR-free DNA sequencing. TAPS is compatible with a variety of downstream analyses, including but not limit to, pyrosequencing, methylation-sensitive PCR, restriction digestion, MALDI mass spectrometry, microarray and whole-genome sequencing. Since TAPS can preserve long DNA, it can be extremely valuable when combined with long read sequencing technologies, such as SMRT sequencing and nanopore sequencing, to investigate certain difficult to map regions. It is also possible to combine pull-down methods with TAPS to further reduce the sequencing cost and add base-resolution information to the low-resolution affinity-based maps. Herein, it was demonstrated that TAPS could directly replace WGBS in routine use while reducing cost, complexity and time required for analysis. This could lead to wider adoption of epigenetic analyses in academic research and clinical diagnostics.

Example 2: Endonuclease Enrichment TAPS (eeTAPS)

Methods
Preparation of Spike-In Controls.

A 4 kb spike-in control was prepared by PCR amplification of the pNIC28-Bsa4 plasmid (Addgene, cat. no. 26103) in a reaction containing 1 ng DNA template, 0.5 µM primers and 1× Phusion High-Fidelity PCR Master Mix with HF Buffer (Thermo Scientific). Primer sequences are listed in Table 10. The PCR product was purified by Zymo-IC column (Zymo Research) and methylated by HpaII Methyltransferase (New England Biolabs) for 2 h at 37° C. in a 50 µL reaction. Methylated product was purified with 1× Ampure XP beads (Beckman Coulter) according to the manufacturer's protocol. Fully CpG-methylated λ-DNA was prepared by methylation of unmethylated λ-DNA (Promega) with M.SssI enzyme (New England Biolabs) as described previously (Wu, H., Wu, X. J. and Zhang, Y. (2016) Base-resolution profiling of active DNA demethylation using MAB-seq and caMAB-seq. *Nat Protoc,* 11:1081-1100).

Preparation of Carrier DNA

Carrier DNA was prepared by PCR amplification of the pNIC28-Bsa4 plasmid (Addgene, cat. no. 26103) in a reaction containing 1 ng DNA template, 0.5 µM primers and 1× Phusion High-Fidelity PCR Master Mix with HF Buffer (Thermo Scientific). Primer sequences are listed in Table 10. The PCR product was purified by Zymo-IC column (Zymo Research), fragmented by Covaris M220 and purified on 0.9× Ampure XP beads to select for 200-500 bp fragments.

TABLE 10

Primer sequences used to amplify 4 kb spike-in model DNA and carrier DNA

| Template | Primer | Sequence (5' to 3') |
|---|---|---|
| 4 kb model DNA | 4 kb-F | CATCGAGCATCA AATGAAACTGC |
|  | 4 kb-R | ACGTTATACGAT GTCGCAGAGT |
| Carrier 2 kb | Carrier 2 kb-F | AGGCAACTTTAT GCCCATGCAA |
|  | Carrier 2 kb-R | CCAAGGGGTTAT GCTAGTTATTGC | mESCs Culture and Isolation of Genomic DNA.

E14 mESCs were cultured on gelatin-coated plates in DMEM (Invitrogen) supplemented with 15% FBS (Gibco), 2 mM 1-glutamine (Gibco), 1% nonessential amino acids (Gibco), 1% penicillin/streptavidin (Gibco), 0.1 mM β-mercaptoethanol (Sigma), 1,000 unitsml-1 leukemia inhibitory factor (Millipore), 1 µM PD0325901 (Stemgent) and 3 µM CHIR99021 (Stemgent). Cultures were maintained at 37° C. and 5% CO2 and passaged every 2 days. For isolation of genomic DNA, cells were harvested by centrifugation for 5 min at 1,000 g and room temperature. DNA was extracted with Quick-DNA Plus kit (Zymo Research) according to the manufacturer's protocol.

Expression and Purification of mTet1CD

The expression and purification of mTet1 catalytic domain (mTet1CD) were done as described above.

mTet1CD Oxidation.

200 ng of mESCs gDNA spiked-in with 0.5% of methylated λ-DNA and 0.025% of unmodified 2 kb DNA control were oxidised in 50 µl reaction containing 50 mM HEPES buffer (pH 8.0), 100 µM ammonium iron(II) sulfate, 1 mM α-ketoglutarate, 2 mM ascorbic acid, 1 mM dithiothreitol, 100 mM NaCl, 1.2 mM ATP and 4 µM mTet1CD for 80 min at 37° C. After that, 0.8 U of Proteinase K (New England Biolabs) were added to the reaction mixture and incubated for 1 h at 50° C. The product was cleaned up on Bio-Spin P-30 Gel Column (Bio-Rad) and 1.8× Ampure XP beads following the manufacturer's instruction.

Screening for DHU Digesting Endonucleases

1 µg mESC gDNA was enzymatically oxidised by mTet1CD as described above. Subsequently, oxidized DNA in 35 µl of water was reduced in a 50 µl reaction containing 600 mM sodium acetate solution (pH 4.3) and 1 M pyridine borane for 16 h at 37° C. and 850 r.p.m. in an Eppendorf ThermoMixer. The product was purified using Zymo-Spin columns. 40 ng of TAPS converted or unconverted DNA were then digested by the following enzymes according to the manufacturers' protocols (all from New England Biolabs): USER (Cat. No. M5505S), Endonuclease IV (Cat. No. M0304S), Tma Endonuclease III (Cat. No. M0291S), Endonuclease V (Cat. No. M0305S), UDG (Cat. No. M0280S), Tth Endonuclease IV (Cat. No. M0294S), Fpg (Cat. No. M0240S), Endonuclease III (Nth) (Cat. No. M0268S), Endonuclease VIII (Cat. No. M0299S), APE1 (Cat. No. M0282S). Digestion products were purified on 1.8× Ampure XP beads following the manufacturer's instructions and 10 ng of each product were run on a 2% agarose gel.

eeTAPS mESC genomic DNA (200 ng, 50 ng, 10 ng or 1 ng) was spiked with 0.05% 4 kb control methylated in CCGG sequence context and oxidised by mTet1CD as described above. Subsequently, oxidized DNA samples in 35 μl of water were reduced in a 50 μl reaction containing 600 mM sodium acetate solution (pH 4.3) and 1 M pyridine borane for 16 h at 37° C. and 850 r.p.m. in an Eppendorf ThermoMixer. The product was purified using Zymo-Spin columns. Converted samples were digested in a 20 μL reaction containing 2 U of USER enzyme (New England Biolabs) in CutSmart buffer for 1 h at 37° C. and size-selected on 0.35×-1× Ampure XP beads. End-repair and A-tailing reactions, and ligation of Illumina Multiplexing adapters were prepared with KAPA HyperPrep kit according to the manufacturer's protocol. To prepare the control library, 200 ng of unconverted mESC gDNA with spike-in controls was digested by USER enzyme, size-selected and used for library construction as described above. The final sequencing libraries were amplified with KAPA HiFi HotStart ReadyMix for 6 cycles (for 200 ng input), 8 cycles (50 ng input), 10 cycles (10 ng input) or 14 cycles (1 ng input) and size-selected on 0.35×-1× Ampure XP beads. Final libraries were paired-end 80 bp sequenced on a NextSeq 500 sequencer (Illumina) together with other sequencing libraries.

rrTAPS

One μg mESC gDNA was spiked with 1% CpG-methylated lambda and digested by Fast digest Msp1 enzyme (Thermo Scientific) in 50 μL reaction for 30 min at 37° C. Digested DNA was purified by the phenol/chloroform precipitation method. End-repair and A-tailing reactions, and ligation of Illumina Multiplexing adapters were prepared with NEBNext® Ultra™ II DNA Library Prep Kit according to the manufacturer's protocol. The ligated library was then purified on 1.6× Ampure XP beads and run on a 1% agarose gel. DNA fragments from 100-400 bp were excised and purified by Monarch® DNA Gel Extraction Kit following the manufacturer's protocol. The adapter-ligated sample was spiked with 100 ng of carrier DNA and double oxidised by mTet1CD as described above. Oxidized DNA in 35 μl of water was reduced in a 50 μl reaction containing 600 mM sodium acetate solution (pH 4.3) and 1 M pyridine borane for 16 h at 37° C. and 850 r.p.m. in an Eppendorf ThermoMixer. The product was purified using Zymo-Spin columns. The final sequencing library was amplified with KAPA HiFi Uracil (+) Master Mix for 6 cycles and purified on 1× Ampure XP beads. Final libraries were paired-end 80 bp sequenced on a NextSeq 500 sequencer (Illumina) together with other sequencing libraries.

Data Analysis for eeTAPS

Raw sequenced reads were processed with TrimGalore (https://www.bioinformatics.babraham.ac.uk/projects/trim_galore/) to perform adapter and quality trimming with the following parameters: --paired --length 35. Cleaned reads were aligned using bwa mem 0.7.17-r1188 (Li, H. and Durbin, R. (2009) Fast and accurate short read alignment with Burrows-Wheeler transform. Bioinformatics, 25, 1754-1760) with default parameters. For the 4 kb model DNA, the pNIC28-Bsa4 sequence from 2,627 to 6,911 was used as reference. For mESC gDNA, the mm9 genome was used as reference. Only properly mapped read pairs (Read 1 with flag assigned as 83 or 99) were extracted to compute coverage with bedtools v2.27.1 (Quinlan, A. R. and Hall, I. M. (2010) BEDTools: a flexible suite of utilities for comparing genomic features. Bioinformatics, 26, 841-842) for both endpoints and read-through of the whole fragments, and un-cleaved sites were also taken into consideration when calculating the cleavage fraction. The detailed computational pipeline to analyze eeTAPS can be found here https://gitlab.com/jfeicheng/userenrich. Two technique replicates were sequenced for eeTAPS. When analyzing the effect of sequence depth on eeTAPS, the alignment files from two replicates were merged and then sub-sampled by fraction from 0.1 to 1 with samtools view (Li, H., Handsaker, B., Wysoker, A., Fennell, T., Ruan, J., Homer, N., Marth, G., Abecasis, G., Durbin, R. and Genome Project Data Processing, S. (2009) The Sequence Alignment/Map format and SAMtools. Bioinformatics, 25, 2078-2079).

Data Analysis for rrTAPS

Raw sequenced reads were processed with seqtk (https://github.com/lh3/seqtk) trimfq -b 2 to trim 2 bp from the left of each read. Astair 3.2.7 was used to process rrTAPS (8). Cleaned reads were aligned using astair align with mm9 genome as reference. Methylated CpGs were extracted with astair call.

Comparison of wgTAPS, eeTAPS and rrTAPS in mESC wgTAPS data were downloaded from GSE112520 (Liu, Y. B., Siejka-Zielinska, P., Velikova, G., Bi, Y., Yuan, F., Tomkova, M., Bai, C. S., Chen, L., Schuster-Bockler, B. and Song, C. X. (2019) Bisulfite-free direct detection of 5-methylcytosine and 5-hydroxymethylcytosine at base resolution. Nat Biotechnol, 37, 424-429). Only CpG sites covered with at least 4 reads were considered as covered CpG sites. The number of methylated CpG sites was defined according to the following criteria: CpG methylation level >1st quartile of all CpG methylation level (0.5 for wgTAPS and 0.28 for eeTAPS). The genome was divided into non-overlapping 100 kb windows with bedtools. The CpG island track was downloaded from http://hgdownload.soe.ucsc.edu/goldenPath/mm9/database/cpgIslandExt.txt.gz. The gene annotation file was downloaded from http://hgdownload.soe.ucsc.edu/goldenPath/mm9/database/refGene.txt.gz. For wgTAPS, the average methylation was used to assign methylation in each window. For eeTAPS, CpG sites with cleavage fraction higher than 0.28 were designated as methylated, while sites below this cutoff were designated as unmethylated, and the methylation level for each bin was thus measured as the # methylated CpG/(# methylated CpG+# unmethylated CpG). Expression data from the e14 mESC cell line was taken from GEO entry GSE72855 (Neri, F., Rapelli, S., Krepelova, A., Incarnato, D., Parlato, C., Basile, G., Maldotti, M., Anselmi, F. and Oliviero, S. (2017) Intragenic DNA methylation prevents spurious transcription initiation. Nature, 543, 72-77) and used to categorize genes into four groups according to their expression levels.

Results

Development of eeTAPS

Figure 28:
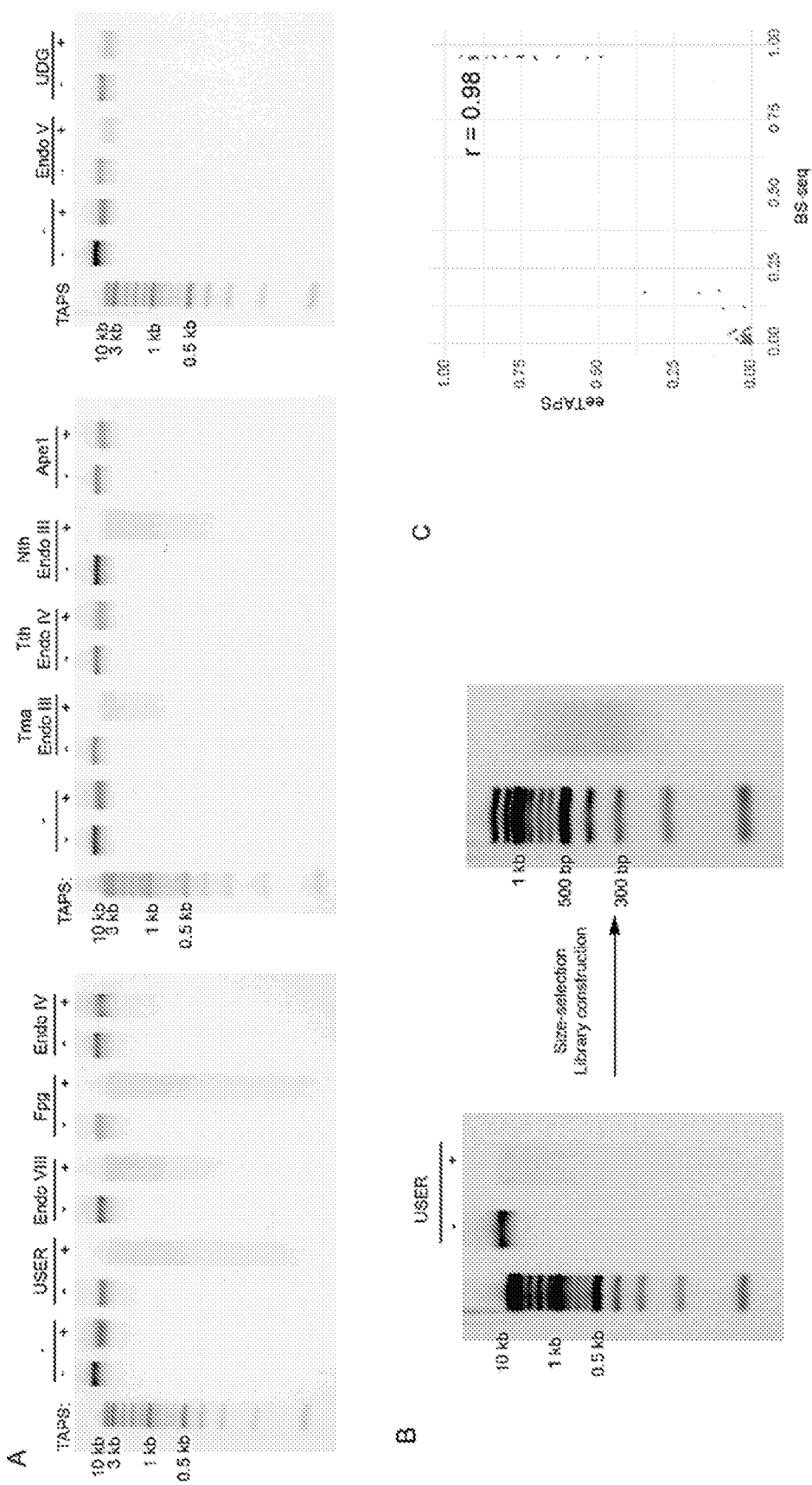
FIG. 28A-C. Endonuclease cleavage of TAPS conversion products. (A) Results of mESC gDNA digestion by different endonucleases before and after TAPS conversion. TAPS conversion introduces DHU in place of methylated cytosine. Endo VIII-endonuclease VIII, Endo IV-endonuclease IV, Tma Endo III-endonuclease III, Tth Endo IV-endonuclease IV; Nth Endo III-Nth endonuclease III; Endo V-Endonuclease V. (B) Representative image of TAPS-treated mESC gDNA before USER digestion, after USER digestion, and after size-selection. (C) Scatter plot showing the methylation level in all CpGs measured by both BS-seq and eeTAPS.

In order to enrich methylated CpG sites for sequencing following the TAPS reaction, endonucleases were identified that specifically cleave, the DHU containing product of TAPS. Ten commercially available endonucleases with known ability to digest DHU or structurally similar nucleotides (uracil, 5-hydroxymethyluracil, dihydrothymine) were tested. Nucleases including USER, Endonuclease VIII, Endonuclease III and Fpg cleaved TAPS-converted DNA, while others such as APE 1 and UDG did not substantially cleave TAPS-converted DNA (FIG. 28A). USER was selected because it showed the highest cleavage efficiency of TAPS-converted DNA with minimal impact on unconverted DNA (FIG. 28A).

Figure 29:
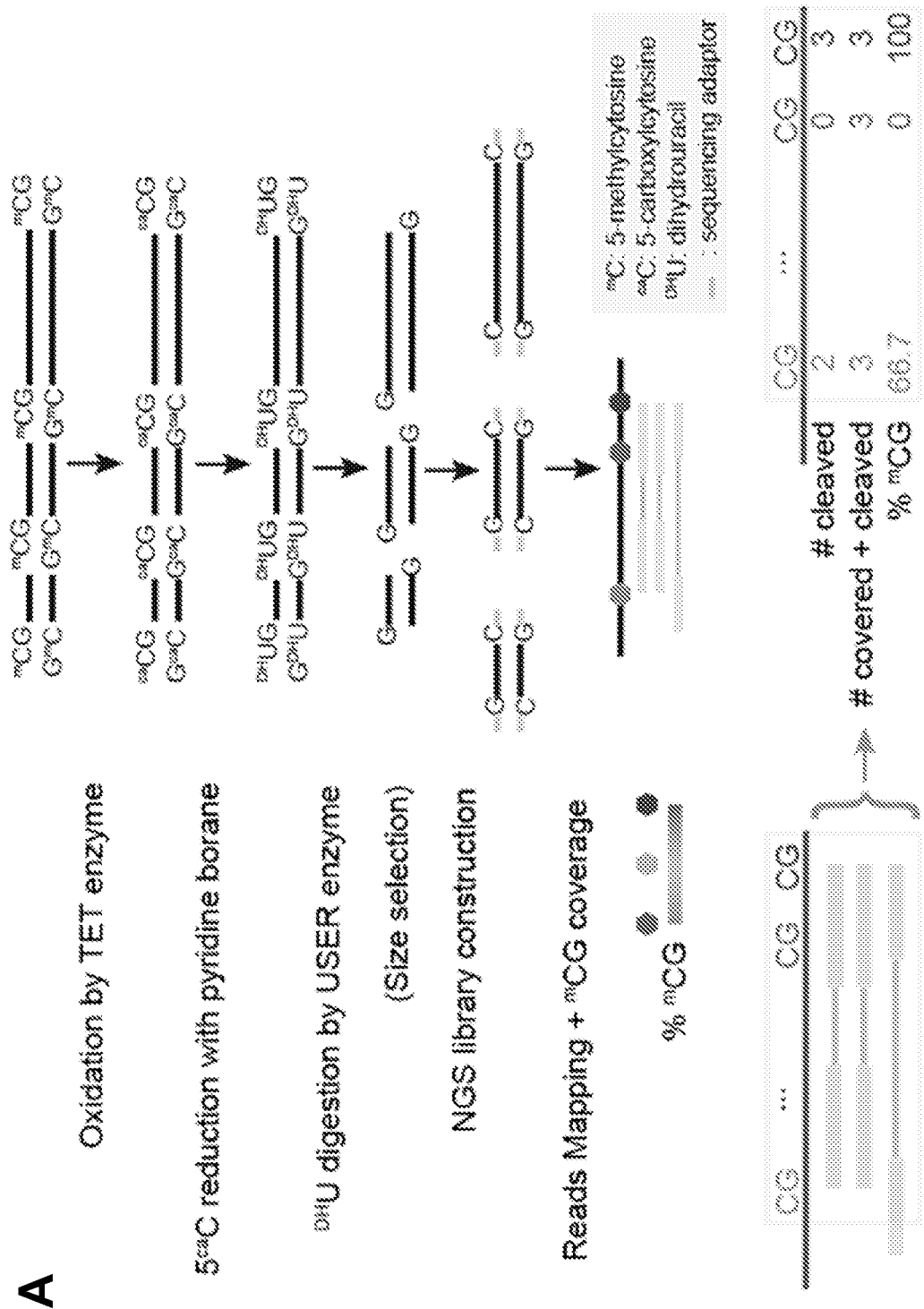
FIG. 29A-B. Endonuclease enrichment TAPS (eeTAPS). (A) Schematic of eeTAPS (top) and computational measurement of CG methylation level (bottom). 5-methylcytosine (mC) was first converted to dihydrouracil (DHU) with TAPS and then enriched through USER digestion. Size selected DNA fragments were then prepared into sequencing library and amplified by PCR. Following reads alignment, CG methylation level was then calculated as the number of reads that are cleaved at each CpG site divided by the total number of reads cleaved at or covering each CpG site. (B) Validation of eeTAPS on a 4 kb model DNA. The tracks from top to bottom indicate the methylation level measured in bisulfite sequencing (BS-seq), eeTAPS and a control for eeTAPS. In the eeTAPS control, USER enzyme was used to digest DNA without TAPS conversion.
Figure 29:

TAPS conversion was then combined with USER digestion to enrich methylated sequences. First, un-fragmented genomic DNA (gDNA) from mouse embryonic stem cells (mESCs) was converted with TAPS and digested with USER. Cleavage resulted in DNA fragments ranging from 100 bp to 10 kb (FIG. 28B). Presumably, the shorter fragments correspond to densely methylated regions and the long fragments correspond to sparsely methylated parts of the genome. The fragmented DNA was size selected to retain fragments of 200 bp-1 kb to represent moderate methylation status and prepared an Illumina sequencing library (FIG. 29A, FIG. 28B). To identify and quantify methylated CpG sites, a computational pipeline was developed. The methylation level was calculated as the number of reads that are cleaved at each CpG site divided by the total number of reads cleaved at or covering each CpG site (FIG. 29A).

Figure 31:
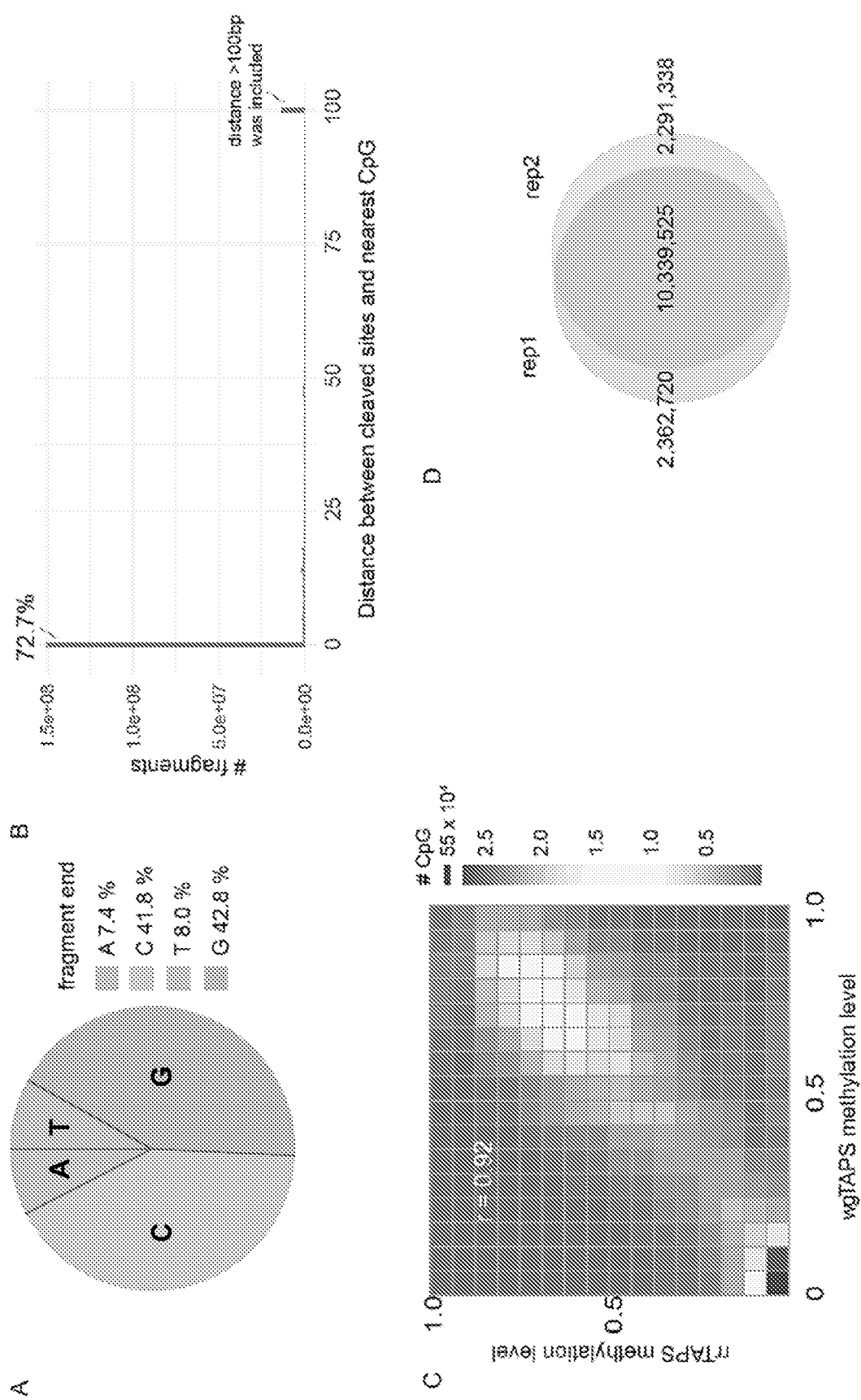
FIG. 31A-D. (A) Nucleotide frequency at the ends of the sequenced fragments. (B) Bar plot showing the distribution of distance between cleaved sites and its nearest CpG. (C) Heatmap showing the correlation of methylation level determined by wgTAPS and rrTAPS at single CpG-resolution. The methylation level was divided into 16 group for both wgTAPS and rrTAPS. The colour shows the number of CpGs in specific intervals. Only sites with wgTAPS coverage >5 and rrTAPS coverage >5 were taken into consideration. The Pearson correlation coefficient is 0.92. (D) Overlap of mCpG sites detected in replicates of eeTAPS, replicates were sub-sampled to the same depth to detect mCpG.

To evaluate the performance of eeTAPS, a 4 kb spike-in model DNA was prepared with all CpGs in CCGG sites methylated by HpaII methyltransferase, which also generated some low-level CpG methylation in off-target non-CCGG sites. Excellent agreement was obtained between eeTAPS methylation and bisulfite methylation in the model DNA mESCs gDNA (Table 11). eeTAPS is proposed to be a cost-efficient methodology since it will enrich methylated CpGs. Indeed, we found that 84.6% of fragments in eeTAPS end with C/G (FIG. 31A). Further analysis on the distance between cleaved sites and the nearest CpG identified that 72.7% of cleaved events occurred on CpG (FIG. 31B).

Figure 30:
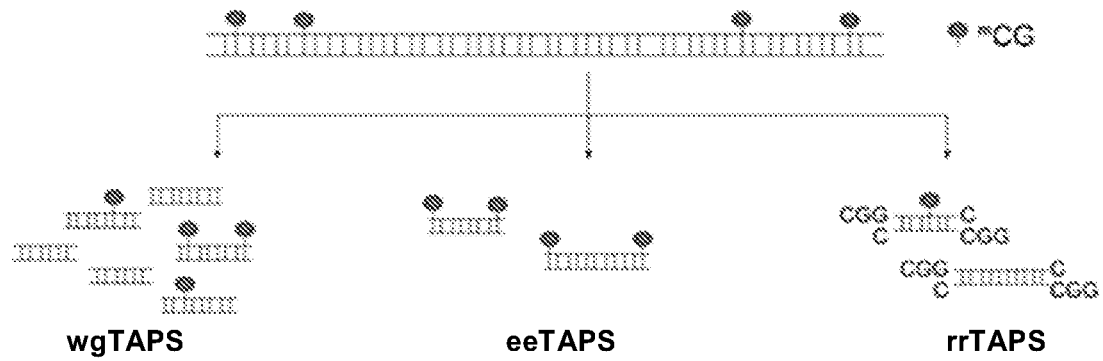
FIG. 30A-D. Comparison of wgTAPS, eeTAPS and rrTAPS on mESC DNA. (A) Diagram showing the genomic fragmentation method for wgTAPS, eeTAPS and rrTAPS. In wgTAPS, genomic DNA is randomly fragmented, while for eeTAPS and rrTAPS, fragmentation happens specifically at methylated CpG (mCG) sites and CCGG sites respectively. (B) Barplot showing the percentage of covered CpG sites covered by wgTAPS, eeTAPS and rrTAPS overlapping with different chromatin features. The chromatin features were defined in previous study (20). (C) Heatmap showing the correlation of methylation level determined by wgTAPS and eeTAPS at single CpG-resolution. The methylation level was divided into 16 group for both wgTAPS and eeTAPS. The colour shows the number of CpGs in specific intervals. Only sites with wgTAPS coverage >5 were taken into consideration. Pearson correlation coefficient is shown on the top of the plot. (D) Venn plot showing the overlap of detected mCpG sites in wgTAPS, rrTAPS and eeTAPS. CpG sites with methylation level >1st quartile of methylation level were defined as methylated CpGs in both wgTAPS and eeTAPS. In rrTAPS, the same methylation cut-off was used as in wgTAPS. (CpG sites with methylation level >0.5 in wgTAPS and rrTAPS were defined as mCpG, CpG sites with methylation level >0.28 in eeTAPS were defined as mCpG).
Figure 30:
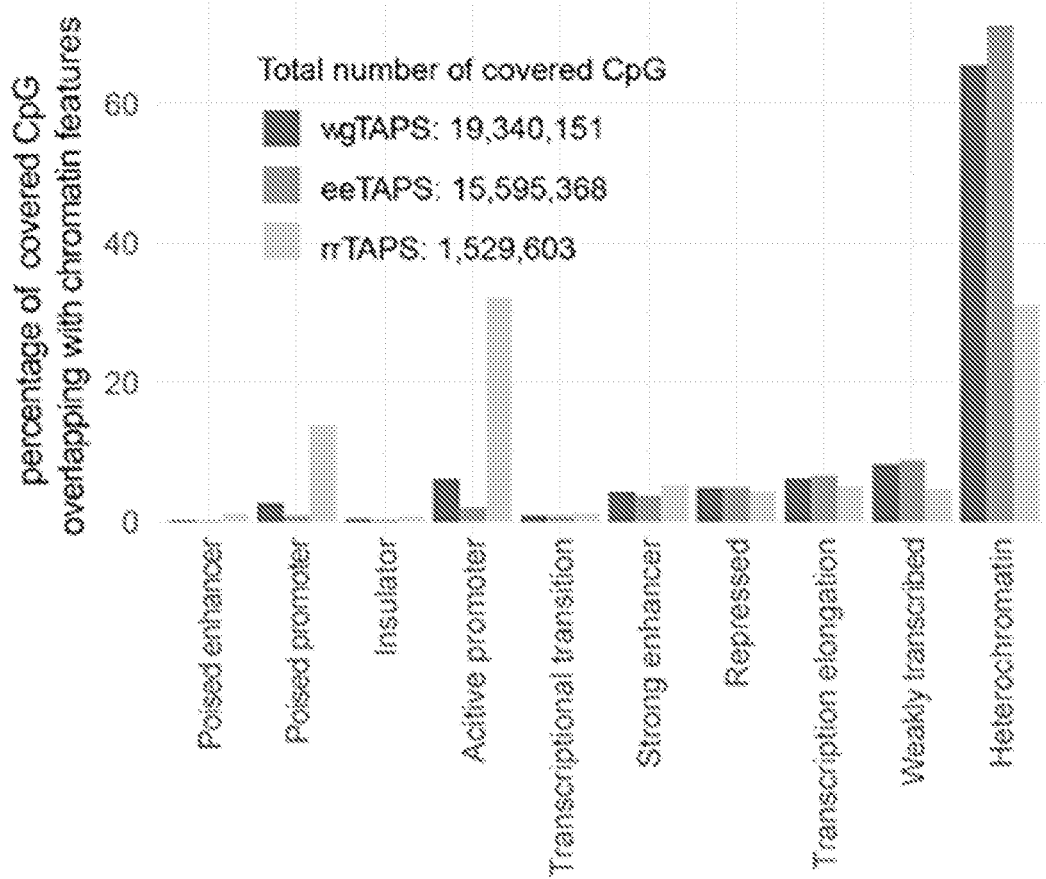
Figure 30:
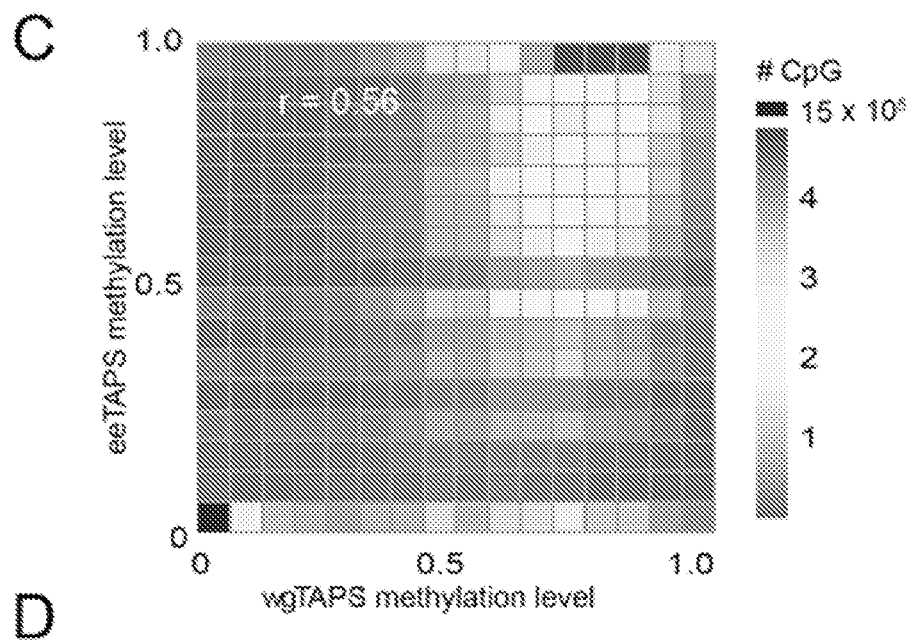
Figure 30:
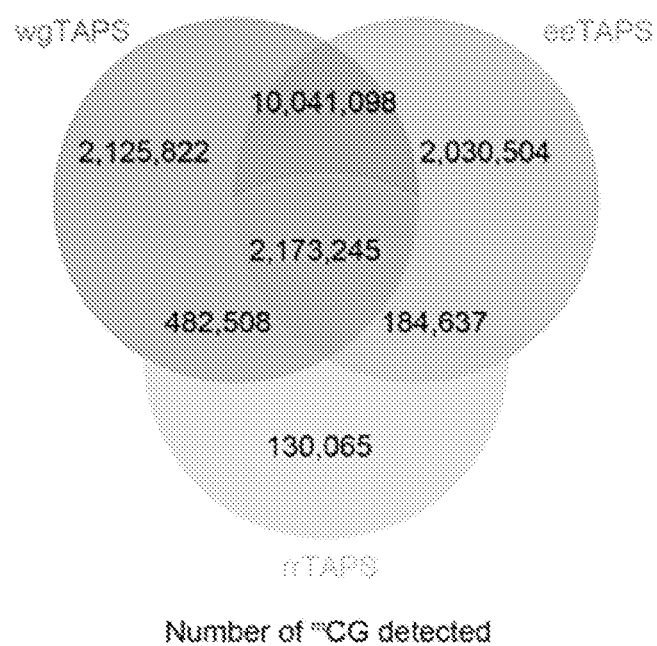

To further illustrate this point, eeTAPS was compared with wgTAPS and rrTAPS (FIG. 30A, Table 11). First, the number of CpG sites that are covered in all three methods was compared (CpG with coverage >3 were regarded as covered CpGs). wgTAPS and eeTAPS covered the majority of CpG sites (19.3M and 15.2M sites respectively; 92.1% and 74.2% of total CpG respectively), while rrTAPS only covered ~1.5M sites (7.2% of total CpG) (FIG. 30B). To further compare the genomic regions covered by these assays, the covered sites were mapped to different genomic regions (Bogu, G. K., Vizan, P., Stanton, L. W., Beato, M., Di Croce, L. and Marti-Renom, M. A. (2015) Chromatin and RNA Maps Reveal Regulatory Long Noncoding RNAs in Mouse. Mol Cell Biol, 36, 809-819). Intergenic methylation such as those in distal regulatory elements are also known to be important for gene regulation. We found that wgTAPS and eeTAPS share a similar broad feature distribution, with the majority of covered CpG sites lying in heterochromatin (65.6% and 71%, respectively), while rrTAPS is biased towards promoter regions (46% of covered CpG) (FIG. 30B). At single-CpG resolution, eeTAPS and wgTAPS showed good correlation (r=0.56, FIG. 30C), while rrTAPS and wgTAPS showed excellent correlation (r=0.92, FIG. 31C). eeTAPS overestimates methylation, which is likely due to the fact that DNA fragments with unmethylated CpGs will be longer and less well amplified.

TABLE 11

Mapping statistics for eeTAPS, wgTAPS, and rrTAPS

| sample | # Raw reads | # mapped reads | # properly reads | % mapped reads | % properly reads | sequencing depth |
|---|---|---|---|---|---|---|
| Mapping statistics for eeTAPS | | | | | | |
| eeTAPS | 75,087,691 | 74,487,124 | 67,849,413 | 99.20% | 90.30% | 4.525209 |
| eeTAPS (1 ng) | 25,488,766 | 25,433,543 | 15,727,887 | 99.70% | 61.70% | 1.536097 |
| eeTAPS (10 ng) | 22,371,125 | 22,327,287 | 20,824,202 | 99.80% | 93.00% | 1.348211 |
| eeTAPS (50 ng) | 28,370,411 | 28,315,992 | 27,475,285 | 99.80% | 96.80% | 1.709762 |
| eeTAPS (rep) | 107,627,064 | 107,376,184 | 103,168,329 | 99.70% | 95.80% | 6.486216 |
| eeTAPS (ctrl) | 9,568,590 | 9,546,719 | 9,232,041 | 99.70% | 96.40% | 0.576657 |
| Mapping statistics for wgTAPS and rrTAPS | | | | | | |
| rrTAPS | 41,956,461 | 37,017,706 | 36,401,314 | 88.2% | 86.0% | 2.528534 |

(Pearson correlation coefficient (r)=0.98) (FIG. 28C), supporting the power of eeTAPS in quantifying DNA methylation level (FIG. 29B). On the other hand, in a control sample where USER enzyme was used to digest non-TAPS converted 4 kb model DNA, none of the CpGs were detected with significant methylation (FIG. 29B), which indicates the high specificity of eeTAPS in detecting methylation. Together, these results demonstrated that eeTAPS could accurately inform DNA methylation status in the 4 kb model DNA.

eeTAPS on mESC

Having demonstrated the ability for eeTAPS on model DNA, eeTAPS was utilized to profile CpG methylation in Next, the methylated CpG sites that are covered in different assays was compared. eeTAPS and wgTAPS show high agreement in terms of the sites that are defined as methylated CpG (mCpG) sites (82.4% mCpG sites detect by wgTAPS are also detect by eeTAPS, FIG. 30D), while rrTAPS only detect about 20.0% of mCpG (FIG. 30D). Furthermore, eeTAPS showed high reproducibility with 81% mCpG observed in the replicates (FIG. 31D). Collectively, these analyses support that eeTAPS can accurately and robustly detect mCpG sites at a whole-genome scale and can be a powerful semi-quantitative tool for measuring methylation at single-CpG resolution.

Comparison of eeTAPS and wgTAPS on Genomic Features

Figure 32:
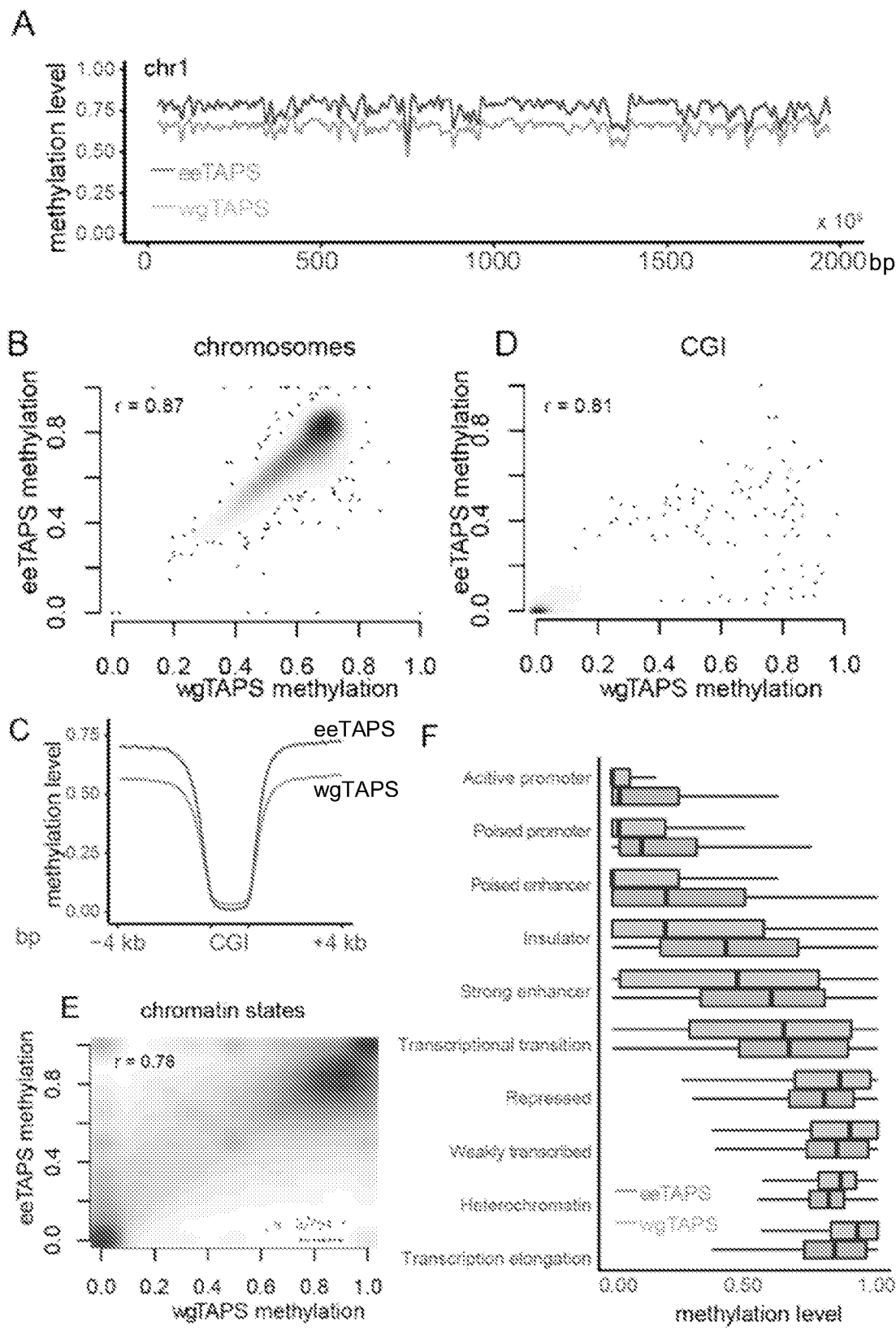
FIG. 32A-F. Methylation profiling in different genomic features with eeTAPS.

The methylation pattern across different genomic features was compared between eeTAPS and wgTAPS. To quantify methylation level in a region, average methylation was used in wgTAPS, and the fraction of methylated CpGs compared to the total number of CpG sites detected was used in eeTAPS. eeTAPS and wgTAPS showed highly correlated chromosome-wide methylation patterns although eeTAPS overestimated the methylation level (FIG. 32A, B). CpG islands (CGIs) are known to be depleted of DNA methylation, and these are reflected in both eeTAPS and wgTAPS (FIG. 32C). Correlation of the methylation level on CGIs measured using eeTAPS and wgTAPS was 0.81, which further indicates that eeTAPS can accurately capture the CpG methylation state in various features (FIG. 32D).

Previous studies reveal that DNA methylation in promoter regions is generally anti-correlated with gene expression. We categorised genes into 4 group according to their expression levels and plotted the average methylation from 4 kb upstream of the transcription start site (TSS) to 4 kb downstream. Using both eeTAPS and wgTAPS we found that highly expressed genes tend to have lower methylation levels, while genes with lower expression levels have higher methylation levels (FIG. 33). We also compared the methylation distribution in different chromatin features as defined previously (Bogu, G. K., Vizan, P., Stanton, L. W., Beato, M., Di Croce, L. and Marti-Renom, M. A. (2015) Chromatin and RNA Maps Reveal Regulatory Long Noncoding RNAs in Mouse. Mol Cell Biol, 36, 809-819) (FIG. 32E, F). Consistent with previous research, heterochromatin regions are highly methylated while promoter regions in euchromatin are normally depleted of CG methylation (FIG. 32F).

Application of eeTAPS on Low-Input Samples

Figure 34:
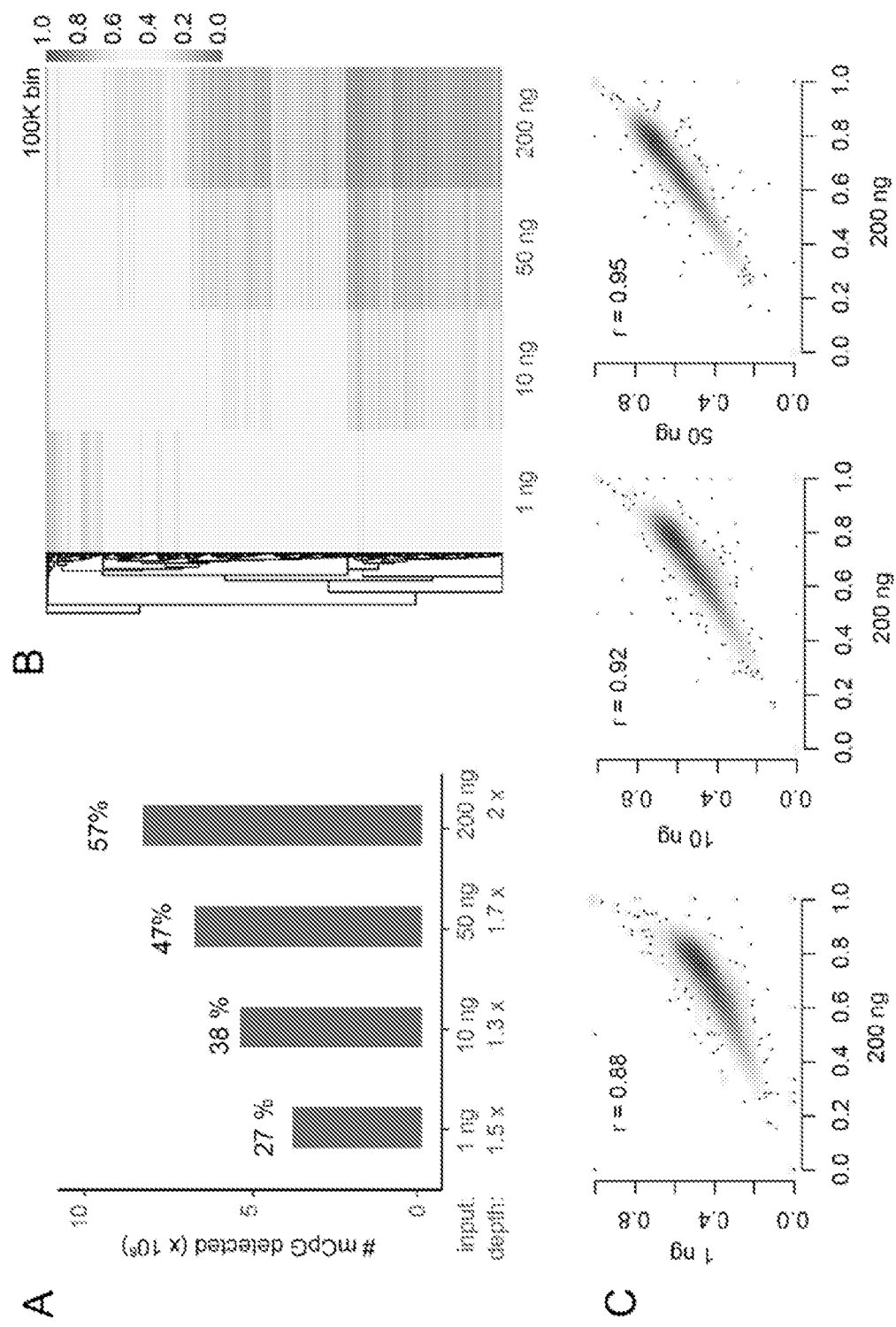

To evaluate the performance of eeTAPS on low-input samples, we applied it to 1 ng, 10 ng, and 50 ng mESC gDNA respectively. For 200 ng mESC DNA sample, sequencing reads were down-sampled to 2× to match the sequencing depth of low-input samples. We found that 27% of the mCpG sites identified by wgTAPS are also recovered using 1 ng DNA in eeTAPS. The percentage increased to 47% when 50 ng mESC DNA was used (FIG. 34A). To further compare the whole genome methylation profile with these low-input samples, we binned the genome into 100 kb windows and computed the average methylation level within each bin (FIG. 34B). A highly consistent methylation profile was observed among these low-input samples (with r=0.88, 0.92 and 0.95 for 1 ng, 20 ng, and 50 ng respectively compared to 2×200 ng eeTAPS, FIG. 34C), thus further indicating the feasibility of eeTAPS application to low-input DNA samples.

Effect of Sequencing Depth on eeTAPS

To assess the effect of sequencing depth on the total number of mCpG sites that can be detected, we down-sampled eeTAPS and evaluated the performance. The total number of detected mCpG sites increased with deeper sequencing (FIG. 35A). Nonetheless, with 4× (70 M reads) sequencing depth, 74% mCpG sites could be successfully detected (among the 14.9 M mCpG sites detected in wgTAPS, 10.9 M sites were also defined as mCpG in 4× eeTAPS). A similar trend was observed in terms of the methylation correlation across chromosomes and CGIs (FIG. 35B), and Pearson correlation coefficients in CGIs reached 0.83 for 4× coverage (FIG. 35B). Thus, we demonstrated that eeTAPS can accurately provide a global methylation profile at a reduced sequencing cost compared to WGBS.

Discussion wgTAPS could provide the most comprehensive quantitative and base-resolution whole-genome methylation. However, the steep cost of whole-genome sequencing and the large amount of data produced still limits its broad application in many projects. Methylated CpG sites constitute a minor fraction in mammalian genomes, therefore, whole genome sequencing is not the most data-efficient approach to learn about methylation status. A cost-efficient approach would be to specifically select only the regions containing methylated CpGs for further analysis by sequencing. Reduced-representation sequencing based on restriction enzyme digestion enrichment of CpG-rich regions and subsequent bisulfite sequencing is a cost-effective approach for methylome analysis; however, this method only covered a small proportion of CpG sites in the genome (Meissner, A., Gnirke, A., Bell, G. W., Ramsahoye, B., Lander, E. S. and Jaenisch, R. (2005) Reduced representation bisulfite sequencing for comparative high-resolution DNA methylation analysis. Nucleic Acids Res, 33, 5868-5877). TAPS is compatible with the reduced-representation approach, and we have demonstrated rrTAPS can accurately quantify methylation in a subset of the genome, especially in CGIs. Aside from the well-established biological implication of CpG methylation in gene promoters, extensive studies have also focused on intergenic DNA methylation for its potential involvement in cell fate commitment and tumorigenesis. To extend the enrichment approach to genome-wide CpG sites, we further utilized the advantage of TAPS to directly convert 5mC to DHU, which allowed DHU-sensitive endonuclease-induced cleavage at these specific modified bases. Through selective enrichment of these fragments coupled with sequencing, we demonstrated that eeTAPS enables the detection of CpG methylation on a genome-wide scale. Such a strategy is possible because of the direct detection of methylated cytosines by TAPS. Unlike traditional antibody-based enrichment method, eeTAPS offers the possibility of direct methylation detection at single CpG resolution.

We demonstrated that eeTAPS can be used to capture genome-wide methylation signatures at single-CpG resolution in a cost-effective manner, which fills the gap between rrTAPS and wgTAPS. The eeTAPS methylation profiles across multiple different genomic features correlated well with those obtained using wgTAPS. Further, with only 70 M reads, eeTAPS can detect 74% of the methylated CpG detected by wgTAPS. The potential limitations of eeTAPS, which arise from the variable spacing of methylated CpG sites, could be the semi-quantitative measurement of methylation level at single-CpG sites. In this study, we selected fragments of 200 bp-1 kb as a proof of concept. Nevertheless, the correlation coefficient between wgTAPS and eeTAPS was still as good as 0.56. Building on the mild nature of TAPS reaction, we further showed that eeTAPS is also a promising cost-effective protocol in methylation detection with low-input DNA samples.

The invention claimed is:

1. A method for cleaving a modified target DNA, the method comprising:
   converting 5-carboxylcytosine (5caC) and/or 5-formylcytosine (5fC) in a target DNA to dihydrouracil (DHU) with a borane reducing agent to provide a modified target DNA comprising one or more DHU; and
   contacting the modified target DNA comprising one or more DHU with one or more DHU-sensitive endonucleases that cleave the modified target DNA at, or adjacent to, the one or more DHU.

2. The method of claim 1, wherein the borane reducing agent is selected from the group consisting of pyridine borane, 2-picoline borane (pic-BH3), borane, sodium borohydride, sodium cyanoborohydride, and sodium triacetoxyborohydride.

3. The method of claim 1, wherein the one or more DHU-sensitive endonucleases are selected from one or more of the group consisting of a mixture of a combination of Uracil DNA glycosylase (UDG) and DNA glycosylase-lyase Endonuclease VIII, Endonuclease III, Tma Endonuclease III, Endonuclease VIII, and Formamidopyrimidine DNA Glycosylase (Fpg).

4. The method of claim 1, wherein the one or more DHU-sensitive endonucleases comprise a mixture of a combination of UDG and Endonuclease VIII.

5. The method of claim 1, further comprising the step of adding adapter DNA molecules to the cleaved modified target DNA.

6. The method of claim 1, further comprising detecting the sequence of the cleaved modified target DNA, wherein the presence of a cleavage site provides the location of either a 5caC or 5fC in the target DNA.

7. The method of claim 1, wherein:
   the borane reducing agent is selected from the group consisting of pyridine borane, 2-picoline borane (pic-BH3), borane, sodium borohydride, sodium cyanoborohydride, and sodium triacetoxyborohydride; and
   the one or more DHU-sensitive endonucleases are selected from one or more of the group consisting of a mixture of a combination of Uracil DNA glycosylase (UDG) and DNA glycosylase-lyase Endonuclease VIII, Endonuclease III, Tma Endonuclease III, Endonuclease VIII, and Formamidopyrimidine DNA Glycosylase (Fpg).

8. The method of claim 7, wherein the one or more DHU-sensitive endonucleases comprise a mixture of a combination of UDG and Endonuclease VIII.

* * * * *

SEQUENCE LISTING

<160> NUMBER OF SEQ ID NOS: 76

<210> SEQ ID NO 1
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
gtcgaccgga tc                                                          12

<210> SEQ ID NO 2
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
ttggatccgg tcgactt                                                     17

<210> SEQ ID NO 3
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
cctgatgaaa caagcatgtc                                                  20

<210> SEQ ID NO 4
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="Description of Combined DNA/RNA
      Molecule: Synthetic primer"

<400> SEQUENCE: 4
cautactcac utccccacut                                                  20

<210> SEQ ID NO 5
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
cccgacgcat gatctgtact tgatcgaccg tgcaac                                36

<210> SEQ ID NO 6
<211> LENGTH: 58

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
aatgatacgg cgaccaccga gatctacact ctttccctac acgacgctct tccgatct           58

<210> SEQ ID NO 7
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
gatcggaaga gcacacgtct gaactccagt cacgccaata tctcgtatgc cgtcttctgc           60
ttg                                                                          63

<210> SEQ ID NO 8
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 8
tcttccgauc gttgcacggu cgatcaagua cagatcatgc gucgggagau cggaag               56

<210> SEQ ID NO 9
<211> LENGTH: 157
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9
aatgatacgg cgaccaccga gatctacact ctttccctac acgacgctct tccgatctcc           60
cgacgcatga tctgtacttg atcgaccgtg caacgatcgg aagagcacac gtctgaactc          120
cagtcacgcc aatatctcgt atgccgtctt ctgcttg                                   157

<210> SEQ ID NO 10
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
aatgatacgg cgaccaccga g                                                      21

<210> SEQ ID NO 11
```

```
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
caagcagaag acggcatacg ag                                             22

<210> SEQ ID NO 12
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
agcagtctcg atcagctgct actgtacgta gcat                                34

<210> SEQ ID NO 13
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
aggtgcgcta agttctagat cgccaactgg ttgtggcctt                          40

<210> SEQ ID NO 14
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
ctatagccgg cttgctctct ctgcctctag cagctgctcc ctatagtgag tcgtattaac    60

<210> SEQ ID NO 15
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
atctagaact tagcgcacct agatcggaag agcgtcgtgt                          40

<210> SEQ ID NO 16
<211> LENGTH: 74
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
```
agagagcaag ccggctatag atgctacgta cagtagcagc tgatcaagac tgctaaggcc    60
acaaccagtt ggcg    74

<210> SEQ ID NO 17
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
agacgtgtgc tcttccgatc gttaatacga ctcactatag gg    42

<210> SEQ ID NO 18
<211> LENGTH: 255
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
aatgatacgg cgaccaccga gatctacact ctttccctac acgacgctct tccgatctag    60
gtgcgctaag ttctagatcg ccaactggtt gtggccttag cagtctcgat cagctgctac   120
tgtacgtagc atctatagcc ggcttgctct ctctgcctct agcagctgct ccctatagtg   180
agtcgtatta acgatcggaa gagcacacgt ctgaactcca gtcacgccaa tatctcgtat   240
gccgtcttct gcttg   255

<210> SEQ ID NO 19
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
tgctagaggc agagagagca ag    22

<210> SEQ ID NO 20
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: variation
<222> LOCATION: (9)..(9)
<223> OTHER INFORMATION: /replace="DHU" or "t" or "c"
<220> FEATURE:
<221> NAME/KEY: misc_feature
<222> LOCATION: (1)..(17)
<223> OTHER INFORMATION: /note="Variant nucleotides given in the
      sequence have no preference with respect to those in the
      annotations for variant positions"

```
<400> SEQUENCE: 20
agcagtctug atcagct                                                    17

<210> SEQ ID NO 21
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
gctactgtac gtagcat                                                    17

<210> SEQ ID NO 22
<211> LENGTH: 255
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: variation
<222> LOCATION: (107)..(107)
<223> OTHER INFORMATION: /replace="DHU" or "t" or "c"
<220> FEATURE:
<221> NAME/KEY: misc_feature
<222> LOCATION: (1)..(255)
<223> OTHER INFORMATION: /note="Variant nucleotides given in the
      sequence have no preference with respect to those in the
      annotations for variant positions"

<400> SEQUENCE: 22
aatgatacgg cgaccaccga gatctacact ctttccctac acgacgctct tccgatctag     60
gtgcgctaag ttctagatcg ccaactggtt gtggccttag cagtctugat cagctgctac    120
tgtacgtagc atctatagcc ggcttgctct ctctgcctct agcagctgct ccctatagtg    180
agtcgtatta acgatcggaa gagcacacgt ctgaactcca gtcacgccaa tatctcgtat    240
gccgtcttct gcttg                                                    255

<210> SEQ ID NO 23
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 23
cacagatgtc tgcctgttca                                                 20

<210> SEQ ID NO 24
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 24
```
agggtggtga atgtgaaacc                                              20

<210> SEQ ID NO 25
<211> LENGTH: 2018
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 25
cacagatgtc tgcctgttca tccgcgtcca gctcgttgag tttctccaga agcgttaatg    60
tctggcttct gataaagcgg gccatgttaa gggcggtttt ttcctgtttg gtcactgatg   120
cctccgtgta aggggatttt ctgttcatgg gggtaatgat accgatgaaa cgagagagga   180
tgctcacgat acgggttact gatgatgaac atgcccggtt actggaacgt tgtgagggta   240
aacaactggc ggtatggatg cggcgggacc agagaaaaat cactcagggt caatgccagc   300
gcttcgttaa tacagatgta ggtgttccac agggtagcca gcagcatcct gcgatgcaga   360
tccggaacat aatggtgcag ggcgctgact tccgcgtttc cagactttac gaaacacgga   420
aaccgaagac cattcatgtt gttgctcagg tcgcagacgt tttgcagcag cagtcgcttc   480
acgttcgctc gcgtatcggt gattcattct gctaaccagt aaggcaaccc cgccagccta   540
gccgggtcct caacgacagg agcacgatca tgcgcacccg tggggccgcc atgccggcga   600
taatggcctg cttctcgccg aaacgtttgg tggcgggacc agtgacgaag gcttgagcga   660
gggcgtgcaa gattccgaat accgcaagcg acaggccgat catcgtcgcg ctccagcgaa   720
agcggtcctc gccgaaaatg acccagagcg ctgccggcac ctgtcctacg agttgcatga   780
taaagaagac agtcataagt gcggcgacga tagtcatgcc ccgcgcccac cggaaggagc   840
tgactgggtt gaaggctctc aagggcatcg gtcgagatcc cggtgcctaa tgagtgagct   900
aacttacatt aattgcgttg cgctcactgc ccgctttcca gtcgggaaac ctgtcgtgcc   960
agctgcatta tgaatcggc caacgcgcgg ggagaggcgg tttgcgtatt gggcgccagg  1020
gtggttttc tttcaccag tgagacgggc aacagctgat tgcccttcac cgcctggccc  1080
tgagagagtt gcagcaagcg gtccacgctg gtttgcccca gcaggcgaaa atcctgtttg  1140
atggtggtta acggcgggat ataacatgag ctgtcttcgg tatcgtcgta tcccactacc  1200
gagatatccg caccaacgcg cagcccggac tcggtaatgg cgcgcattgc gcccagcgcc  1260
atctgatcgt tggcaaccag catcgcagtg gaacgatgc cctcattcag catttgcatg  1320
gtttgttgaa aaccggacat ggcactccag tcgccttccc gttccgctat cggctgaatt  1380
tgattgcgag tgagatattt atgccagcca gccagacgca gacgcgccga dacagaactt  1440
aatgggcccg ctaacagcgc gatttgctgg tgacccaatg cgaccagatg ctccacgccc  1500
agtcgcgtac cgtcttcatg ggagaaaata atactgttga tgggtgtctg gtcagagaca  1560
tcaagaaata acgccggaac attagtgcag gcagcttcca cagcaatggc atcctggtca  1620
tccagcggat agttaatgat cagcccactg acgcgttgcg cgagaagatt gtgcaccgcc  1680
gctttacagg cttcgacgcc gcttcgttct accatcgaca ccaccacgct ggcacccagt  1740
tgatcggcgc gagatttaat cgccgcgaca atttgcgacg gcgcgtgcag ggccagactg  1800
gaggtggcaa cgccaatcag caacgactgt ttgcccgcca gttgttgtgc cacgcggttg  1860
ggaatgtaat tcagctccgc catcgccgct tccactttt cccgcgtttt cgcagaaacg  1920
tggctggcct ggttcaccac gcgggaaacg gtctgataag agacaccggc atactctgcg    1980
acatcgtata acgttactgg tttcacattc accaccct    2018

<210> SEQ ID NO 26
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 26
atactcatca ttaaacttcg cccttaccta ccacttcgtg tatgtagata ggtagtatac    60
aattgatatc gaaatgagta cgtagatagt agaaagtaag atggaggtga gagtgagagt    120

<210> SEQ ID NO 27
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
atactcatca ttaaacttcg cccttaccta ccacttcg    38

<210> SEQ ID NO 28
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 28
gcggcgtgat actggtcccg agcctgaagt taggcccggg atgactgaca gtcttccgag    60
accgacgaca caggtctccc tatagtgagt cgtattatgg cgagagaatg aatctccatc    120

<210> SEQ ID NO 29
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 29
gatggagatt cattctctcg ccataatacg actcactata gg    42

<210> SEQ ID NO 30
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (50)..(50)
<223> OTHER INFORMATION: a, c, t, g, unknown or other
<220> FEATURE:
<221> NAME/KEY: modified_base

```
<222> LOCATION: (52)..(53)
<223> OTHER INFORMATION: a, c, t, g, unknown or other

<400> SEQUENCE: 30
gaagatgcag aagacaggaa ggatgaaaca ctcaggcgca cgctggcatn cnngacaaac    60
cacaagaaca ggctagtgag aatgaaggga                                    90

<210> SEQ ID NO 31
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (49)..(49)
<223> OTHER INFORMATION: a, c, t, g, unknown or other
<220> FEATURE:
<221> NAME/KEY: modified_base
<222> LOCATION: (51)..(52)
<223> OTHER INFORMATION: a, c, t, g, unknown or other

<400> SEQUENCE: 31
ccaactctga aacccaccaa cgccaacatc caccacacaa cccaagatnc nngaccatct    60
tacaaacata tcccttcatt ctcactagcc                                    90

<210> SEQ ID NO 32
<211> LENGTH: 160
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (50)..(50)
<223> OTHER INFORMATION: a, c, t, g, unknown or other
<220> FEATURE:
<221> NAME/KEY: modified_base
<222> LOCATION: (52)..(53)
<223> OTHER INFORMATION: a, c, t, g, unknown or other
<220> FEATURE:
<221> NAME/KEY: modified_base
<222> LOCATION: (109)..(110)
<223> OTHER INFORMATION: a, c, t, g, unknown or other
<220> FEATURE:
<221> NAME/KEY: modified_base
<222> LOCATION: (112)..(112)
<223> OTHER INFORMATION: a, c, t, g, unknown or other

<400> SEQUENCE: 32
gaagatgcag aagacaggaa ggatgaaaca ctcaggcgca cgctggcatn cnngacaaac    60
cacaagaaca ggctagtgag aatgaaggga tatgtttgta agatggtcnn gnatcttggg   120
ttgtgtggtg gatgttggcg ttggtgggtt tcagagttgg                        160

<210> SEQ ID NO 33
<211> LENGTH: 160
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (49)..(49)
```

```
<223> OTHER INFORMATION: a, c, t, g, unknown or other
<220> FEATURE:
<221> NAME/KEY: modified_base
<222> LOCATION: (51)..(52)
<223> OTHER INFORMATION: a, c, t, g, unknown or other
<220> FEATURE:
<221> NAME/KEY: modified_base
<222> LOCATION: (108)..(109)
<223> OTHER INFORMATION: a, c, t, g, unknown or other
<220> FEATURE:
<221> NAME/KEY: modified_base
<222> LOCATION: (111)..(111)
<223> OTHER INFORMATION: a, c, t, g, unknown or other

<400> SEQUENCE: 33
ccaactctga aacccaccaa cgccaacatc caccacacaa cccaagatnc nngaccatct      60
tacaaacata tcccttcatt ctcactagcc tgttcttgtg gtttgtcnng natgccagcg    120
tgcgcctgag tgtttcatcc ttcctgtctt ctgcatcttc                          160

<210> SEQ ID NO 34
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 34
cattactcac ttccccactt                                                 20

<210> SEQ ID NO 35
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 35
gctgcagatt ggagccaaag                                                 20

<210> SEQ ID NO 36
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 36
ttgatggtga tggtggagcc                                                 20

<210> SEQ ID NO 37
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 37
tcagtgctca tggactcata ct                                              22
```

```
<210> SEQ ID NO 38
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 38
ataccctggg agcaaagttg ttg                                          23

<210> SEQ ID NO 39
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 39
cccactagac atgctctgcc                                              20

<210> SEQ ID NO 40
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 40
caaaatgttg cttgccttcc g                                            21

<210> SEQ ID NO 41
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 41
tccctgagcc ctgatctagt                                              20

<210> SEQ ID NO 42
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 42
aatactggct gaccggttct                                              20

<210> SEQ ID NO 43
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 43
acaccacagc agaagagagc                                              20

<210> SEQ ID NO 44
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 44
taggattgtt gcacaggcca                                              20

<210> SEQ ID NO 45
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 45
gctgagctgt atccttgagg t                                            21

<210> SEQ ID NO 46
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 46
acacgtgggt attccacagc                                              20

<210> SEQ ID NO 47
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 47
gtggatcttc agtggtggca                                              20

<210> SEQ ID NO 48
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 48
atgctccctc atcctttgca                                              20

<210> SEQ ID NO 49
<211> LENGTH: 20
<212> TYPE: DNA
<213> ORGANISM: Artificial Sequence -continued

```
<220> FEATURE:
<221> NAME/KEY: source
<223> OTHER INFORMATION: /note="Description of Artificial Sequence:
      Synthetic primer"

<400> SEQUENCE: 49
agcctctgaa cttgactgcc                                          20

<210> SEQ ID NO 50
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 50
gcctggaact cctgacagtc                                          20

<210> SEQ ID NO 51
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 51
ggtccttgat ccacccagac                                          20

<210> SEQ ID NO 52
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 52
acatggtgct ggtctaaccg                                          20

<210> SEQ ID NO 53
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 53
catcgagcat caaatgaaac tgc                                      23

<210> SEQ ID NO 54
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 54
acgttatacg atgtcgcaga gt                                       22
```

<210> SEQ ID NO 55
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 55
aggcaacttt atgcccatgc aa                                              22

<210> SEQ ID NO 56
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 56
ccaaggggtt atgctagtta ttgc                                            24

<210> SEQ ID NO 57
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
tcgaccggat c                                                          11

<210> SEQ ID NO 58
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 58
tcgacuggat c                                                          11

<210> SEQ ID NO 59
<211> LENGTH: 13
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
gtcgaccgga tcc                                                        13

<210> SEQ ID NO 60
<211> LENGTH: 13
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 60
gtcgaccgga tcc                                                            13

<210> SEQ ID NO 61
<211> LENGTH: 13
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 61
gtcgaccgga tcu                                                            13

<210> SEQ ID NO 62
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
tcgaccggat c                                                              11

<210> SEQ ID NO 63
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
tcgaccggat c                                                              11

<210> SEQ ID NO 64
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
tcgaccggat c                                                              11

<210> SEQ ID NO 65
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 65
tcgaccggat c                                                         11

<210> SEQ ID NO 66
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
tcgaccggat c                                                         11

<210> SEQ ID NO 67
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
cctgtcgagc                                                           10

<210> SEQ ID NO 68
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
cctgttgagc                                                           10

<210> SEQ ID NO 69
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
agtcttgatc                                                           10

<210> SEQ ID NO 70
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
agtctcgatc                                                           10

<210> SEQ ID NO 71
<211> LENGTH: 119
<212> TYPE: DNA
<213> ORGANISM: Artificial Sequence
```

<220> FEATURE:
<221> NAME/KEY: source
<223> OTHER INFORMATION: /note="Description of Artificial Sequence:
      Synthetic polynucleotide"

<400> SEQUENCE: 71

```
atactcatca ttaaacttcg cccttaccta ccacttcgtg tatgatgata ggtagtatac    60
aattgatatc gaaatgagta cgtagatagt agaaagtaag atggaggtga gagtgagag    119
```

<210> SEQ ID NO 72
<211> LENGTH: 119
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 72

```
atactcatca ttaaacttcg cccttaccta ccacttcgtg tatgtagata ggtagtatac    60
aattgatatc gaaatgagta cgtagatagt agaaagtaag atggaggtga gagtgagag    119
```

<210> SEQ ID NO 73
<211> LENGTH: 119
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 73

```
ctctcactct cacctccatc ttactttcta ctatctacgt actcatttcg atatcaattg    60
tatactacct atctacatac acgaagtggt aggtaagggc gaagtttaat gatgagtat    119
```

<210> SEQ ID NO 74
<211> LENGTH: 113
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 74

```
gcgtgatact ggtcccgagc ctgaagttag gcccgggatg actgacagtc ttccgagacc    60
gacgacacag gtctccctat agtgagtcgt attatggcga gagaatgaat ctc          113
```

<210> SEQ ID NO 75
<211> LENGTH: 113
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 75

```
gagattcatt ctctcgccat aatacgactc actatagggA gacctgtgtc gtcggtctcg    60
gaagactgtc agtcatcccg ggcctaactt caggctcggg accagtatca cgc          113
```

<210> SEQ ID NO 76
<211> LENGTH: 10
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
cctgtcgagc                                                            10
```